United States Patent [19]
Anthony et al.

[11] Patent Number: 5,939,439
[45] Date of Patent: Aug. 17, 1999

[54] INHIBITORS OF FARNESYL-PROTEIN TRANSFERASE

[75] Inventors: Neville J. Anthony, Hatfield; Samuel L. Graham, Schwenksville; Lekhanh O. Tran, Norristown; Ian M. Bell, Harleysville; S. Jane deSolms, Norristown; Robert P. Gomez, Perkasie; Michelle Sparks Kuo, Gwynedd Valley; William C. Lumma, Jr., Pennsburg; Debra S. Perlow, East Greenville; Anthony W. Shaw, Lansdale; John S. Wai, Harleysville; Steven D. Young, Lansdale, all of Pa.

[73] Assignee: Merck & Co., Inc., Rahway, N.J.

[21] Appl. No.: 08/995,744

[22] Filed: Dec. 22, 1997

Related U.S. Application Data

[60] Provisional application No. 60/033,990, Dec. 30, 1996.

[51] Int. Cl.$^6$ .......................... C07D 401/04; A61K 31/44
[52] U.S. Cl. .......................... 514/333; 514/252; 546/256; 544/405
[58] Field of Search .......................... 546/256; 544/405; 514/333, 252

[56] References Cited

U.S. PATENT DOCUMENTS

| | | | |
|---|---|---|---|
| 4,713,387 | 12/1987 | Watanabe et al. | 514/332 |
| 5,428,164 | 6/1995 | Thurkauf et al. | 544/295 |
| 5,578,629 | 11/1996 | Ciccarone et al. | 514/397 |
| 5,616,601 | 4/1997 | Khanna et al. | 514/399 |
| 5,646,280 | 7/1997 | Thurkauf et al. | 544/295 |
| 5,656,762 | 8/1997 | Thurkauf et al. | 544/370 |

FOREIGN PATENT DOCUMENTS

| | | |
|---|---|---|
| 0 393 607 A2 | 10/1990 | European Pat. Off. . |
| 0 508 393 A1 | 10/1992 | European Pat. Off. . |
| 0 612 731 A1 | 8/1994 | European Pat. Off. . |
| WO 94/08990 | 4/1994 | WIPO . |
| WO 96/34851 | 11/1996 | WIPO . |
| WO 97/36890 | 10/1997 | WIPO . |
| WO 97/36896 | 10/1997 | WIPO . |
| WO 97/36897 | 10/1997 | WIPO . |
| WO 97/36898 | 10/1997 | WIPO . |
| WO 97/36901 | 10/1997 | WIPO . |

OTHER PUBLICATIONS

Exp. Opin, Ther. Patents, vol. 6, No. 12, pp. 1295–1304 (1996), by S. Graham, et al.
Exp. Opin. Ther. Patents, vol. 5, No. 12, pp. 1269–1285 (1995), by S. L. Graham.
Cancer Research, vol. 55, pp. 5302–5309 (1995), by L. Sepp–Lorenzino, et al.
Nature Medicine, vol. 1, No. 8, pp. 792–797 (1995), by N. Kohl, et al.
Proc. Natl. Acad. Sci. USA, vol. 91, pp. 9141–9145 (1994), by N. Kohl, et al.
Science, vol. 260, pp. 1934–1937 (1993), by N. Kohl, et al.
J. of Biol. Chem., vol. 270, No. 11, pp. 6221–6226 (1995), by G. James, et al.
J. of Biol. Chem., vol. 269, No. 44, pp. 27705–27714 (1994), by G. James, et al.
J. of Biol. Chem., vol. 265, No. 11, pp. 7617–7620 (1993), by J. Gibbs, et al.
CA 99:203546, Matsuzaka et al., 1983.

*Primary Examiner*—Jane Fan
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

21 Claims, No Drawings

INHIBITORS OF FARNESYL-PROTEIN TRANSFERASE

This application claims the priority of provisional application 60/033,990 filed Dec. 30, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in four general classes (S. Graham, *Expert Opinion Ther. Patents*, (1995) 5:1269–1285). The first are analogs of farnesyl diphosphate (FPP), while a second class of inhibitors is related to the protein substrates (e.g., Ras) for the enzyme. Bisubstrate inhibitors and inhibitors of farnesyl-protein transferase that are non-competitive with the substrates have also been described. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

Recently, certain tricyclic compounds which optionally incorporate a piperidine moiety have been disclosed to be inhibitors of FPTase (WO 95/10514, WO 95/10515 and WO 95/10516). Imidazole-containing compounds which are claimed to be inhibitors of farnesyl protein transferase have also been disclosed (WO 95/09001 and EP 0 675 112 A1). WO 95/09001 discloses imidazolyl containing compounds that are inhibitors of farnesyl protein transferase.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It is, therefore, an object of this invention to develop low molecular weight compounds that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises bicyclic compounds which inhibit the farnesyl-protein transferase. Further contained in this invention are chemotherapeutic compositions containing these farnesyl transferase inhibitors and methods for their production.

The compounds of this invention are illustrated by the formula A:

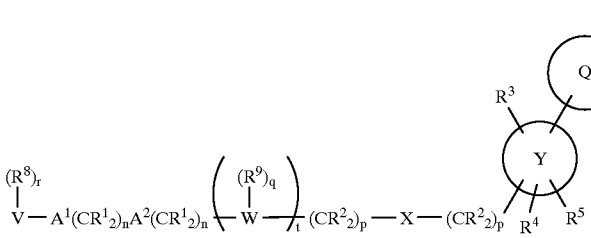

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

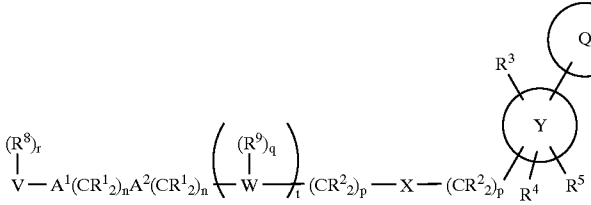

wherein:

Q is a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y;

Y is a 5, 6 or 7 membered carbocyclic ring wherein from 0 to 3 carbon atoms are replaced by a heteroatom selected from N, S and O, and wherein Y is attached to Q through a carbon atom;

R$^1$ and R$^2$ are independently selected from:
   a) hydrogen,
   b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, R$^{11}$C(O)O—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
   c) unsubstituted or substituted C$_1$–C$_6$ alkyl wherein the substituent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^3$, R$^4$ and R$^5$ are independently selected from:
   a) hydrogen,
   b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$C(O)O—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
   c) unsubstituted C$_1$–C$_6$ alkyl,
   d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^{6a}$, R$^{6b}$, R$^{6c}$, R$^{6d}$ and R$^{6e}$ are independently selected from:
   a) hydrogen,
   b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$S(O)$_2$NR$^{10}$—, (R$^{10}$)$_2$NS(O)$_2$—, R$^{11}$C(O)O—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
   c) unsubstituted C$_1$–C$_6$ alkyl,
   d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, R$^{10}$C(O)—, N$_3$, —N(R$^{10}$)$_2$, and R$^{11}$OC(O)—NR$^{10}$—; or
any two of R$^{6a}$, R$^{6b}$, R$^{6c}$, R$^{6d}$ and R$^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

R$^7$ is selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
   a) C$_{1-4}$ alkoxy, b) aryl or heterocycle, c) $\underset{O}{\overset{R^{11}}{\underset{\parallel}{\bigvee}}}$, d) —SO$_2$R$^{11}$
e) N(R$^{10}$)$_2$ or
f) C$_{1-4}$ perfluoroalkyl;

R$^8$ is independently selected from:
a) hydrogen,
b) aryl, substituted aryl, heterocycle, substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is independently selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, amino-C$_1$–C$_6$ alkyl, N-(unsubstituted or substituted benzolyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl;

R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted hetaryl, C$_1$–C$_6$ perfluoroalkyl, 2-aminoethyl and 2,2,2-trifluoroethyl;

R$^{13}$ is selected from hydrogen, C$_1$–C$_6$ alkyl, cyano, C$_1$–C$_6$ alkylsulfonyl and C$_1$–C$_6$ acyl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) C$_1$–C$_{20}$ alkyl wherein from 0 to 4 carbon atoms are replaced with a heteroatom selected from O, S, and N, and
e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;

X is a bond, —CH=CH—, O, —C(=O)—, —C(O)NR$^7$—, —NR$^7$C(O)—, —C(O)O—, —OC(O)—, —C(O)NR$^7$C(O)—, —NR$^7$—, —S(O)$_2$N(R$^{10}$)—, —N(R$^{10}$)S(O)$_2$— or —S(=O)$_m$—;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or a pharmaceutically acceptable salt thereof.

A preferred embodiment of the compounds of this invention is illustrated by the following formula A-1:

A-1

$$V-A^1(CR^1{}_2)_nA^2(CR^1{}_2)_n\underset{(R^8)_r}{|}\left(\underset{(R^9)_q}{|}W\right)_t(CR^2{}_2)_p-X-(CR^2{}_2)_p\underset{R^4\ R^5}{\overset{R^3\ Q\ R^{6a-e}}{\bigg\langle\!\!\bigg\rangle}}$$

wherein:

Q is a 4, 5, 6 or 7 membered heterocyclic ring which comprises a nitrogen atom through which Q is attached to Y and 0–2 additional heteroatoms selected from N, S and O, and which also comprises a carbonyl or sulfonyl moiety adjacent to the nitrogen atom attached to Y;

from 0–2 of f(s) are independently N, and the remaining f's are independently CH, wherein Y is attached to Q through a carbon atom;

R$^1$ is independently selected from: hydrogen, C$_3$–C$_{10}$ cycloalkyl, R$^{10}$O—, —N(R$^{10}$)$_2$, F or C$_1$–C$_6$ alkyl;

R$^2$ is independently selected from:
a) hydrogen,
b) aryl, heterocycle, C$_3$–C$_{10}$ cycloalkyl, R$^{10}$O—, R$^{11}$C(O)O—, —N(R$^{10}$)$_2$, F or C$_2$–C$_6$ alkenyl,
c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^{10}$O— and —N(R$^{10}$)$_2$;

R$^3$, R$^4$ and R$^5$ are independently selected from:
a) hydrogen,
b) unsubstituted or substituted aryl, unsubstituted or substituted heterocycle, C$_3$–C$_{10}$ cycloalkyl, C$_2$–C$_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}O-$, $(R^{10})_2NC(O)-$, $R^{10}_2N-C(NR^{10})-$, CN, $NO_2$, $R^{10}C(O)-$, $N_3$, $-N(R^{10})_2$, or $R^{11}OC(O)NR^{10}-$, c) unsubstituted $C_1-C_6$ alkyl;

d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}_2N-C(NR^{10})-$, CN, $R^{10}C(O)-$, $N_3$, $-N(R^{10})_2$, and $R^1OC(O)-NR^{10}-$;

$R^{6a}$, $R^{6b}$, $R^{6c}$, $R^{6d}$ and $R^{6e}$ are independently selected from:

a) hydrogen, b) unsubstituted or substituted aryl, unsubstituted or substituted heterocycle, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{11}S(O)_2NR^{10}-$, $(R^{10})_2NS(O)_2-$, $R^{10}_2N-C(NR^{10})-$, CN, $NO_2$, $R^{10}C(O)-$, $N_3$, $-N(R^{10})_2$, or $R^{11}OC(O)NR^{10}-$, c) unsubstituted $C_1-C_6$ alkyl;

d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{11}S(O)_2NR^{10}-$, $(R^{10})_2NS(O)_2-$, $R^{10}_2N-C(NR^{10})-$, CN, $R^{10}C(O)-$, $N_3$, $-N(R^{10})_2$, and $R^{11}OC(O)-NR^{10}-$; or any two of $R^{6a}$, $R^{6b}$, $R^{6c}$, $R^{6d}$ and $R^{6e}$ on adjacent carbon atoms are combined to form a diradical selected from $-CH=CH-CH=CH-$, $-CH=CH-CH_2-$, $-(CH_2)_4-$ and $-(CH_2)_3-$;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy, b) aryl or heterocycle, c) 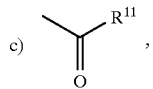, d) $-SO_2R^{11}$, e) $N(R^{10})_2$ or f) $C_{1-4}$ perfluoroalkyl;

$R^8$ is independently selected from:

a) hydrogen, b) aryl, substituted aryl, heterocycle, substituted heterocycle, $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, $(R^{10})_2NC(O)-$, $R^{11}S(O)_2NR^{10}-$, $(R^{10})_2NS(O)_2-$, CN, $NO_2$, $(R^{10})_2N-C(NR^{10})-$, $R^{10}C(O)-$, $-N(R^{10})_2$, or $R^{11}OC(O)NR^{10}-$, and c) $C_1-C_6$ alkyl substituted by $C_1-C_6$ perfluoroalkyl, $R^{10}O-$, $R^{10}C(O)NR^{10}-$, $(R^{10})_2NC(O)-$, $R^{11}S(O)_2NR^{10}-$, $(R^{10})_2NS(O)_2-$, $(R^{10})_2N-C(NR^{10})-$, $R^{10}C(O)-$, $-N(R^{10})_2$, or $R^{11}OC(O)NR^{10}-$;

$R^9$ is selected from:

a) hydrogen, b) $C_2-C_6$ alkenyl, $C_2-C_6$ alkynyl, $C_1-C_6$ perfluoroalkyl, F, Cl, $R^{10}O-$, $R^{11}S(O)_m-$, $R^{10}C(O)NR^{10}-$, $(R^{10})_2NC(O)-$, CN, $NO_2$, $(R^{10})_2N-C(NR^{10})-$, $R^{10}C(O)-$, $-N(R^{10})_2$, or $R^{11}OC(O)NR^{10}-$, and c) $C_1-C_6$ alkyl unsubstituted or substituted by $C_1-C_6$ perfluoroalkyl, F, Cl, $R^{10}O-$, $R^{11}S(O)_m-$, $R^{10}C(O)NR^{10}-$, $(R^{10})_2NC(O)-$, CN, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1-C_6$ alkyl, amino-$C_1-C_6$ alkyl, N-(unsubstituted or substituted benzolyl)-amino-$C_1-C_6$ alkyl, ($C_1-C_6$ alkyl)$_2$-amino-$C_1-C_6$ alkyl, acetylamino-$C_1-C_6$ alkyl, phenyl-$C_1-C_6$ alkyl, 2,2,2-trifluoroethyl, aryl and substituted aryl;

$R^{11}$ is independently selected from $C_1-C_6$ alkyl and aryl;

$R^{12}$ is independently selected from hydrogen, $C_1-C_6$ alkyl, $C_1-C_6$ aralkyl, $C_1-C_6$ substituted aralkyl, $C_1-C_6$ heteroaralkyl, $C_1-C_6$ substituted heteroaralkyl, aryl, substituted aryl, heteroaryl, substituted hetaryl, $C_1-C_6$ perfluoroalkyl, 2-aminoethyl and 2,2,2-trifluoroethyl;

$A^1$ and $A^2$ are independently selected from: a bond, $-CH=CH-$, $-C\equiv C-$, $-C(O)-$, $-C(O)NR^{10}-$, O, $-N(R^{10})-$, or $S(O)_m$;

V is selected from:

a) hydrogen, b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl, c) aryl, d) $C_1-C_{20}$ alkyl wherein from 0 to 4 carbon atoms are replaced with a heteroatom selected from O, S, and N, and e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, oxazolyl, indolyl, quinolinyl, triazolyl or isoquinolinyl;

X is a bond, O, $-C(=O)-$, $-CH=CH-$, $-C(O)NR^7-$, $-NR^7C(O)-$, $-NR^7-$, $-S(O)_2N(R^{10})-$, $-N(R^{10})S(O)_2-$ or $-S(=O)_m-$;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or a pharmaceutically acceptable salt thereof.

A preferred embodiment of the compounds of this invention are illustrated by the formula B:

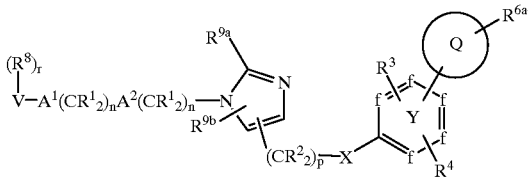

wherein:

Q is a 5 or 6 membered heterocyclic ring which comprises a nitrogen atom through which Q is attached to Y and 0–1 additional heteroatoms selected from N, S and O, and which also comprises a carbonyl or sulfonyl moiety adjacent to the nitrogen atom attached to Y;

from 0–2 of f(s) are independently N, and the remaining f's are independently CH, wherein Y is attached to Q through a carbon atom;

$R^1$ is selected from: hydrogen, $C_3$–$C_{10}$ cycloalkyl, $R^{10}$O—, —N($R^{10}$)$_2$, F or $C_1$–$C_6$ alkyl;

$R^2$ is independently selected from:
a) hydrogen,
b) aryl, heterocycle, $C_3$–$C_{10}$ cycloalkyl, $R^{10}$O—, $R^{11}$C(O)O—, —N($R^{10}$)$_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}$O— and —N($R^{10}$)$_2$;

$R^3$ and $R^4$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}_2$N—C(NR$^{10}$)—, CN, NO$_2$, $R^{10}$C(O)—, N$_3$, —N($R^{10}$)$_2$, or $R^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}_2$N—C(NR$^{10}$)—, CN, $R^{10}$C(O)—, N$_3$, —N($R^{10}$)$_2$, and $R^{11}$OC(O)—NR$^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{11}$S(O)$_2$NR$^{10}$—, ($R^{10}$)$_2$NS(O)$_2$—, $R^{10}_2$N—C(NR$^{10}$)—, CN, NO$_2$, $R^{10}$C(O)—, N$_3$, —N($R^{10}$)$_2$, or $R^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—9 $R^{11}$S(O)$_2$NR$^{10}$—, ($R^{10}$)$_2$NS(O)$_2$—, $R^{10}_2$N—C(NR$^{10}$)—, CN, $R^{10}$C(O)—, N$_3$, —N($R^{10}$)$_2$, and $R^{11}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}$O—, $R^{10}$C(O)NR$^{10}$—, ($R^{10}$)$_2$NC(O)—, $R^{11}$S(O)$_2$NR$^{10}$—, ($R^{10}$)$_2$NS(O)$_2$—, CN, NO$_2$, ($R^{10}$)$_2$N—C(NR$^{10}$)—, $R^{10}$C(O)—, —N($R^{10}$)$_2$, or $R^{11}$OC(O)NR$^{10}$—, and
c) $C_1$–$C_6$ alkyl substituted by $C_1$–$C_6$ perfluoroalkyl, $R^{10}$O—, $R^{10}$C(O)NR$^{10}$—, ($R^{10}$)$_2$NC(O)—, $R^{11}$S(O)$_2$ NR$^{10}$—, ($R^{10}$)$_2$NS(O)$_2$—, ($R^{10}$)$_2$N—C(NR$^{10}$)—, $R^{10}$C(O)—, —N($R^{10}$)$_2$, or $R^{11}$OC(O)NR$^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N($R^{10}$)—, or S(O)$_m$;

V is selected from:
a) hydrogen,
b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

X is a bond, —CH=CH—, —C(O)NR$^{10}$—, —NR$^{10}$C(O)—, —NR$^{10}$—, O or —C(=O)—;

m is 0, 1 or 2;

n is independently 0, 1, 2, 3 or 4;

p is 0, 1, 2, 3 or 4; and r is 0 to 5, provided that r is 0 when V is hydrogen;

or a pharmaceutically acceptable salt thereof.

Another preferred embodiment of the compounds of this invention are illustrated by the formula C:

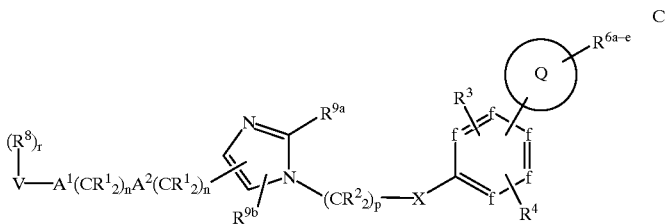

wherein:

Q is a 5 or 6 membered heterocyclic ring which comprises a nitrogen atom through which Q is attached to Y and 0–1 additional heteroatoms selected from N, S and O, and which also comprises a carbonyl or sulfonyl moiety adjacent to the nitrogen atom attached to Y; from 1–2 of f(s) are independently N, and the remaining f's are independently CH;

$R^1$ is selected from: hydrogen, $C_3$–$C_{10}$ cycloalkyl, $R^{10}O$—, —$N(R^{10})_2$, F or $C_1$–$C_6$ alkyl, wherein Y is attached to Q through a carbon atom;

$R^2$ is independently selected from:
- a) hydrogen,
- b) aryl, heterocycle, $C_3$–$C_{10}$ cycloalkyl, $R^{10}O$—, $R^{11}C(O)O$—, —$N(R^{10})_2$, F or $C_2$–$C_6$ alkenyl,
- c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;

$R^3$ and $R^4$ are independently selected from:
- a) hydrogen,
- b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $CN(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
- c) unsubstituted $C_1$–$C_6$ alkyl,
- d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

$R^{6a}$, $R^{6b}$, $R^{6c}$, $R^{6d}$ and $R^{6e}$ are independently selected from:
- a) hydrogen,
- b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
- c) unsubstituted $C_1$–$C_6$ alkyl,
- d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $(R^{10})_2NC(O)$—, $R^{11}S(O)_2NR^{10}$—, $(R^{10})_2NS(O)_2$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
- a) hydrogen,
- b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(RIO)_2$, or $R^{11}OC(O)NR^{10}$—, and
- c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, $(C_1$–$C_6$ alkyl$)_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or $S(O)_m$;

V is selected from:
- a) hydrogen,
- b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
- c) aryl,
- d) $C_1$–$C_{20}$ alkyl wherein from 0 to 4 carbon atoms are replaced with a heteroatom selected from O, S, and N, and
- e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, —CH=CH—, —C(O)NR$^{10}$—, —NR$^{10}$C(O)—, —NR$^{10}$O—, O or —C(=O)—;

m is 0, 1 or 2;

n is independently 0, 1, 2, 3 or 4;

p is 0, 1, 2, 3 or 4, provided that p is not 0 if X is a bond or O; and r is 0 to 5, provided that r is 0 when V is hydrogen;

or a pharmaceutically acceptable salt thereof.

In a more preferred embodiment of this invention, the inhibitors of farnesyl-protein transferase are illustrated by the formula D:

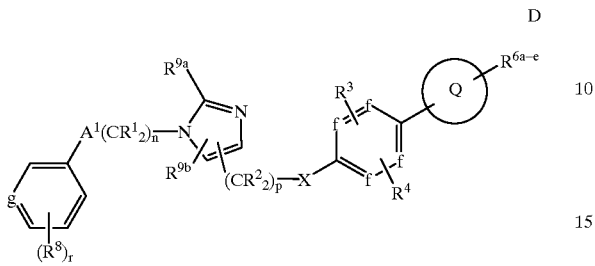

wherein:

Q is selected from

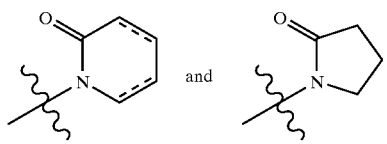

from 0–2 of f(s) are independently N, and the remaining f's are independently CH;

g is selected from N and CH;

$R^1$ is selected from: hydrogen, $C_3$–$C_{10}$ cycloalkyl or $C_1$–$C_6$ alkyl;

$R^2$ is independently selected from:
a) hydrogen,
b) aryl, heterocycle, $C_3$–$C_{10}$ cycloalkyl, $R^{10}$O—, —N($R^{10}$)$_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}$O—, or —N($R^{10}$)$_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, NO$_2$, $R^{10}$C(O)—, N$_3$, —N($R^{10}$)$_2$, or $R^1$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, $R^{10}$C(O)—, N$_3$, —N($R^{10}$)$_2$, and $R^{11}$OC(O)NR$^{10}$—;

$R^4$ is selected from H, halogen, $C_1$–$C_6$ alkyl and CF$_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, NO$_2$, $R^{10}$C(O)—, N$_3$, —N($R^{10}$)$_2$, or $R^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, $R^{10}$C(O)—, N$_3$, —N($R^{10}$)$_2$, and $R^{10}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

$R^8$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}$O—, $R^{10}$C(O)NR$^{10}$—, CN, NO$_2$, ($R^{10}$)$_2$N—C(NR$^{10}$)—, $R^{10}$C(O)—, —N($R^{10}$)$_2$, or $R^{11}$OC(O)NR$^{10}$—, and
c) $C_1$–$C_6$ alkyl substituted by $C_1$–$C_6$ perfluoroalkyl, $R^{10}$O—, $R^{10}$C(O)NR$^{10}$—, ($R^{10}$)$_2$N—C(NR$^{10}$)—, $R^{10}$C(O)—, —N($R^{10}$)$_2$, or $R^{11}$OC(O)NR$^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ is selected from: a bond, —C(O)—, O, —N($R^{10}$)—, or S(O)$_m$;

X is a bond, —CH=CH—, —C(O)NR$^{10}$—, —NR$^{10}$C(O)—, —NR$^{10}$—, O or n is 0 or 1; provided that n is not 0 if $A^1$ is a bond, O, —N($R^{10}$)— or S(O)$_m$;

m is 0, 1 or 2;

p is 0, 1, 2, 3 or 4; and r is 0, 1 or 2;

the dashed lines ( - - - ) represent optional double bonds;

or a pharmaceutically acceptable salt thereof.

In another more preferred embodiment of this invention, the inhibitors of farnesyl-protein transferase are illustrated by the formula E:

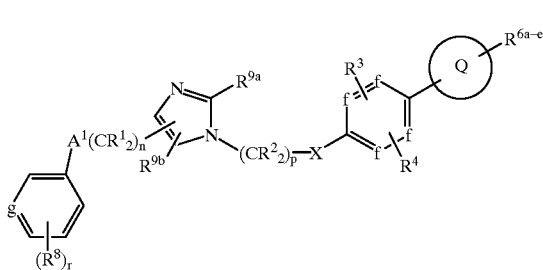

E wherein:

Q is selected from

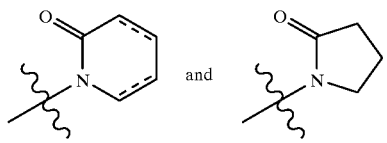

and from 0–2 of f(s) are independently N, and the remaining f's are independently CH;

g is selected from N and CH;

$R^1$ is selected from: hydrogen, $C_3$–$C_{10}$ cycloalkyl, $R^{10}O$—, $-N(R^{10})_2$, F or $C_1$–$C_6$ alkyl;

$R^2$ is independently selected from:
 a) hydrogen,
 b) aryl, heterocycle, $C_3$–$C_{10}$ cycloalkyl, $R^{10}O$—, $-N(R^{10})_2$, F or $C_2$–$C_6$ alkenyl,
 c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or $-N(R^{10})_2$;

$R^3$ is selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, $-N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, $-N(R^{10})_2$, and $R^{11}OC(O)NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, $-N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, $-N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

$R^8$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $-N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $-N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

X is a bond, —CH=CH—, —C(O)$NR^{10}$—, —$NR^{10}C(O)$—, —$NR^{10}$—, O or —C(=O)—;

n is 0 or 1;

m is 0, 1 or 2;

p is 0, 1, 2, 3 or 4, provided that p is not 0 if X is a bond or O; and r is 0, 1 or 2 the dashed lines ( - - - ) represent optional double bonds;

or a pharmaceutically acceptable salt thereof.

In a further embodiment of this invention, the inhibitors of farnesyl-protein transferase are illustrated by the formula F:

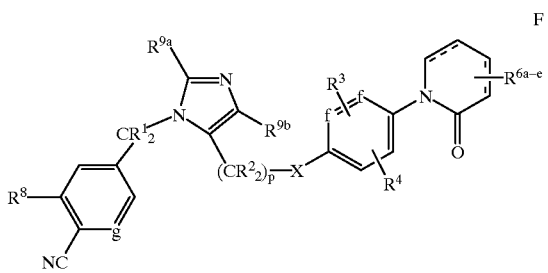

F wherein:

from 0–1 of f(s) are independently N, and the remaining f's are independently CH;

g is selected from N and CH;

$R^1$ is selected from: hydrogen, $C_3$–$C_{10}$ cycloalkyl or $C_1$–$C_6$ alkyl;

$R^2$ is independently selected from:
 a) hydrogen,
 b) aryl, heterocycle, $C_3$–$C_{10}$ cycloalkyl, $R^{10}O$—, —$N(R^{10})_2$ or F,
 c) $C_1$–$C_6$ alkyl unsubstituted or substituted by aryl, heterocycle, $C_3$–$C_{10}$ cycloalkyl, $R^{10}O$—, or —$N(R^{10})_2$;

$R^3$ is selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^4$ is selected from H, halogen, $CH_3$ and $CF_3$;

$R^{6a}$, $R^{6b}$, $R^{6c}$, $R^{6d}$ and $R^{6e}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^8$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

X is a bond, —CH=CH—, —C(O)NR$^{10}$—, —NR$^{10}$C(O)—, —NR$^{10}$—, O or —C(=O)—;

m is 0, 1 or 2; and p is 0, 1, 2, 3 or 4;

the dashed lines ( - - - ) represent optional double bonds; or a pharmaceutically acceptable salt thereof.

In a further embodiment of this invention, the inhibitors of farnesyl-protein transferase are illustrated by the formula G:

wherein:
 from 0–1 of f(s) are independently N, and the remaining f's are independently CH;
 g is selected from N and CH;

$R^1$ is selected from: hydrogen, $C_3$–$C_{10}$ cycloalkyl, $R^{10}O$—, —$N(R^{10})_2$, F or $C_1$–$C_6$ alkyl;

$R^2$ is independently selected from:
 a) hydrogen,
 b) aryl, heterocycle or $C_3$–$C_{10}$ cycloalkyl,
 c) $C_1$–$C_6$ alkyl unsubstituted or substituted by aryl, heterocycle, $C_3$–$C_{10}$ cycloalkyl, $C_2$–$C_6$ or alkenyl;

$R^3$ is selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^4$ is selected from H, halogen, $CH_3$ and $CF_3$;

$R^{6a}$, $R^{6b}$, $R^{6c}$, $R^{6d}$ and $R^{6e}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^1O$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^8$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ and $R^{9b}$ are independently hydrogen, ethyl, cyclopropyl or methyl;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, $(C_1$–$C_6$ alkyl$)_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ is selected from: a bond, —C(O)—, O, —N($R^{10}$)—, or $S(O)_m$;

m is 0, 1 or 2; and n is 0 or 1;

the dashed lines ( - - - ) represent optional double bonds;

or a pharmaceutically acceptable salt thereof.

Preferred compounds of the invention are:

4-{3-[4-(-2-Oxo-2-H-pyridin-1-yl)benzyl]-3-H-imidazol-4-ylmethyl}benzonitrile

4-{3-[4-(3-Methyl-2-oxo-2-H-pyridin-1-yl)benzyl]-3-H-imidazol-4-ylmethyl}benzonitrile 4-{3-[4-(2-Oxo-piperidin-1-yl)benzyl]-3-H-imidazol-4-ylmethyl}benzonitrile 4-{3-[3-Methyl-4-(2-oxopiperidin-1-yl)-benzyl]-3-H-imidazol-4-ylmethyl}-benzonitrile (4-{3-[4-(2-Oxo-pyrrolidin-1-yl)-benzyl]-3H-imidazol-4-ylmethyl}-benzonitrile 4-{3-[4-(3-Methyl-2-oxo-2-H-pyrazin-1-yl)-benzyl]-3-H-imidazol-4-ylmethyl}-benzonitrile 4-{3-[2-Methoxy-4-(2-oxo-2-H-pyridin-1-yl)-benzyl]-3-H-imidazol-4-ylmethyl}-benzonitrile 4-{1-[4-(5-Chloro-2-oxo-2H-pyridin-1-yl)-benzyl]-1H-imidazol-2-ylmethyl}-benzonitrile 4-[1-(2-Oxo-2H-[1,2']bipyridinyl-5'-ylmethyl)-1H-imidazol-2-ylmethyl]-benzonitrile 4-[1-(5-Chloro-2-oxo-2H-[1,2']bipyridinyl-5'-ylmethyl)-1H-imidazol-2-ylmethyl]-benzonitrile 4-[3-(6-Methyl-2-oxo-2-H-[1,2']bipyridinyl-5'-ylmethyl)-3H-imidazol-4-ylmethyl]-benzyonitrile 4-[1-(5-Trifluoromethyl-2-oxo-2H-[1,2']bipyridinyl-5'-ylmethyl)-1H-imidazol-2-ylmethyl]-benzonitrile 4-[1-(3,5-dibromo-2-oxo-2H-[1,2']bipyridinyl-5'-ylmethyl)-1H-imidazol-2-ylmethyl]-benzonitrile 4-[1-(3-Bromo-2-oxo-2H-[1,2']bipyridinyl-5'-ylmethyl)-1H-imidazol-2-ylmethyl]-benzonitrile 4-[1-(5-Bromo-2-oxo-2H-[1,2']bipyridinyl-5'-ylmethyl)-1H-imidazol-2-ylmethyl]-benzonitrile 4-[1-(5-Cyano-2-oxo-2H-[1,2']bipyridinyl-5'-ylmethyl)-1H-imidazol-2-ylmethyl]-benzonitrile 4-[1-(3,5-Dichloro-2-oxo-2H-[1,2']bipyridinyl-5'-ylmethyl)-1H-imidazol-2-ylmethyl]-benzonitrile (R,S) 4-{[3-(5-chloro-2-oxo-2H-[1,2']bipyridinyl-5'-ylmethyl)-3H-imidazol-4-yl]-hydroxy-methyl}-benzonitrile (R,S) 4-{[3-(5-chloro-2-oxo-2H-[1,2']bipyridinyl-5'-ylmethyl)-3H-imidazol-4]-yl -fluoro-methyl}-benzonitrile 4-[3-(5-Chloro-2-oxo-2H-[1,2']bipyridinyl-5'-ylmethyl)-3H-imidazole-4-carbonyl]-benzonitrile 4-{[3-(5-chloro-2-oxo-2H-[1,2']bipyridinyl-5'-ylmethyl)-3H-imidazol-4-yl]-methoxy-methyl}-benzonitrile (R,S) 4-[-(5-Chloro-2-oxo-2H-[1,2']bipyridinyl-5'-ylmethyl)-1H-imidazol-2-ylbutyloxy-methyl]-benzonitrile 4-[5-(5-chloro-2-oxo-2H-[1,2']bipyridinyl-5'-ylmethyl)-imidazol-1-ylmethyl]-benzonitrile 5'-(3-Benzyl-3H-imidazol-4-ylmethyl)-5-chloro-[1,2']bipyridinyl-2-one 5-Chloro-5'-(3-pyrazin-2-ylmethyl-3H-imidazol-4-ylmethyl)-[1,2']bipyridinyl-2-one 5-[5-(5-Chloro-2-oxo-2H-[1,2']bipyridinyl-5'-ylmethyl)-imidazol-1-ylmethyl]-furan-2-carbonitrile (R,S) Acetic acid (5-chloro-2-oxo-2H-[1,2']bipyridinyl-5'-yl)-[3-(4-cyano-benzyl)-3H-imidazol-4-yl]-methyl ester 4-{5-[(5-chloro-2-oxo-2H-[1,2']bipyridinyl-5'-yl)-hydroxy-methyl]-imidazol-1-ylmethyl}-benzonitrile (R,S) 4-{5-[(5-chloro-2-oxo-2H-[1,2']bipyridinyl-5'-yl)-methoxy-methyl]-imidazol-1-ylmethyl}-benzonitrile (R,S) 4-{5-[butoxy-(5-chloro-2-oxo-2H-[1,2']bipyridinyl-5'-yl)-methyl]-imidazol-1-ylmethyl}-benzonitrile 1-{4-[5-(4-Cyanophenyloxy)imidazol-1-ylmethyl]phenyl}-1H-pyridin-2-one 1-{4-[5-(4-Cyanophenyloxy-3-methoxy)imidazol-1-ylmethyl]phenyl}-1H-pyridin-2-one 4-[3-(5-chloro-2-oxo-2H-[1,2']bipyridinyl-5'-ylmethyl)-4,5,6,7-tetrahydro-3H-imidazo[4,5-c]pyridin-4-yl]-benzonitrile 2-(5-Chloro-2-oxo-2H-[1,2']bipyridinyl-5'-ylmethoxy)-4-imidazol-1-ylmethyl-benzonitrile 4-{3-[5-(5-Chloro-2-oxo-2H-pyridin-1-yl)-pyrazin-2-ylmethyl]-3H-imidazol-4-ylmethyl}-benzonitrile 2-(2-Amino-ethoxy)-4-[5-(5-chloro-2-oxo-2H-[1,2']bipyridinyl-5'-ylmethyl)-imidazol-1-ylmethyl]-benzonitrile 4-[5-(5-Chloro-2-oxo-2H-[1,2']bipyridinyl-5'-ylmethyl)-imidazol-1-ylmethyl]-2-(2-dimethylamino-ethoxy)-benzonitrile N-(2-{5-[5-(5-chloro-2-oxo-2H-[1,2']bipyridinyl-5'-ylmethyl)-imidazol-1-ylmethyl]-2-cyano-phenoxy}-ethyl)-acetamide 3-Chloro-N-(2-{5-[5-(5-chloro-2-oxo-2H-[1,2']bipyridinyl-5'-ylmethyl)-imidazol-1-ylmethyl]-2-cyano-phenoxy}-ethyl)-benzamide 4-[5-(5-Chloro-2-oxo-2H-[1,2']bipyridinyl-5'-ylmethyl)-
imidazol-1-ylmethyl]-2-(2,2,2-trifluoro-ethoxy)-
benzonitrile 2-Benzyloxy-4-[5-(5-chloro-2-oxo-2H-[1,2']bipyridinyl-
5'-ylmethyl)-imidazol-1-ylmethyl]-benzonitrile 4-[5-(5-Chloro-2-oxo-2H-[1,2']bipyridinyl-5'-ylmethyl)-
imidazol-1-ylmethyl]-2-phenethyloxy-benzonitrile 4-[5-(5-Chloro-2-oxo-2H-[1,2']bipyridinyl-5'-ylmethyl)-
imidazol-1-ylmethyl]-2-(4-phenyl-butoxy)-
benzonitrile 4-[5-(5-chloro-2-oxo-2H-[1,2']bipyridinyl-5'-ylmethyl)-
imidazol-1-ylmethyl]-2-(3-phenyl-propoxy)-
benzonitrile 4-[5-(5-Chloro-2-oxo-2H-[1,2']bipyridinyl-5'-ylmethyl)-
imidazol-1-ylmethyl]-2-methoxy-benzonitrile 5-[5-(5-Chloro-2-oxo-2H-[1,2']bipyridinyl-5'-ylmethyl)-
imidazol-1-ylmethyl]-biphenyl-2-carbonitrile 4-[5-(5-Chloro-2-oxo-2H-[1,2']bipyridinyl-5'-ylmethyl)-
imidazol-1-ylmethyl]-phthalonitrile 5-[5-(5-Chloro-2-oxo-2H-[1,2']bipyridinyl-5'-ylmethyl)-
imidazol-1-ylmethyl]-pyridine-2-carbonitrile 4-[3-(5-chloro-2-oxo-2H-[1,2']bipyridinyl-5'-ylmethyl)-
3H-imidazol-4-ylmethyl]-2-methoxy-benzonitrile 4-[3-(5-chloro-2-oxo-2H-[1,2']bipyridinyl-5'-ylmethyl)-
3H-imidazol-4-ylmethyl]-phthalonitrile 5-[5-(5-chloro-2-oxo-2H-[1,2']bipyridinyl-5'-ylmethyl)-
imidazol-1-ylmethyl]-2-methoxy-benzonitrile 4-[3-(5-chloro-2-oxo-2H-[1,2']bipyridinyl-5'-ylmethyl)-
3H-imidazol-4-ylmethyl]-biphenyl-2-carbonitrile 5-[3-(5-chloro-2-oxo-2H-[1,2']bipyridinyl-5'-ylmethyl)-
3H-imidazol-4-ylmethyl]-biphenyl-2-carbonitrile 5-chloro-5'-[5-(4-[1,2,3]thiadiazol-4-yl-benzyl)-
imidazol-1-ylmethyl]-[1,2']bipyridinyl-2-one 4-{3-[(5-chloro-2-oxo-2H-[1,2']bipyridinyl-5'-ylmethyl)-
amino]-1-imidazol-1-yl-propyl}-benzonitrile 2-Methoxy-4-{3-[4-(2-oxo-2H-pyridin-1-yl)-benzyl]-
3H-imidazol-4-ylmethyl}-benzonitrile 4-[3-(5-chloro-2-oxo-2H-[1,2']bipyridinyl-5'-ylmethyl)-
3H-imidazol-4-ylmethyl]-2-(2,2,2-trifluoro-ethoxy)-
benzonitrile or the pharmaceutically acceptable salts thereof.

Specific examples of the compounds of the invention are:

4-[1-(5-Chloro-2-oxo-2H-[1,2']bipyridinyl-5'-ylmethyl)-
1H-imidazol-2-ylmethyl]-benzonitrile

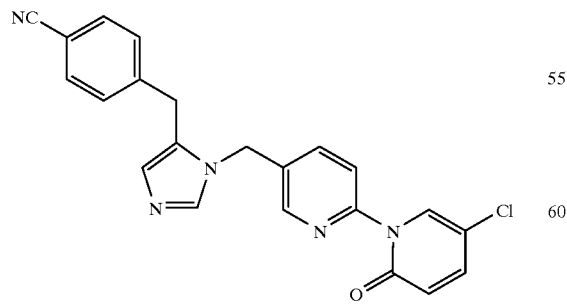

4-[1-(5-Bromo-2-oxo-2H-[1,2']bipyridinyl-5'-ylmethyl)-
1H-imidazol-2-ylmethyl]-benzonitrile

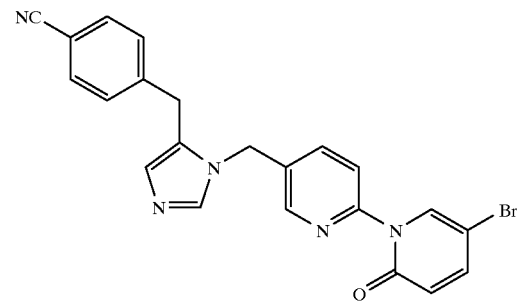

4-[5-(5-chloro-2-oxo-2H-[1,2']bipyridinyl-5'-ylmethl]-benzonitrile

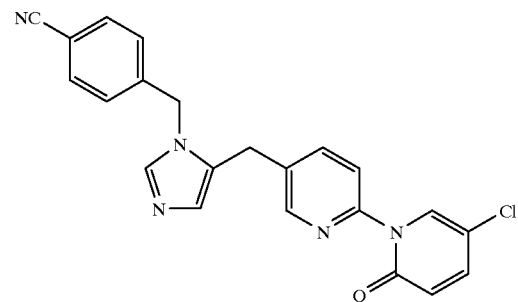

5-[5-(5-Chloro-2-oxo-2H-[1,2']bipyridinyl-5'-ylmethyl)-
imidazol-1-ylmethyl]-pyridine-2-carbonitrile

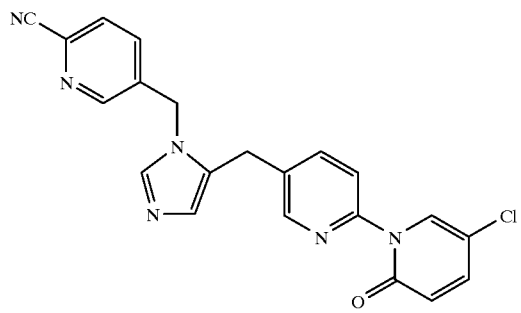

4-{3-[5-(5-Chloro-2-oxo-2H-pyridin-1-yl)-pyrazin-2-
ylmethyl]-3H-imidazol-4-ylmethyl}-benzonitrile

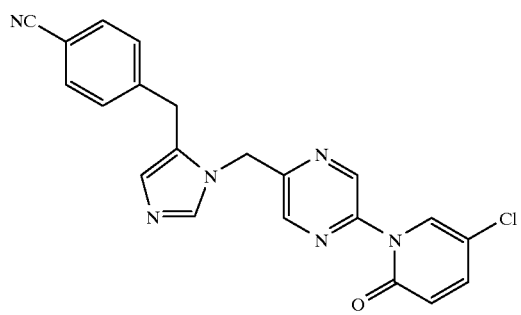

4-[3-(5-chloro-2-oxo-2H-[1,2']bipyridinyl-5'-ylmethyl)-
3H-imidazol-4-ylmethyl]-2-methoxy-benzonitrile

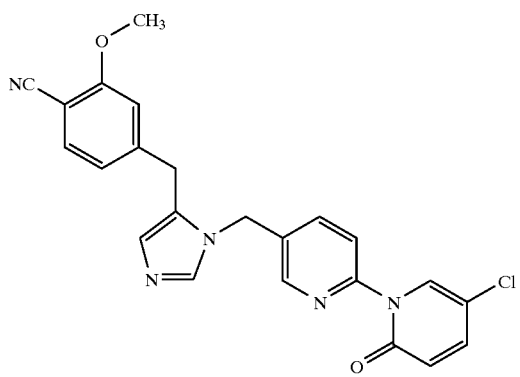

or a pharmaceutically acceptable salt thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aroyl and aralkyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and 4,5,6,7-tetrahydro-3H-imidazo[4,5-c]pyridin-4-yl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^3$, $R^4$, $R^5$ and $R^{6a-e}$, the term "the substituted group" is intended to mean a substituted $C_{1-8}$ alkyl, substituted $C_{2-8}$ alkenyl, substituted $C_{2-8}$ alkynyl, substituted aryl or substituted heterocycle from which the substituent(s) $R^3$, $R^4$, $R^5$ and $R^{6a-e}$ are selected.

As used herein in the definition of $R^7$, the substituted $C_{1-8}$ alkyl, substituted $C_{3-6}$ cycloalkyl, substituted aroyl, substituted aryl, substituted heteroaroyl, substituted arylsulfonyl, substituted heteroaryl-sulfonyl and substituted heterocycle include moieties containing from 1 to 3 substituents in addition to the point of attachment to the rest of the compound.

As used herein, when no specific substituents are set forth, the terms "substituted aryl", "substituted heterocycle" and "substituted cycloalkyl" are intended to include the cyclic group which is substituted on a substitutable ring carbon atom with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl)O—, —OH, $(C_1-C_6$ alkyl)S(O)$_m$—, $(C_1-C_6$ alkyl)C(O)NH—, $H_2N$—C(NH)—, $(C_1-C_6$ alkyl)C(O)—, $(C_1-C_6$ alkyl)OC(O)—, $N_3$, $(C_1-C_6$ alkyl)OC(O)NH—, phenyl, pyridyl, imidazolyl, oxazolyl, isoxazolyl, thiazolyl, thienyl, furyl, isothiazolyl and $C_1-C_{20}$ alkyl.

Lines drawn into the ring systems from substituents (such as from $R^3$, $R^4$, Q etc.) means that the indicated bond may be attached to any of the substitutable ring carbon or nitrogen atoms.

The substituent illustrated by the structure

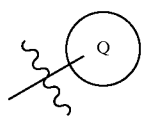

represents a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y and includes the following ring systems:

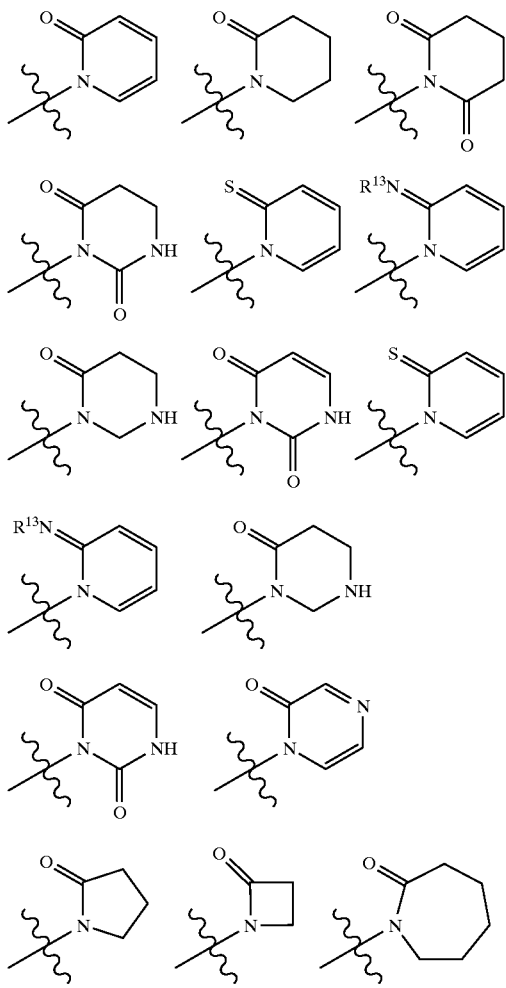

Preferably, the structure

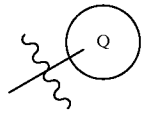

is selected from:

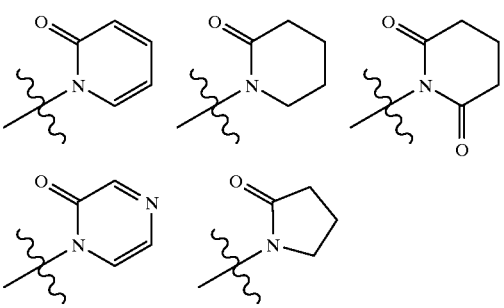

Most preferably, Q is

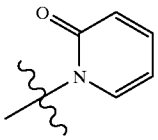

It is understood that such rings may be substituted by R$^{6a}$, R$^{6b}$, R$^{6c}$, R$^{6d}$ and/or R$^{6e}$ as defined hereinabove.

The moiety described as

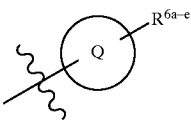

where any two of R$^{6a}$, R$^{6b}$, R$^{6c}$, R$^{6d}$ and R$^{6e}$ on adjacent carbon atoms are combined to form a diradical selected from —CH=CH—CH=CH—, —CH=CH—CH—, —(CH$_2$)$_4$— and —(CH$_2$)$_4$— includes, but is not limited to, the following structures:

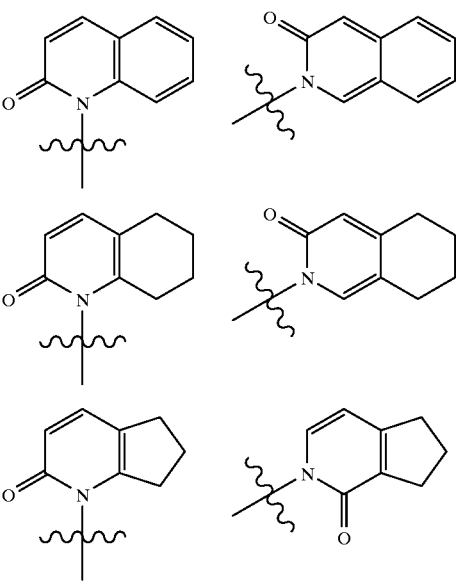

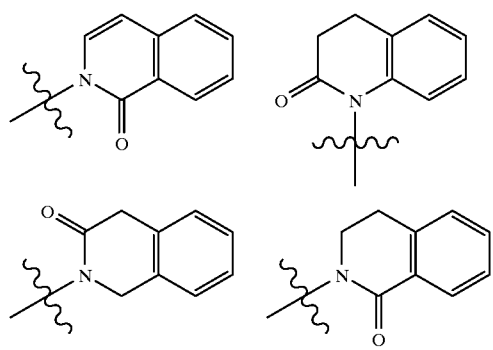

It is understood that such fused ring moieties may be further substituted by the remaining $R^{6a}$, $R^{6b}$, $R^{6c}$, $R^{6d}$ and/or $R^{6e}$ as defined hereinabove.

The substituent illustrated by the structure

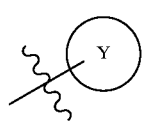

represents a 5, 6 or 7 membered carbocyclic ring wherein from 0 to 3 carbon atoms are replaced by a heteroatom selected from N, S and O, and wherein Y is attached to Q through a carbon atom and includes the following ring systems:

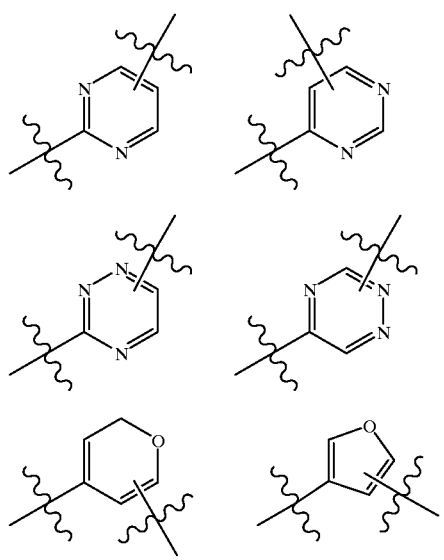

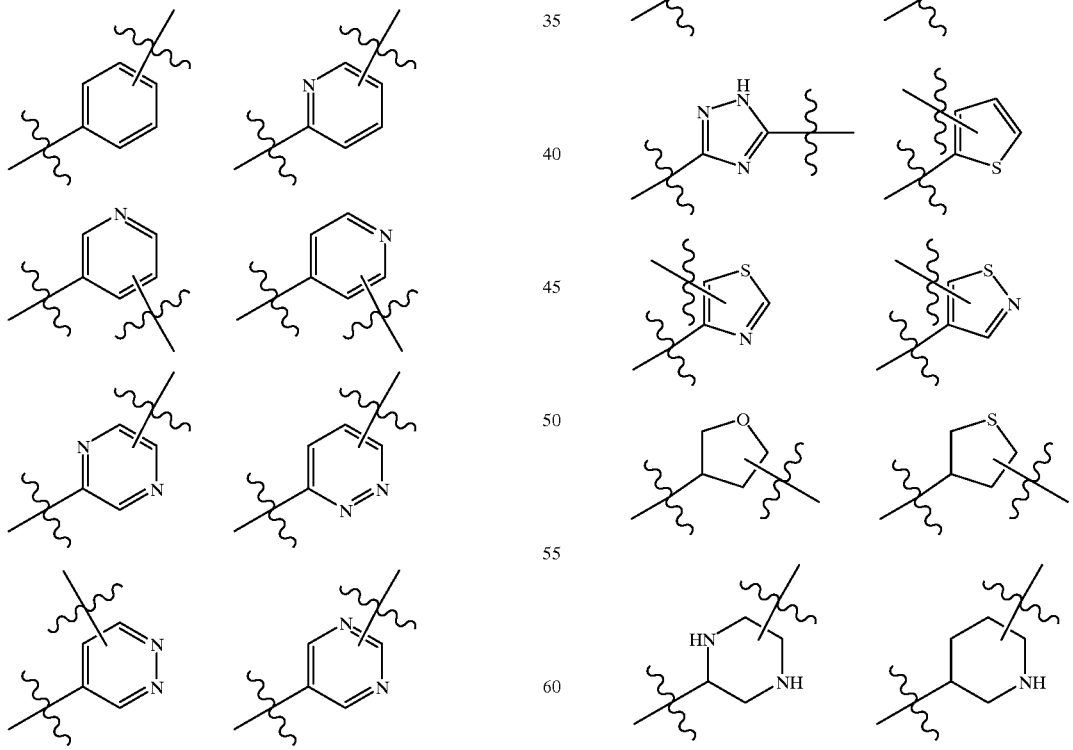

-continued

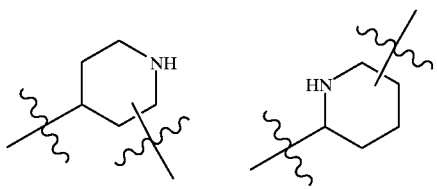

Preferably Y is the moiety designated by the following structure

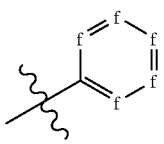

which represents an aromatic 6-membered ring and includes the following ring systems:

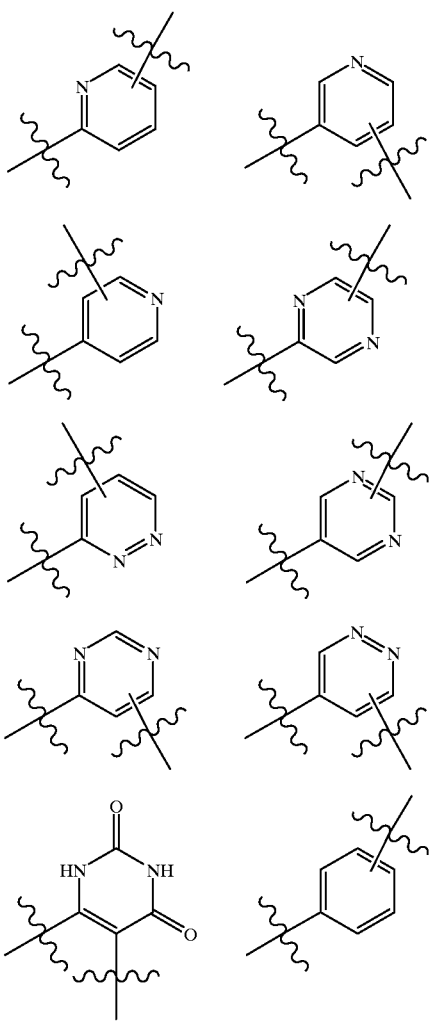

wherein it is understood that one of the ring carbon atoms is substituted with Q. Preferably, the Y is selected from phenyl and pyridyl.

More preferably Y is the moiety designated by the following structure

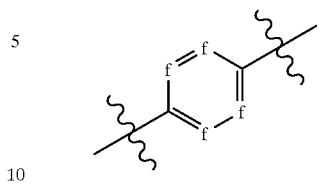

which represents an aromatic 6-membered ring and includes the following ring systems:

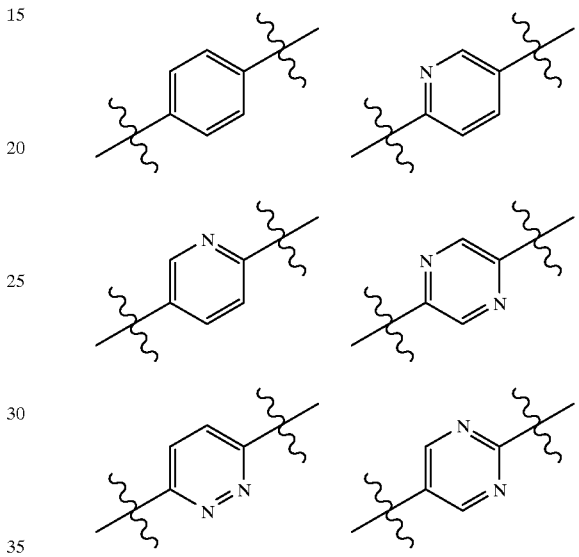

Preferably, the Y is selected from phenyl, pyrazine and pyridyl.

Preferably, $R^1$ and $R^2$ are independently selected from: hydrogen, $R^{11}C(O)O-$, $-N(R^{10})_2$, $R^{10}C(O)NR^{10}-$, $R^{10}O-$ or unsubstituted or substituted $C_1-C_6$ alkyl wherein the substituent on the substituted $C_1-C_6$ alkyl is selected from unsubstituted or substituted phenyl, $-N(R^{10})_2$, $R^{10}O-$ and $R^{10}C(O)NR^{10}-$.

Preferably, $R^3$ is selected from:
  a) hydrogen,
  b) $C_3-C_{10}$ cycloalkyl, halogen, $C_1-C_6$ perfluoroalkyl, $R^{12}O-$, CN, $NO_2$, $R^{10}C(O)-$ or $-N(R^{10})_2$,
  c) unsubstituted $C_1-C_6$ alkyl,
  d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}_2N-C(NR^{10})-$, CN, $R^{10}C(O)-$, $N_3$, $-N(R^{10})_2$, and $R^{11}OC(O)-NR^{10}-$.

Preferably, $R^4$ is selected from: hydrogen, halogen, trifluoromethyl, trifluoromethoxy and $C_1-C_6$ alkyl.

Preferably, $R^5$ is hydrogen.

Preferably, $R^{6a}$, $R^{6b}$, $R^{6c}$, $R^{6d}$ and $R^{6e}$ are independently selected from:
  a) hydrogen,
  b) $C_3-C_{10}$ cycloalkyl, halogen, $C_1-C_6$ perfluoroalkyl, $R^{12}O-$, $R^{11}S(O)_m-$, CN, $NO_2$, $R^{10}C(O)-$ or $-N(R^{10})_2$,
  c) unsubstituted $C_1-C_6$ alkyl;

d) substituted $C_1-C_6$ alkyl wherein the substituent on the substituted $C_1-C_6$ alkyl is selected from unsubstituted or substituted aryl, $C_3-C_{10}$ cycloalkyl, $R^{12}O-$, $R^{11}S(O)_m-$, $R^{10}C(O)-$ or $-N(R^{10})_2$.

Preferably, $R^8$ is independently selected from:
a) hydrogen, and
b) aryl, substituted aryl, heterocycle, substituted heterocycle, $C_1-C_6$ perfluoroalkyl, $R^{10}O-$ or CN.

Preferably, $R^9$ is hydrogen, halogen or methyl.

Preferably, $R^{10}$ is independently selected from hydrogen, $C_1-C_6$ alkyl, benzyl, 2,2,2-trifluoroethyl, aryl and substituted aryl. More preferably, $R^{10}$ is selected from H, $C_1-C_6$ alkyl and benzyl.

Preferably, $A^1$ and $A^2$ are independently selected from: a bond, $-C(O)NR^{10}-$, $-NR^{10}C(O)-$, O, $-N(R^{10})-$, $-S(O)_2N(R^{10})-$ and $-N(R^{10})S(O)_2-$.

Preferably, V is selected from hydrogen, heterocycle and aryl. More preferably, V is phenyl and pyridyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, n and r are independently 0, 1, or 2.
Preferably s is 0.
Preferably t is 1.
Preferably, the moiety

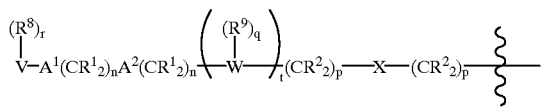

is selected from:

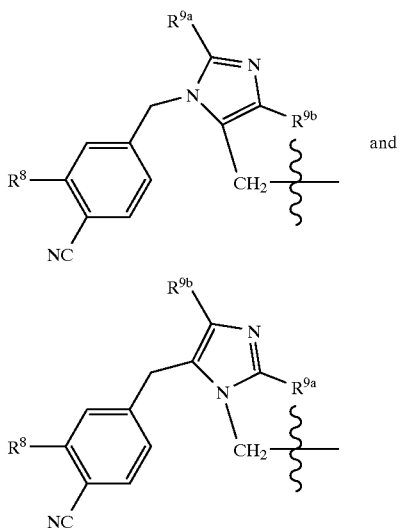

and

It is intended that the definition of any substituent or variable (e.g., $R^1$, $R^2$, $R^9$, n, etc.) at a particular location in a molecule be independent of its definitions elsewhere in that molecule. Thus, $-N(R^{10})_2$ represents $-NHH$, $-NHCH_3$, $-NHC_2H_5$, etc. It is understood that substituents and substitution patterns on the compounds of the instant invention can be selected by one of ordinary skill in the art to provide compounds that are chemically stable and that can be synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–19, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heterocyclic moieties contain multiple substituents.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein.

Synopsis of Schemes 1–19:

The requisite intermediates are in some cases commercially available, or can be prepared according to literature procedures. Schemes 1–11 illustrate synthesis of the instant bicyclic compounds which incorporate a preferred benzylimidazolyl side chain. Thus, in Scheme 1, for example, a bicyclic intermediate that is not commercially available may be synthesized by methods known in the art. Thus, a suitably substituted pyridinone 1 may be reacted under coupling conditions with a suitably substituted iodobenzyl alcohol to provide the intermediate alcohol 2. The intermediate alcohol 2 may converted to the corresponding bromide 3. The bromide 3 may be coupled to a suitably substituted benzylimidazolyl 4 to provide, after deprotection, the instant compound 5.

Schemes 2–4 illustrate methods of synthesizing related or analogous key alcohol intermediates, which can then be processed as described in Scheme 1. Thus, Scheme 2 illustrates pyridinonyl-pyridyl alcohol forming reactions starting with the suitably substituted iodonicotinate 6.

Scheme 3 illustrates preparation of the intermediate alcohol 9 wherein the terminal lactam ring is saturated. Acylation of a suitably substituted 4-aminobenzyl alcohol 7 with a suitably substituted brominated acyl chloride provides the bisacylated intermediate 8. Closure of the lactam ring followed by saponifiaction of the remaining acyl group provides the intermediate alcohol. Preparation of the homologous saturated lactam 10 is illustrated in Scheme 4.

Scheme 5 illustrates the synthesis of the alcohol intermediate 13 which incorporates a terminal pyrazinone moiety. Thus, the amide of a suitably substituted amino acid 11 is formed and reacted with glyoxal to form the pyrazine 12, which then undergoes the Ullmann coupling to form intermediate 13.

Scheme 6 illustrates synthesis of an instant compound wherein a non-hydrogen $R^{9b}$ is incorporated in the instant compound. Thus, a readily available 4-substituted imidazole 14 may be selectively iodinated to provide the 5-iodoimidazole 15. That imidazole may then be protected and coupled to a suitably substituted benzyl moiety to provide intermediate 16. Intermediate 16 can then undergo the alkylation reactions that were described hereinabove.

Scheme 7 illustrates synthesis of instant compounds that incorporate a preferred imidazolyl moiety connected to the bicyclic moiety via an alkyl amino, sulfonamide or amide linker. Thus, the 4-aminoalkylimidazole 17, wherein the primary amine is protected as the phthalimide, is selectively alkylated then deprotected to provide the amine 18. The amine 18 may then react under conditions well known in the art with various activated bicyclic moieties to provide the instant compounds shown.

Compounds of the instant invention wherein the $A^1(CR^1_2)_n A^2(CR^1_2)_n$ linker is oxygen may be synthesized by methods known in the art, for example as shown in Scheme 8. The suitably substituted phenol 19 may be reacted with methyl N-(cyano)methanimidate to provide the 4-phenoxyimidazole 20. After selective protection of one of the imidazolyl nitrogens, the intermediate 21 can undergo alkylation reactions as described for the benzylimidazoles hereinabove.

Compounds of the instant invention wherein the $A^1(CR^1_2)_n A^2(CR^1_2)_n$ linker is a substituted methylene may be synthesized by the methods shown in Scheme 9. Thus, the N-protected imidazolyl iodide 22 is reacted, under Grignard conditions with a suitably protected benzaldehyde to provide the alcohol 23. Acylation, followed by the alkylation procedure illustrated in the Schemes above (in particular, Scheme 1) provides the instant compound 24. If other $R^1$ substituents are desired, the acetyl moiety can be manipulated as illustrated in the Scheme.

Scheme 10 illustrates incorporation of an acetyl moiety as the $(CR^2_2)_p X(CR^2_2)_p$ linker of the instant compounds. Thus the readily available methylphenone 25 undergoes the Ullmann reaction and the acetyl is brominated to provide intermediate 26. Reaction with the imidazolyl reagent 4 provides, after deprotection, the instant compound 27.

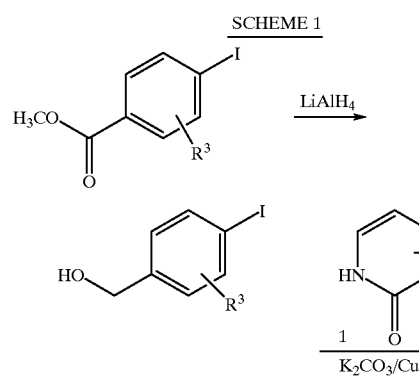

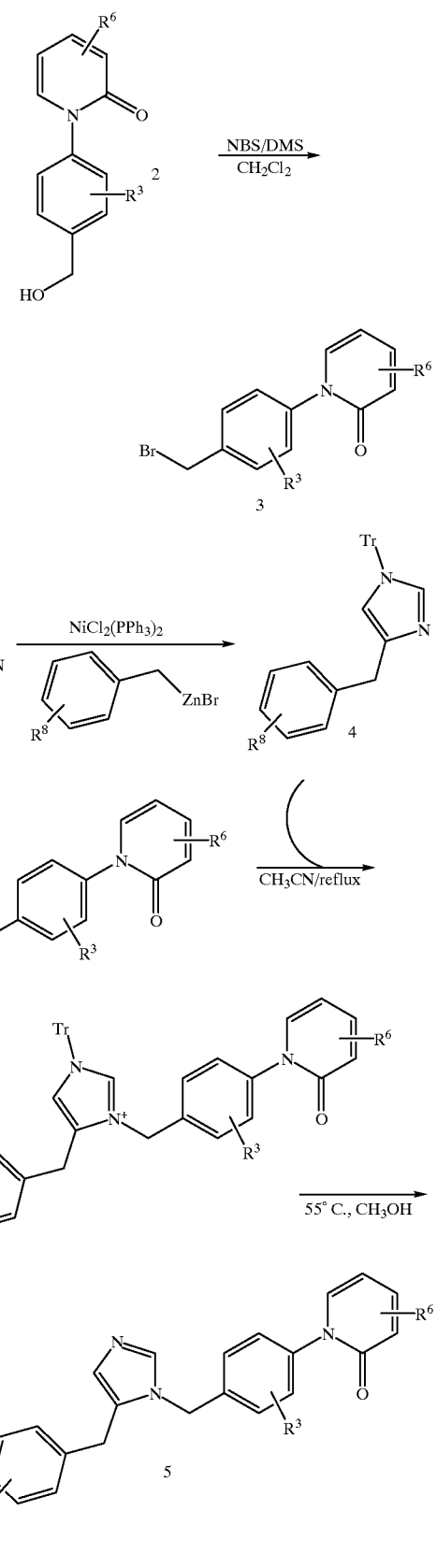

SCHEME 2
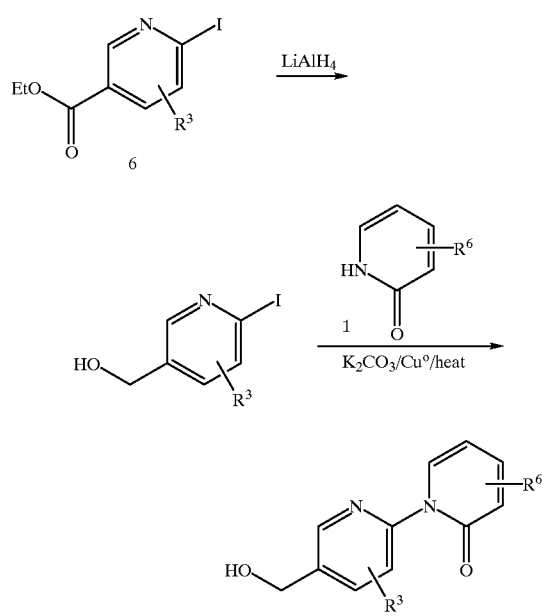
SCHEME 3
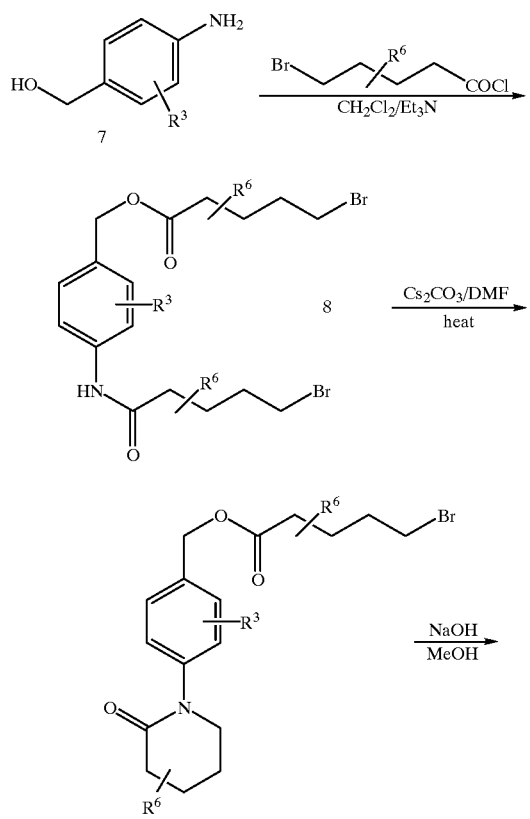
SCHEME 4
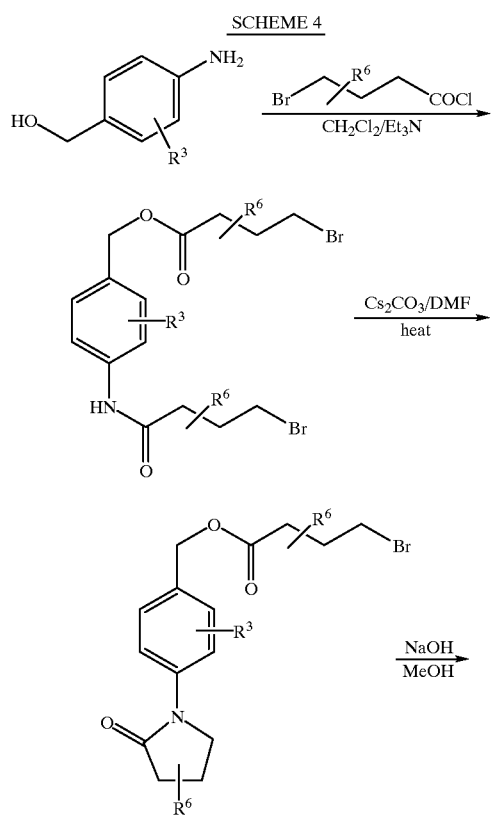

SCHEME 5
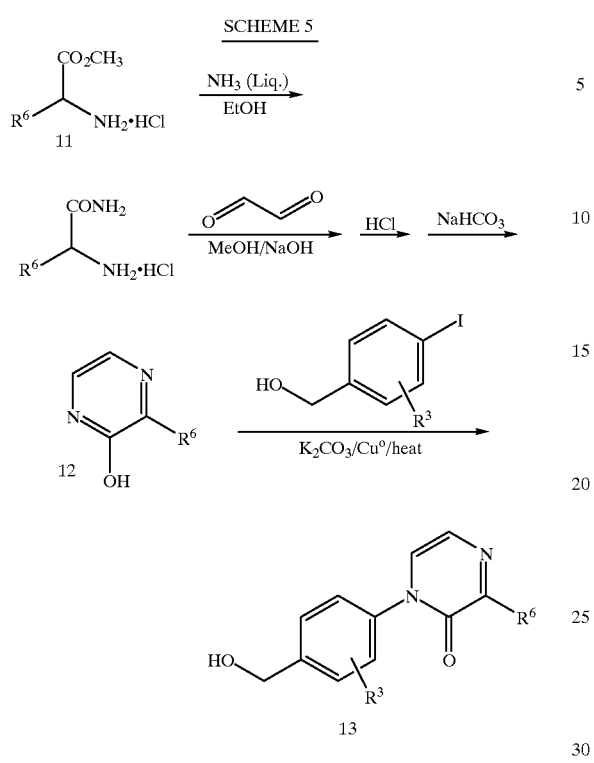
SCHEME 6
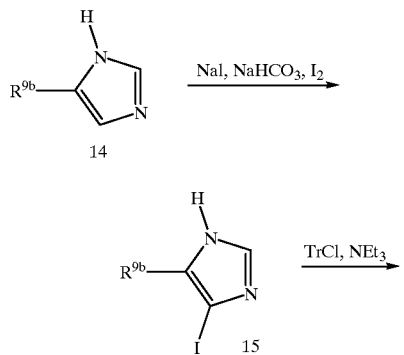
-continued
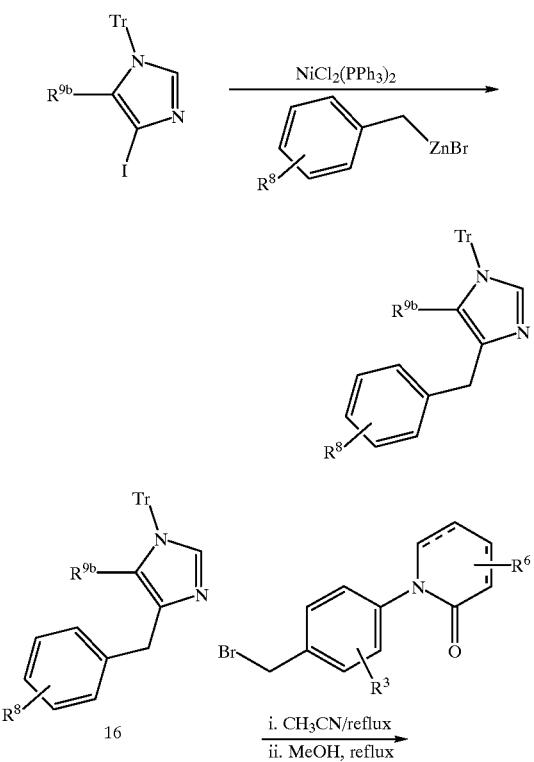
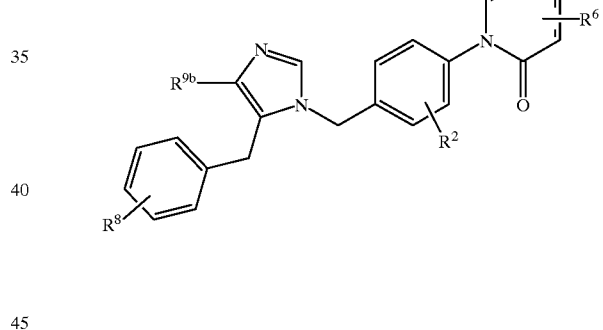

SCHEME 7
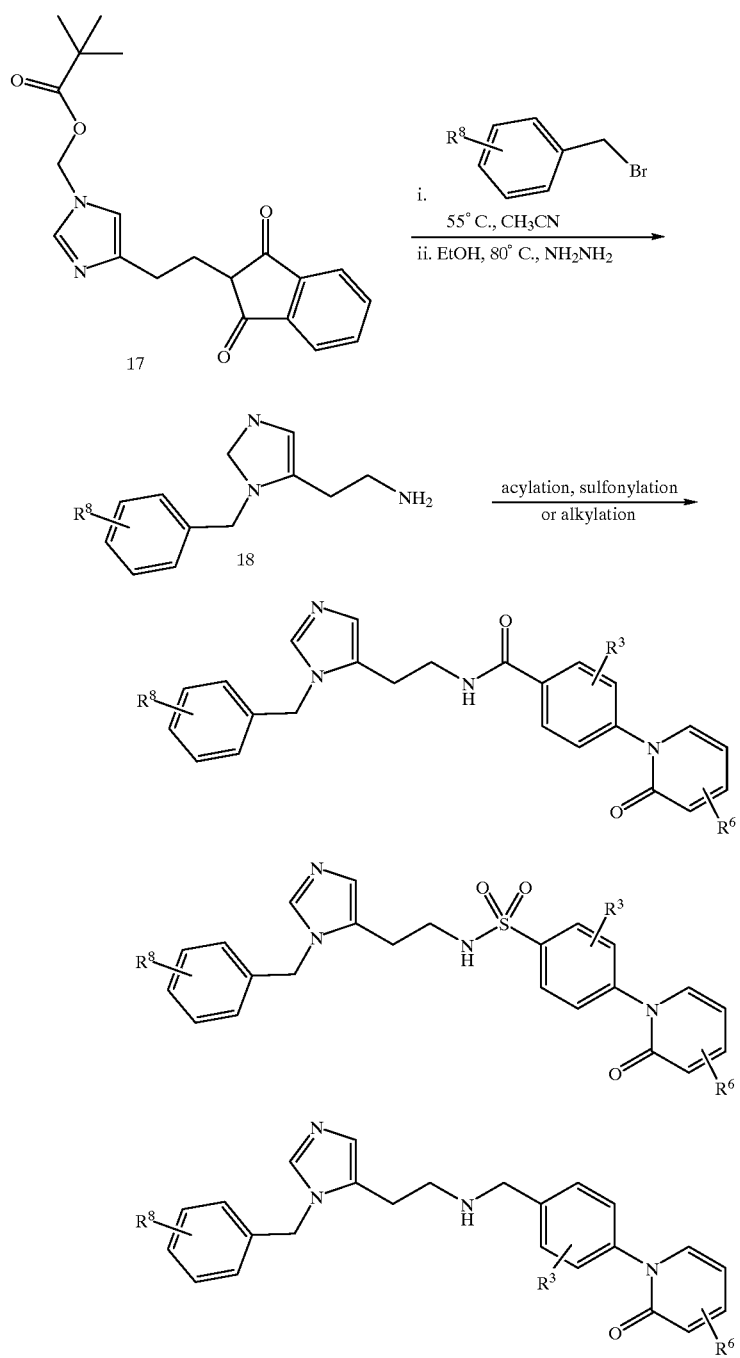
SCHEME 8
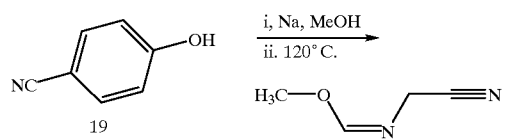

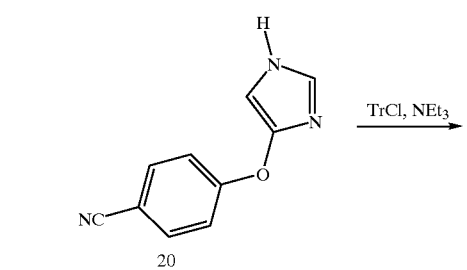
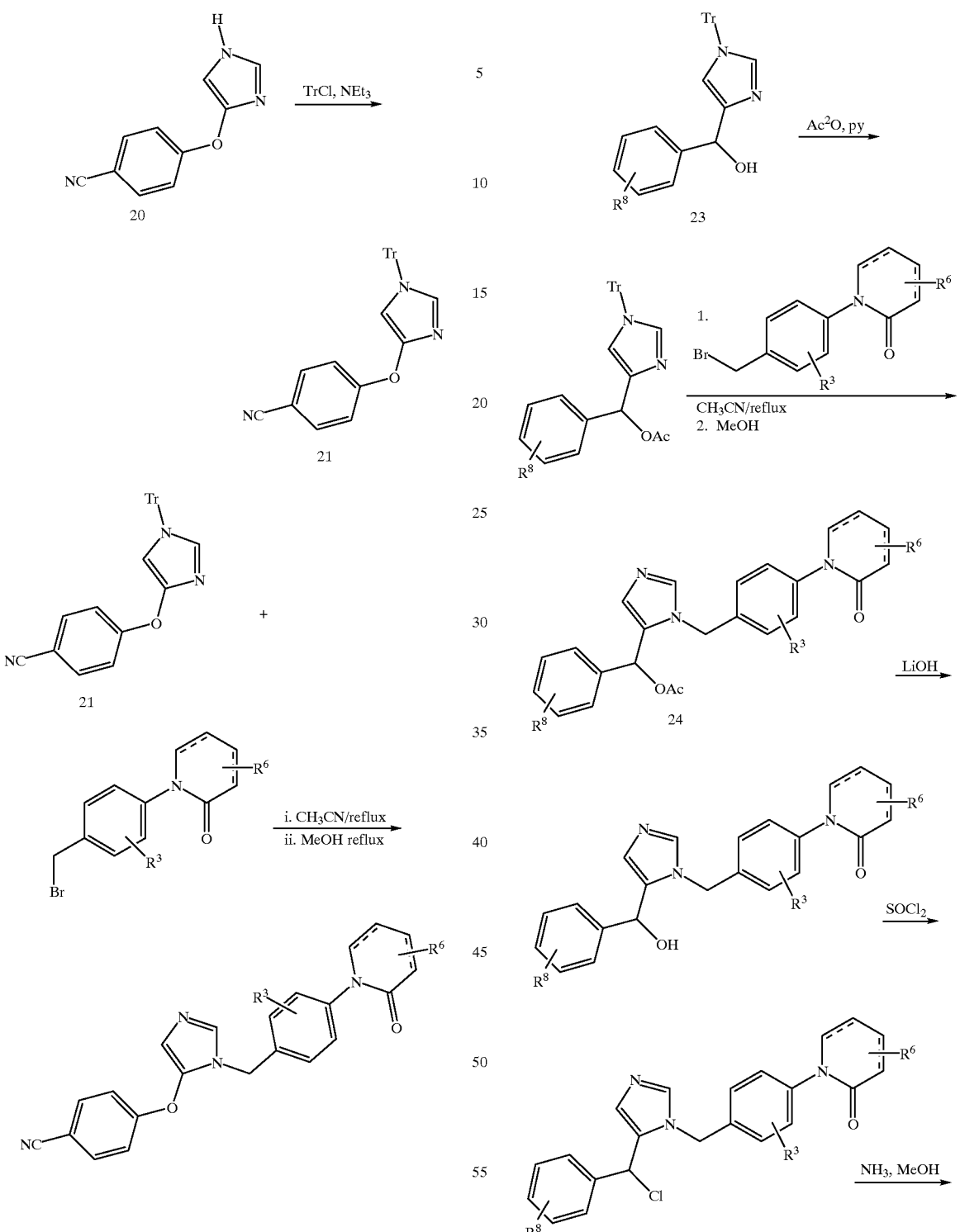
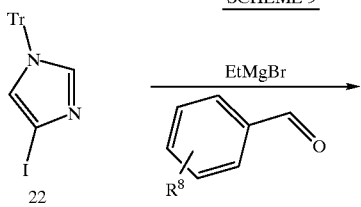

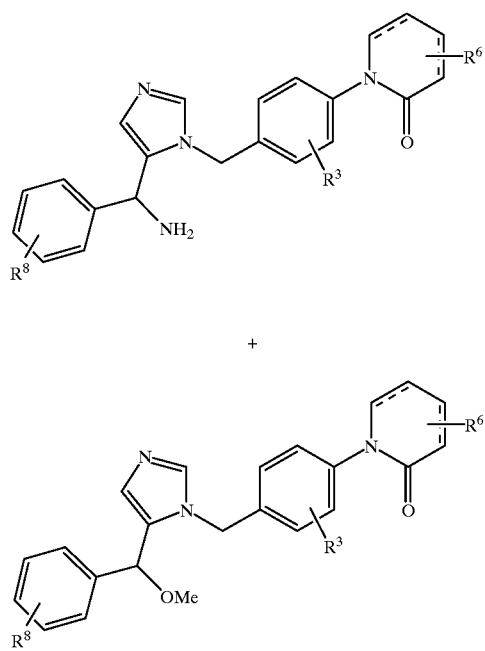

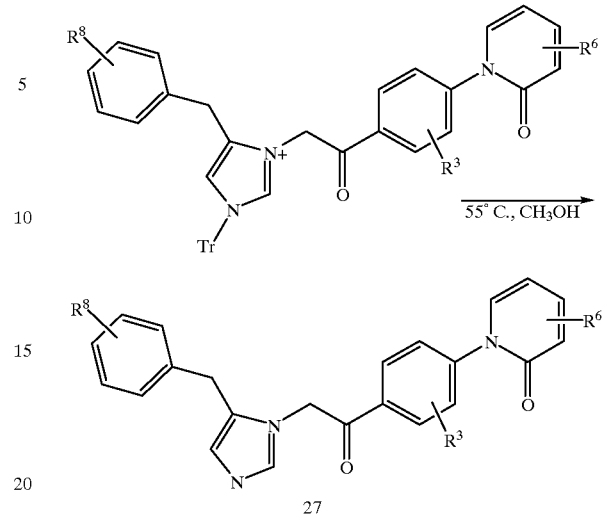

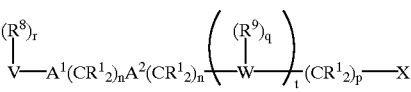

Schemes 11–19 illustrate reactions whrein the moiety $$V-A^1(CR^1{}_2)_nA^2(CR^1{}_2)_n\left(-W-\right)_t(CR^1{}_2)_p-X$$

incorporated in the compounds of the instant invention is represented by other than a substituted imidazole-containing group.

Thus, the intermediates whose synthesis are illustrated in Schemes hereinabove and other arylheteroaryl intermediates obtained commercially or readily synthesized, can be coupled with a variety of aldehydes. The aldehydes can be prepared by standard procedures, such as that described by O. P. Goel, U. Krolls, M. Stier and S. Kesten in *Organic Syntheses*, 1988, 67, 69–75, from the appropriate amino acid. Knochel chemistry may be utilized, as shown in Scheme 11, to incorporate the arylpyridinone moiety. Thus, a suitably substituted 4-(bromo)iodobenzene is coupled to a suitably substituted pyridinone 1 as previously described above. The resulting bromide 28 is treated with zinc(0) and the zinc bromide reagent 29 is reacted with an aldehyde to provide the C-alkylated instant compound 30. Compound 30 can be deoxygenated by methods known in the art, such as a catalytic hydrogention, then deprotected with trifluoroacetic acid in methylene chloride to give the final compound 31. The compound 31 may be isolated in the salt form, for example, as a trifluoroacetate, hydrochloride or acetate salt, among others. The product diamine 31 can further be selectively protected to obtain 32, which can subsequently be reductively alkylated with a second aldehyde to obtain 33. Removal of the protecting group, and conversion to cyclized products such as the dihydroimidazole 34 can be accomplished by literature procedures.

If the arylpyridinone zinc bromide reagent is reacted with an aldehyde which also has a protected hydroxyl group, such as 35 in Scheme 12, the protecting groups can be subse-

SCHEME 10

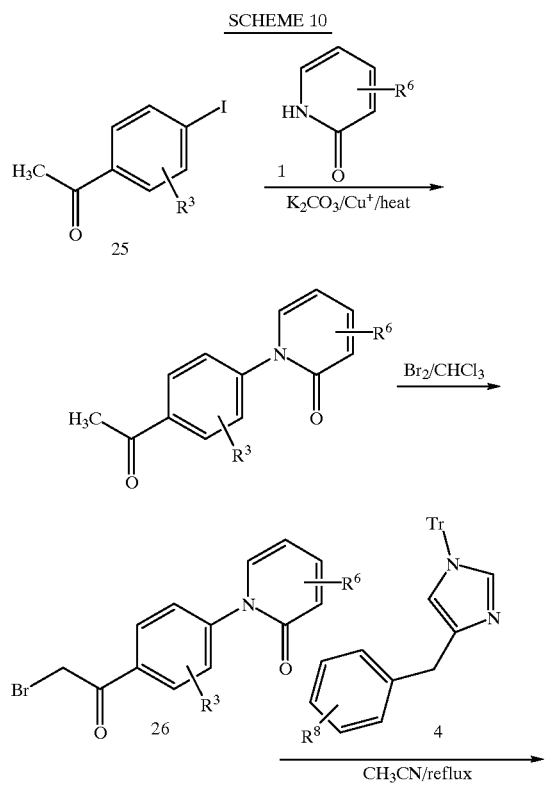

quently removed to unmask the hydroxyl group (Schemes 12, 13). The alcohol can be oxidized under standard conditions to e.g. an aldehyde, which can then be reacted with a variety of organometallic reagents such as alkyl lithium reagents, to obtain secondary alcohols such as 37. In addition, the fully deprotected amino alcohol 38 can be reductively alkylated (under conditions described previously) with a variety of aldehydes to obtain secondary amines, such as 39 (Scheme 13), or tertiary amines.

The Boc protected amino alcohol 36 can also be utilized to synthesize 2-aziridinylmethylarylpyridinone such as 40 (Scheme 14). Treating 36 with 1,1'-sulfonyldiimidazole and sodium hydride in a solvent such as dimethylformamide led to the formation of aziridine 40. The aziridine is reacted with a nucleophile, such as a thiol, in the presence of base to yield the ring-opened product 41.

In addition, the arylpyridinone subunit reagent can be reacted with aldehydes derived from amino acids such as O-alkylated tyrosines, according to standard procedures, to obtain compounds such as 43, as shown in Scheme 15. When R' is an aryl group, 43 can first be hydrogenated to unmask the phenol, and the amine group deprotected with acid to produce 44. Alternatively, the amine protecting group in 43 can be removed, and O-alkylated phenolic amines such as 45 produced.

Schemes 16–19 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

SCHEME 11

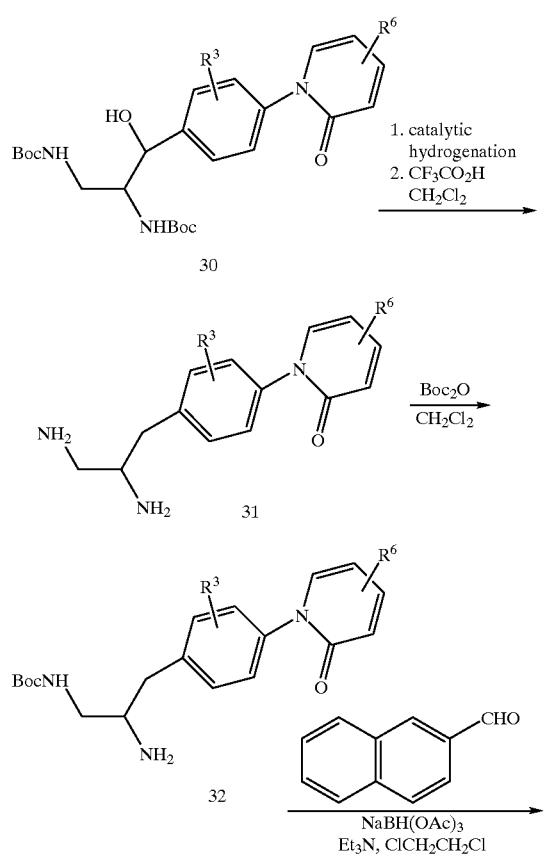

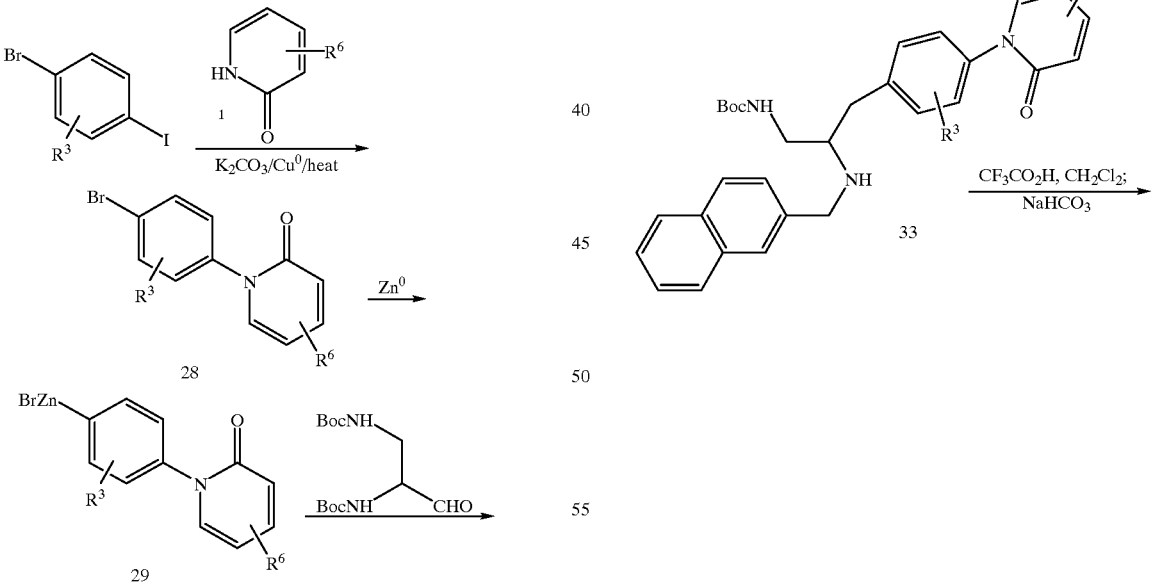

-continued
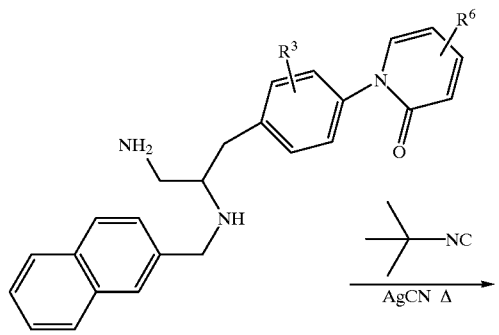
34
SCHEME 12
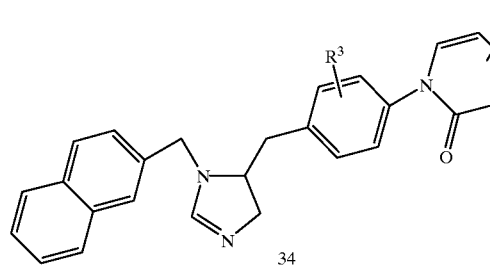
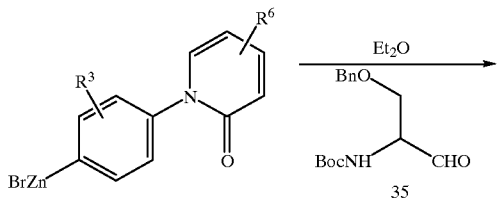
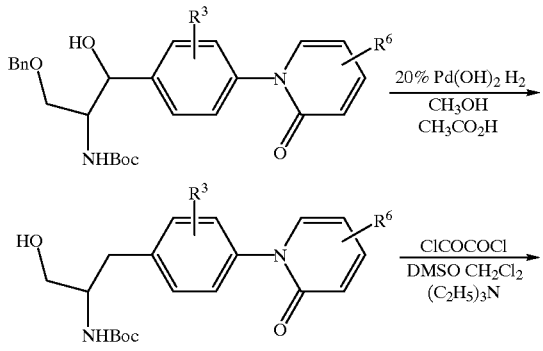
36
-continued
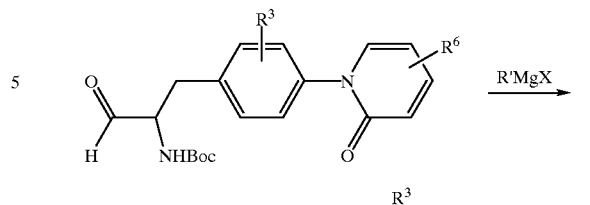
37
SCHEME 13
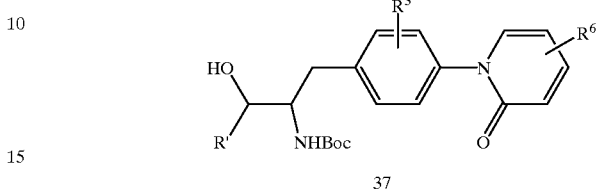
37
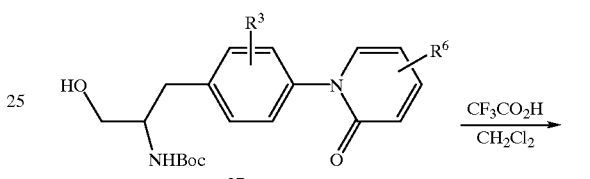
38
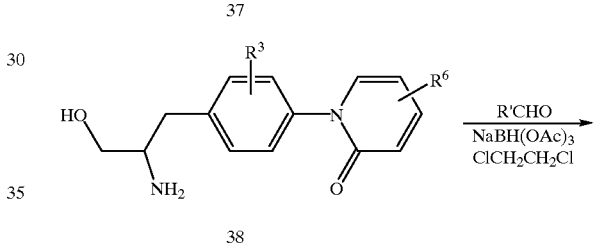
39
SCHEME 14
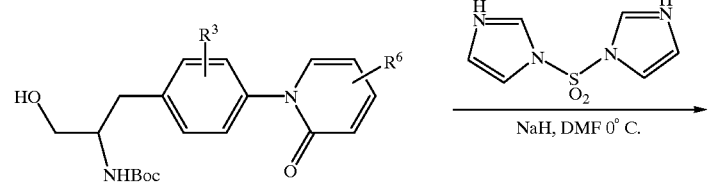
36

-continued
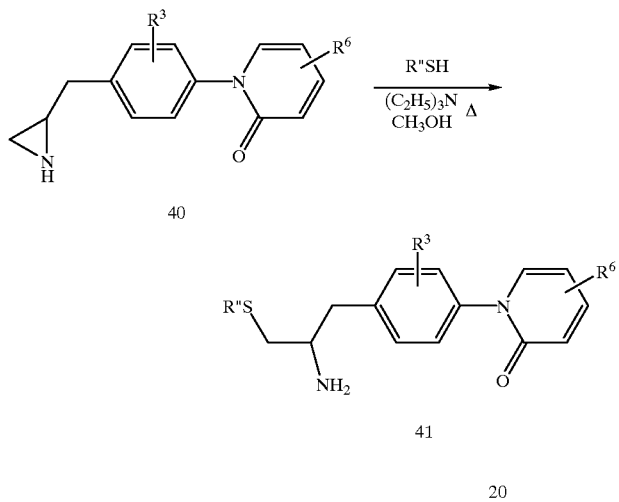
SCHEME 15
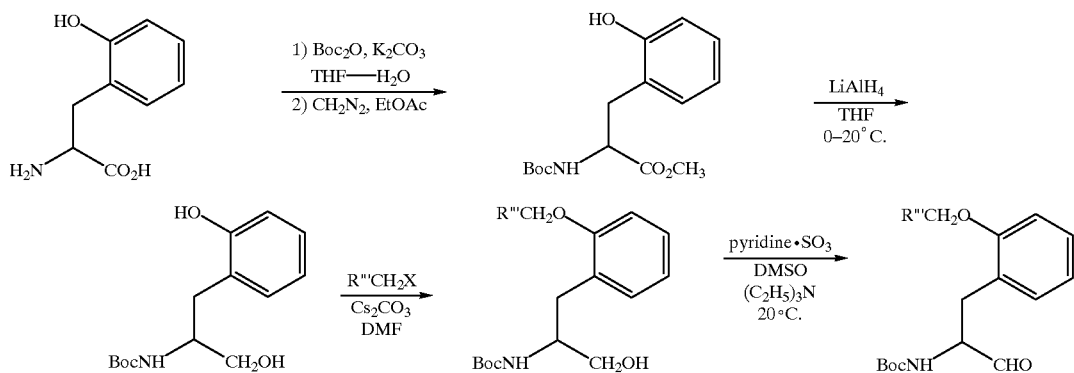

51                                    52
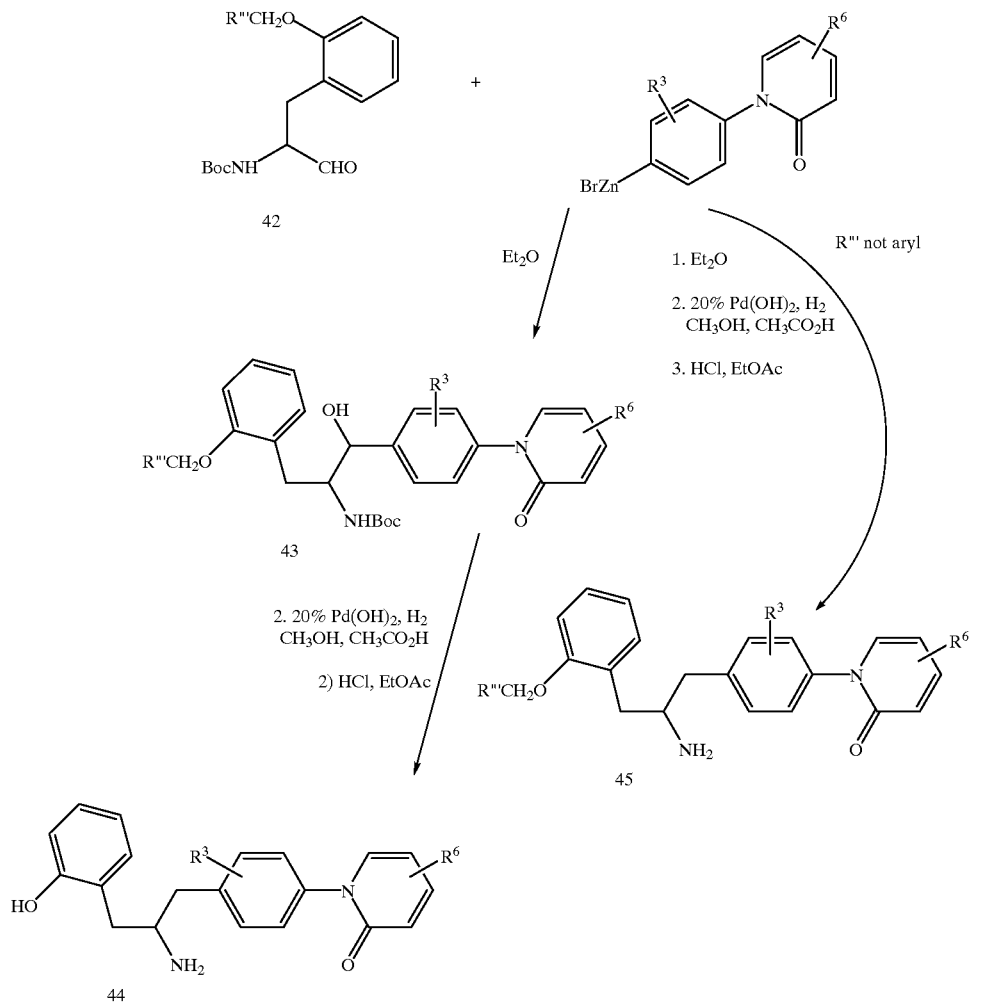
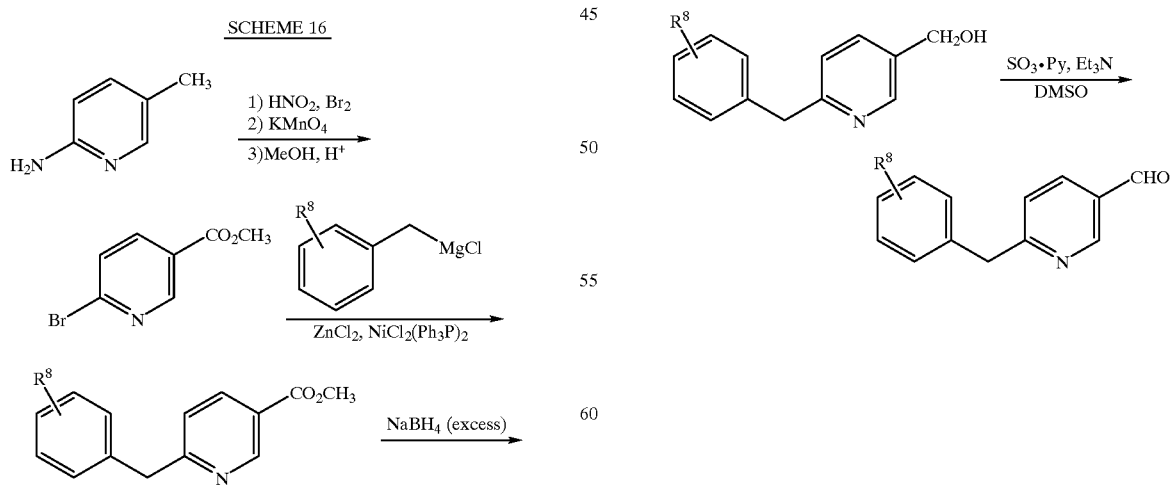
SCHEME 16

SCHEME 17
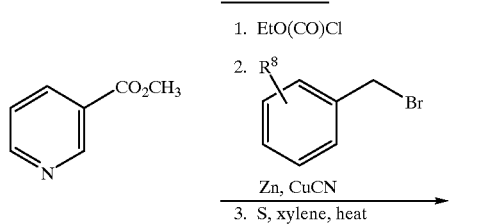
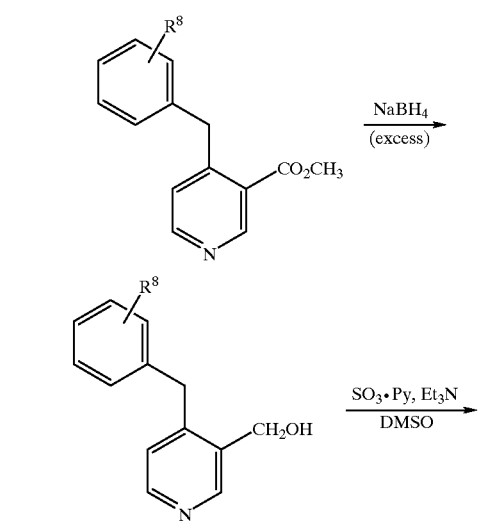
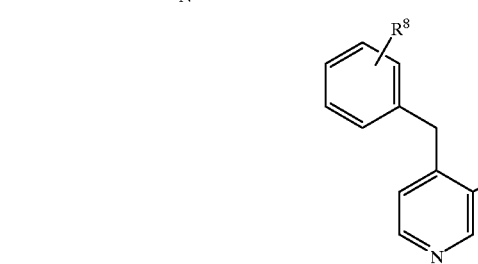
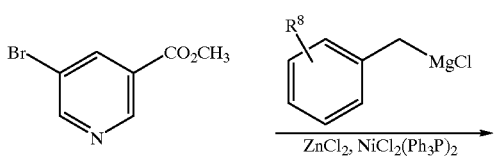
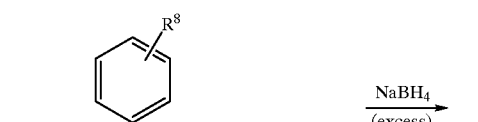
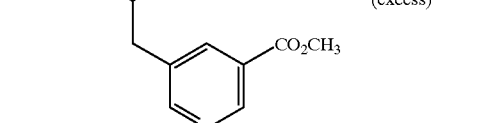
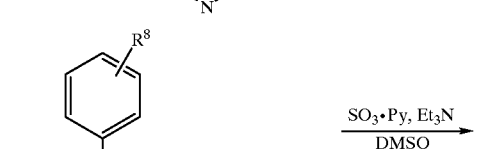
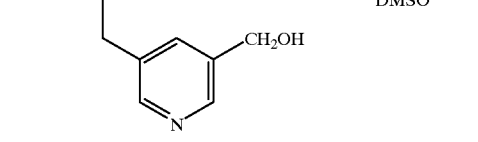
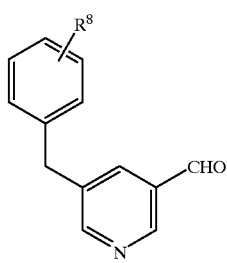
SCHEME 18
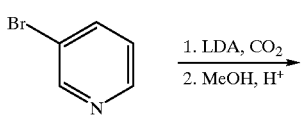
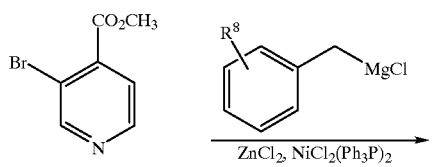
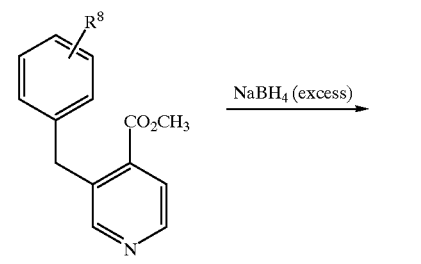
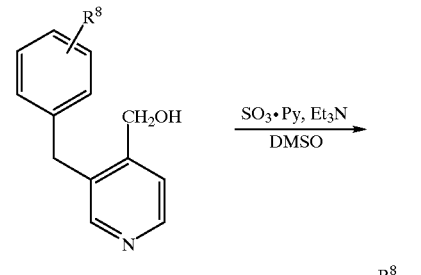
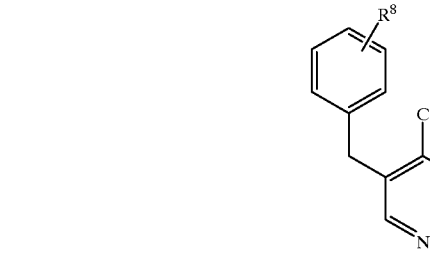

SCHEME 19

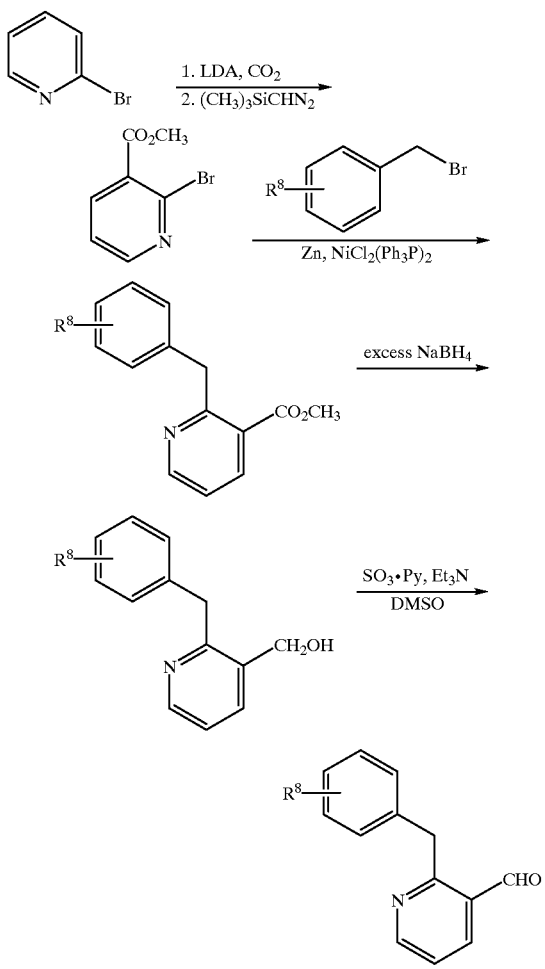

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. Cancer Research, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. Science, 256:1331–1333 (1992)).

The compounds of the instant invention are also useful in the prevention of restenosis after percutaneous transluminal coronary angioplasty by inhibiting neointimal formation (C. Indolfi et al. Nature medicine, 1:541–545(1995)).

The instant compounds may also be useful in the treatment and prevention of polycystic kidney disease (D. L. Schaffner et al. American Journal of Pathology, 142:1051–1060 (1993) and B. Cowley, Jr. et al. FASEB Journal, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic disturbance of blood vessels.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections. The instant compounds may also be useful in combination with other inhibitors of parts of the signalling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition.

Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

4-{3-[4-(-2-Oxo-2-H-pyridin-1-yl)benzyl]-3-H-imidazol-4-ylmethyl}benzonitrile

Step 1: 4-Iodobenzyl alcohol

Methyl 4-iodobenzoate (5 g, 19.07 mmol) was suspended in THF (100 mL). $LiBH_4$ (40 mmol) was added slowly, via syringe. Reaction mixture was heated to 60° for 4 days. 1N HCl was added slowly. Reaction mixture was stirred for ½ hour then was extracted 3 times with EtOAc. The organic layers were combined, washed with saturated $NaHCO_3$, brine, dried ($MgSO_4$), filtered and concentrated to give 4-iodobenzyl alcohol as a white solid.

$^1$H NMR (400 MHz, $CDCl_3$) δ 7.68 (d, 2H); 7.11 (d, 2H); 4.71 (d, 2H); 1.65 (t, 1H)

Step 2: 4-(-2-Oxo-2-H-pyridin-1-yl)benzyl alcohol

2-Hydroxypyridine (10.0 mmol; 956 mg), 4-iodobenzyl alcohol (17.09 mmol, 4.0 g), $K_2CO_3$ (11.0 mmol, 1.52 g), and copper (0.2 mmol, 15 mg) were mixed under argon and heated to 150° for 16 hours. The solid was partitioned between saturated $NaHCO_3$ and EtOAc. The layers were separated and the aqueous layer was back extracted twice with EtOAc. The organic layers were combined, washed with brine, dried over $MgSO_4$, filtered and concentrated to yield a yellow oil which was purified by flash chromatography (EtOAc) to give pure the title compound as a crystalline solid $^1$H NMR (400 MHz, $CDCl_3$) δ 7.50 (d, 2H); 7.43–7.41 (m, 4H); 6.68–6.65 (d, 1H): 6.27–6.23 (t, 1H); 4.75–4.75(d, 2H); 1.96–1.95 (bt, 1H).

Step 3: 4-(-2-Oxo-2-H-pyridin-1-yl)benzyl bromide

A solution of NBS (1.59 g, 8.94 mmol) and $CH_2Cl_2$ was cooled to 0°. To this solution (under Ar) was added $Me_2S$ (10.72 mmol, 0.78 mL) via syringe. This mixture was then cooled to −20° and added to a solution of the benzyl alcohol from Step 2 (1.2 g, 5.96 mmol) in $CH_2Cl_2$ via pipette. The reaction mixture was warmed to 0° and stirred for several hours. The residue was poured into ice water and extracted with $CH_2Cl_2$ (3×). The organic layers were combined, washed with brine, dried ($MgSO_4$), filtered and concentrated to give the title compound as a yellow solid, which will be used in the next step without further purification.

$^1$H NMR (400 MHz, $CDCl_3$) δ 7.53–7.51 (d, 2H); 7.37–7.31 (m, 4H); 6.67 (d, 1H); 6.25 (t, 1H); 4.52 (s, 2H).

Step 4: 4-(1-Trityl-1H-imidazol-4-ylmethyl)-benzonitrile

To a suspension of activated zinc dust (3.57 g, 54.98 mmol) in THF (50 mL) was added dibromoethane (0.315 mL, 3.60 mmol) and the reaction stirred under argon for 45 minutes, at 20° C. The suspension was cooled to 0° C. and α-bromo-p-tolunitrile (9.33 g, 47.6 mmol) in THF (100 mL) was added dropwise over a period of 10 minutes. The reaction was then allowed to stir at 20° C. for 6 hours and bis(triphenyl-phosphine)Nickel II chloride (2.40 g, 3.64 mmol) and 5-iodotrityl imidazole (15.95 g, 36.6 mmol) were added in one portion. The resulting mixture was stirred 16 hours at 20° C. and then quenched by addition of saturated NH$_4$Cl solution (100 mL) and the mixture stirred for 2 hours. Saturated aq. NaHCO$_3$ solution was added to give a pH of 8 and the solution was extracted with EtOAc (2×250 mL), dried (MgSO$_4$) and the solvent evaporated in vacuo. The residue was chromatographed (silica gel, 0–20% EtOAc in CH$_2$Cl$_2$) to afford the title compound as a white solid.

$^1$H NMR (CDCl$_3$, 400 Mz) δ (7.54 (2H, d, J=7.9 Hz), 7.38(1H, s), 7.36–7.29 (11H, m), 7.15–7.09(6H, m), 6.58 (1H, s) and 3.93(2H, s) ppm.

Step 5: 4-{3-[4-(2-Oxo-2-H-pyridin-1-yl)benzyl]-3-H-imidazol-4-ylmethyl}benzonitrile 4-(-2-Oxo-2-H-pyridin-1-yl)benzyl bromide from Step 3 (1.7 mmol, 450 mg) and 4-(1-trityl-1H-imidazol-4-ylmethyl)-benzonitrile (1.7 mmol) were suspended in CH$_3$CN and heated to reflux for 3 hours. The reaction mixture was concentrated and the residue taken up in MeOH and refluxed for 2 hours. The MeOH was removed in-vacuo. The resulting oil was partitioned between EtOAc and saturated NaHCO$_3$. The aqueous layer was extracted twice with EtOAc. The organic layers were combined, washed with brine, dried (MgSO$_4$), filtered and concentrated to yield an oil which was purified by flash chromatography using 5% IPA/CHCl$_3$ saturated with NH$_3$ as an eluent. Pure fractions were collected and concentrated to give a white solid. The solids were washed with warm 50% EtOAc/Hexane and collected on a frit. The white solid was collected and dried under high vacuum at 50° for 12 hours to give the title compound.

$^1$H NMR (400 MHz, CDCl$_3$) δ 7.58–7.55 (m, 3H); 7.42–7.40 (m, 1H); 7.39 (d, 2H); 7.27 (s, 1H); 7.20 (d, 2H); 7.04 (d, 2H); 6.67 (d, 1H); 6.27 (t, 1H); 4.97 (s, 2H); 3.89 (s, 2H).

Example 2

4-{3-[4-(3-Methyl-2-oxo-2-H-pyridin-1-yl)benzyl]-3-H-imidazol-4-ylmethyl}benzonitrile was prepared in a manner substantially similar to the procedure described above but substituting 3-methyl-2-hydroxypyridine for 2-hydroxypyridine in Step 2.

$^1$H NMR (400 MHz, CDCl$_3$) δ 7.59–7.55 (m, 3H); 7.55 (d, 2H); 7.19–7.19 (m, 3H); 7.03 (d, 2H); 6.95 (s, 1H); 6.20 (t, 1H); 4.96 (s, 2H); 3.87 (s, 2H); 2.19 (s, 3H).

Example 3

4-{3-[4-(2-Oxo-piperidin-1-yl)benzyl]-3-H-imidazol-4-ylmethyl}benzonitrile

Step 1: 5-Bromo-pentanoic acid 4-(5-bromo-pentanoylamino)-benzyl ester

4-Aminobenzylalcohol (Fluka, 4.5 g, 36.53 mmol) was dissolved in CHCl$_3$ under argon. NEt$_3$ (80.38 mmol, 11.20 mL) and 4-DMAP (1.8 mmol, 223 mg) were added and the suspension was cooled to 0°. 5-Bromovalerylchloride (Aldrich, 80.38 mmol, 16.03 g) in CHCl$_3$ (100 mL) was added dropwise over 40 minutes. The ice bath was permitted to expire and the reaction was stirred for 6 hours. The dark reaction mixture was washed with 10% citric acid, saturated NaHCO$_3$, H$_2$O and brine. The organic layer was dried (MgSO$_4$), filtered and concentrated to yield a dark oil. Flash chromatography (30% EtOAc/hexane) yielded the title compound as a light yellow solid.

$^1$H NMR (400 MHz, CDCl$_3$) δ 7.52 (d, 2H); 7.32 (d, 2H); 7.17 (bs, 1H); 5.07 (s, 2H); 3.46–3.43 (t, 2H); 3.41–3.37 (t, 2H); 2.42–2.38 (m, 4H); 1.96–1.79 (m, 8H).

Step 2: 5-Bromo-pentanoic acid 4-(2-oxo-piperidin-1-yl)-benzyl ester

The ester from Step 1 (1 g, 2.22 mmol) was dissolved in DMF. Cs$_2$CO$_3$ (725 mg, 2.22 mmol) was added and the reaction mixture was heated to 50° for 18 hours. TLC shows ~50% starting material remaining. Additional Cs$_2$CO$_3$ (2.22 mmol) was added the reaction mixture was heated at 50° for and additional 8 hours. The mixture was dissolved in 10% citric acid and extracted with EtOAc. The organic layer was washed with saturated NaHCO$_3$, H$_2$O and brine, dried (MgSO$_4$) filtered and concentrated to yield a yellow oil. Flash chromatography (EtOAc) yielded the title compound as a yellow oil.

$^1$H NMR (400 MHz, CDCl$_3$) δ 7.39–7.37 (d, 2H); 7.26–7.24 (d, 2H); 5.10 (d, 2H); 3.65–3.62 (bt, 2H); 3.42–3.38 (t, 2H); 2.57–2.55 (t, 2H); 2.41–2.38 (t, 3H); 2.04–1.89 (m, 4H); 1.88–1.80 (m, 4H).

Step 3: 1-(4-Hydroxymethyl-phenyl)-piperidin-2-one

The oxo-piperdinyl intermediate from Step 2 (2 g, 5.43 mmol) was dissolved in MeOH and treated with 1N NaOH (20 mL). The reaction was stirred for 20 minutes. The reaction mixture was concentrated in vacuo. The resulting oil was partitioned between H$_2$O and EtOAc. The layers were separated and the organic layer was dried (MgSO$_4$), filtered and concentrated to give the title compound as an off-white solid.

$^1$H NMR (400 MHz, CDCl$_3$) δ 7.41–7.39 (d, 2H), 7.26 (d, 2H); 4.70 (d, 2H); 3.64–3.62 (t, 2H); 2.58–2.57 (t, 2H); 1.70–1.67 (t, 1H)

Step 4: 1-(4-Bromomethyl-phenyl)-piperidin-2-one 1-(4-Hydroxymethyl-phenyl)-piperidin-2-one (200 mg, 0.97 mmol) was brominated to give the title compound following the procedure Example 1, Step 3.

$^1$H NMR (400 MHz, CDCl$_3$) δ 7.41–7.39 (d, 2H); 7.2 (d, 2H); 4.48 (d, 2H); 3.67–3.61 (t, 2H); 2.59–2.52 (t, 2H); 1.99–1.91 (m, 4H).

Step 5: 4-{3-[4-(2-Oxo-piperidin-1-yl)benzyl]-3-H-imidazol-4-ylmethyl}benzonitrile The bromomethylphenyl intermediate from Step 4 (260 mg, 0.97 mmol) and 4-(1-trityl-1H-imidazol-4-ylmethyl)-benzonitrile (0.97 mmol, 413 mg) were dissolved in CH$_3$CN and refluxed for 3 days. The CH$_3$CN was removed in vacuo and the residue was refluxed in MeOH for 2 hours. The MeOH was removed in vacuo and the residue treated with saturated NaHCO$_3$ and extracted with CHCl$_3$. The organic layer was washed with brine, dried (MgSO$_4$), filtered and concentrated to yield a yellow oil. Flash chromatography (4% IPA/CHCl$_3$ saturated with NH$_3$) yielded an off-white solid. The solid was triturated with EtOAc. the solids were collected and dried under hi-vacuum for 18 hours to give the title compound.

$^1$H NMR (400 MHz, CDCl$_3$) δ 7.55–7.51 (m, 3H); 7.26–7.19 (2d, 4H); 6.92–6.90 (m, 3H); 4.90 (s, 2H); 3.87 (s, 2H); 3.63–3.60 (t, 2H); 2.58–2.55 (t, 2H); 1.96–1.95 (m, 4H).

The following compounds were prepared by utilizing the procedures described in Example 3, but substituting the appropriately substituted starting reagents:

Example 4

4-{3-[3-Methyl-4-(2-oxopiperidin-1-yl)-benzyl]-3-H-imidazol-4-ylmethyl}-benzonitrile $^1$H NMR (400 MHz, CDCl$_3$) δ 7.55 (m, 3H); 7.15 D, 2H); 7.04 (d, 1H); 7.0 (s, 1H); 6.78 (m, 2H); 4.87 (s, 2H); 3.89 (s, 2H) 3.55 (m, 1H); 3.40 (m, 1H); 2.55 (t, 2H); 1.96 (m, 4H).

Example 5

(4-{3-[4-(2-Oxo-pyrrolidin-1-yl)-benzyl]-3H-imidazol-4-ylmethyl}-benzonitrile

L-799,683 $^1$H NMR (400 MHz, CDCl$_3$) δ 7.55 (m, 5H); 7.13 (d, 2H); 6.89 (m, 3H); 3.85 (m, 4H); 2.65 (t, 2H); 2.20 (t, 2H).

Example 6

4-{3-[4-(3-Methyl-2-oxo-2-H-pyrazin-1-yl)-benzyl]-3-H-imidazol-4-ylmethyl}-benzonitrile Step 1: D-alanine amide D-alanine (10 g, 71.6 mmol) was dissolved in EtOH in a pressure vessel. The solution was cooled to −78°. NH$_3$(l) (90 mL) was condensed into the reaction mixture. The pressure vessel was sealed and stirred at room temperature for 2 days. The excess ammonia was released from the vessel. The resulting suspension was concentrated to yield the title compound as a white solid which was dried under hi-vacuum for 16 hours overnight.

$^1$H NMR (400 MHz, CDCl$_3$) δ (12.52 (bs, 1H); 7.37 (d, 1H); 7.14 (d, 1H); 2.49 (s, 3H)

Step 2: 3-Methyl-2-hydroxypyrazine

D-alanine amide(7.5 g, 60.2 mmol) was suspended in MeOH (100 mL). H$_2$O (10 mL) was added to dissolve the solid. The solution was cooled to −30°. Glyoxal (72.2 mmol, 8.28 mL of 40% weight solution) was added in one portion. 12.5 N NaOH (12 mL) was added dropwise over 20 minutes. The resulting mixture was stirred at −30° for 40 minutes then at room temperature for another 3 hours. The reaction mixture was placed in refrigerator overnight. The yellow suspension was cooled to 0° and then treated with concentrated HCl (15 mL) followed by NaHCO$_3$ (12.3 g). The resulting neutral mixture was filtered through a frit. The filtrate was added to H$_2$O (12 mL) and concentrated to remove MeOH. The residue was treated with 100 mL MeOH and filtered to remove the salt. The filtrate was concentrated again to yield a tacky solid that was shaken with CHCl$_3$ (100 mL). Just enough water was added to make the dark aqueous phase supernatant (~15 mL). This aqueous layer was extracted with CHCl$_3$ (6×, 50 mL portions). The organic layers were combined and dried (MgSO$_4$), filtered and concentrated to yield 3-methyl-2-hydroxypyrazine as an off-white solid.

$^1$H NMR (400 MHz, CDCl$_3$) δ 12.52 (bs, 1H); 7.37 (d, 2H); 7.14 (d, 2H); 2.48 (s, 3H).

Step 3: 1-(4-Hydroxymethyl-phenyl)-3-methyl-1H-pyrazin-2-one

3-Methyl-2-hydroxypyrazine (1.10 g, 10.0 mmol), 4-Iodobenzyl alcohol from Example 1, Step 1 (4.0 g, 17.0 mmol), K$_2$CO$_3$ (1.52 g, 110 mmol), and copper (15 mg, 0.2 mmol) were heated under argon for 40 hours. The dark residue was partitioned between CHCl$_3$ and saturated NaHCO$_3$. The aqueous layer was back extracted twice with CHCl$_3$. The organic layers were combined, washed with brine, dried (MgSO$_4$), filtered and concentrated to give a light brown solid. Flash chromatography (EtOAc) yielded the title compound as a yellow solid.

$^1$H NMR (400 MHz, CDCl$_3$) δ 7.52 (d, 2H); 7.40 (d, 2H); 7.25 (d, 1H); 7.10 (d, 1H); 4.78 (d, 2H); 2.52 (s, 3H); 1.90 (t, 1H).

Step 4: 1-(4-Bromomethyl-phenyl)-3-methyl-1H-pyrazin-2-one

The pyrazinone intermediate from Step 3 (430 mg, 1.99 mmol) was dissolved in CH$_2$Cl$_2$ and added to a yellow suspension of NBS (531 mg, 2.98 mmol) and Me$_2$S (0.248 mL, 3.38 mmol) at −20°. The sulfoxium salt was formed at 0° then cooled to −20° before the addition of alcohol. After addition of the alcohol, the reaction mixture was stirred at 0° for several hours and then the cooling bath was allowed to expire overnight. The light brown solution was poured into H$_2$O and extracted with CHCl$_3$ (3×). The organic layers were combined, dried (MgSO$_4$), filtered and concentrated to yield a dark brown oil. Dissolved in EtOAc and filtered off resulting brown solid. The filtrate solidified to give the title compound as a yellow solid which will be used in the next step without further purification.

$^1$H NMR (400 MHz, CDCl$_3$) δ 7.55 m, 2H); 7.41 (m, 2H); 7.27 (d, 1H); 7.1 (d, 1H); 4.59 (s, 2H); 2.52 (s, 3H).

Step 5: 4-{3-[4-(3-Methyl-2-oxo-2-H-pyrazin-1-yl)-benzyl]-3-H-imidazol-4-ylmethyl}-benzonitrile The intermediate from Step 4 (142 mg, 0.50 mmol) and 4-(1-trityl-1H-imidazol-4-ylmethyl)-benzonitrile (230 mg, 0.53 mmol) were suspended in CH$_3$CN and heated to 8-° for 2 hours. The reaction mixture was concentrated and the residue dissolved in 5 mL MeOH and refluxed for 1 hour. The MeOH was removed in-vacuo and the residue partitioned between CHCl$_3$ and saturated NaHCO$_3$. The organic layer was washed with brine, dried (MgSO$_4$) filtered and concentrated to yield an oil. Flash chromatography (5% IPA/CHCl$_3$ saturated with NH$_3$) resulted in a beige solid. The solid was washed with warmed 50% (EtOAc/hexane) and filtered through a frit to yield an off-white solid which was dried at 45° overnight to give the title compound.

$^1$H NMR (400 MHz, CDCl$_3$) δ 7.59–7.54 (m, 3H); 7.36–7.34 (d, 2H); 7.18–7.16 (d, 2H); 7.05–7.03 (m, 3H); 6.96 (s, 1H); 4.97 (s, 2H); 3.87 (s, 2H); 2.52 (s, 3H).

Example 7

4-{3-[2-Methoxy-4-(2-oxo-2-H-pyridin-1-yl)-benzyl]-3-H-imidazol-4-ylmethyl}-benzonitrile Step 1: 4-Aminosalicyclic acid methyl ester 4-Aminosalicyclic acid (1 g, 98 mmol) was dissolved in MeOH. HCl(g) was bubbled through until the solution was saturated. The reaction mixture was heated at 70° for 16 hours. Additional MeOH was added to the reaction and saturated again with HCl (g). The reaction was heated at 70° for another 16 hours. The reaction mixture was neutralized with saturated NaHCO$_3$ and extracted with EtOAc. The resulting solid was recrystallized from hot 2:1 hexane/EtOAc and collected on a frit. The solid was further purified by flash chromatography eluting the product with 2/1 hexane/EtOAc to give 4-aminosalicyclic acid methyl ester as a solid.

$^1$H NMR (400 MHz, CDCl$_3$) δ 11.0 (s, 1H); 7.6 (d, 1H); 6.2 (d, 2H); 4.1 (bs, 2H); 3.85 (s, 3H).

Step 2: Methyl-2-hydroxy-4-iodo-benzoate

4-Aminosalicyclic acid methyl ester from Step 1 (13 g, 77.8 mmol) was suspended in 3N HCl (200 mL) and 20 mL THF. The reaction mixture was cooled to 0° and NaNO$_2$ (5.91 g, 85.6 mmol) dissolved in 50 mL H$_2$O was added. The reaction mixture was stirred for 10 minutes at room temperature and then KI (39.47 g, 233.5 mmol) dissolved in 75 mL H$_2$O was added and the reaction mixture was stirred for 16 hours. The reaction mixture was poured into EtOAc. The aqueous layer was extracted with EtOAc (3×). The organic layers were combined, washed with saturated sodium bisulfite (2×) and brine, dried (MgSO$_4$) filtered and concentrated to yield the title compound as a white solid.

Step 3: 2-Hydroxy-4-iodo-benzylalcohol

Methyl-2-hydroxy-4-iodo-benzoate from Step 2 (17.8 g, 64 mmol) was dissolved in THF. LiBH$_4$ (3.07 g, 144 mmol) was added portionwise. The reaction mixture was heated at 50° for 16 hours. The reaction mixture was quenched carefully with 1N HCl and then extracted with EtOAc (3×). The organic layers were combined, washed with brine, dried (MgSO$_4$) filtered and concentrated to yield the title compound as a white solid.

$^1$H NMR (400 MHz, CD$_3$OD) δ 7.15 (m, 2H); 7.0 (d, 1H); 4.6 (s, 2H).

Step 4: 2-Methoxy-4-iodo-benzylalcohol

2-Hydroxy-4-iodo-benzylalcohol from Step 3 (1.0 g, 4.0 mmol), Cs$_2$CO$_3$ (1.3 g, 4.0 mmol) and iodomethane (0.25 mL, 4.0 mmol) were dissolved in DMF and heated to 800 for 1 hour and then stirred at room temperature for 2 hours. The DMF was removed in vacuo and the residue was partitioned between H$_2$O and EtOAc. The aqueous layer was extracted with EtOAc (2x). The organic layers were combined, washed with H$_2$O and brine, dried (MgSO$_4$), filtered and concentrated to yield an oil. This oil was purified by flash chromatography eluting product with 30% EtOAC/Hexane to give the title compound.

Step 5: 1-(4-Hydroxymethyl-3-methoxy-phenyl)-1H-pyridin-2-one

2-Methoxy-4-iodo-benzylalcohol from Step 4 (700 mg, 2.65 mmol), 2-hydroxypyridinone (190 mg, 2.00 mmol), K$_2$CO$_3$ (387 mg, 2.8 mmol) and copper (63 mg, 1.0 mmol) were heated at 160° for 4 hours. The reaction mixture was treated with H$_2$O and CHCl$_3$. The layers were separated and the aqueous layer was extracted with CHCl$_3$. The organic layers were combined, washed with H$_2$O and brine, dried (MgSO$_4$), filtered and concentrated to yield an oil. Flash chromatography (2–4% IPA/CHCl$_3$ saturated with NH$_3$) yielded pure title compound as a solid.

$^1$H NMR (400 MHz, CDCl$_3$) δ 7.42–7.40 (m, 2H); 7.32 (d, 2H); 6.93 (m, 2H); 6.67 (d, 1H); 6.25 (t, 1H); 4.73 (d, 2H); 3.88 (s, 3H); 2.2 (bt, 1H).

Step 6: 1-(4-Bromomethyl-3-methoxy-phenyl)-1H-pyridin-2-one

The pyridinone intermediate from Step 5 (438 mg, 1.89 mmol) was brominated in the manner described in Example 6, Step 4 to give the title compound as an off white solid.

$^1$H NMR (400 MHz, CDCl$_3$) δ 7.45–7.43 (m, 3H); 7.26 (d, 1H); 6.95 (m, 2H); 6.66 (d, 1H); 6.25 (t, 1H); 4.56 (s, 2H); 3.91 (s, 3H).

Step 7: 4-{3-[2-Methoxy-4-(2-oxo-2-H-pyridin-1-yl)-benzyl]-3-H-imidazol-4-ylmethyl}-benzonitrile 4-(1-Trityl-1H-imidazol-4-ylmethyl)-benzonitrile was alkylated with the bromide and deprotected by the method described in Example 1, Step 5 to provide the title compound.

$^1$H NMR (400 MHz, CDCl$_3$) δ 7.55 (m, 3H); 7.41 (t, 1H); 7.22 (m, 2H); 6.92 (d, 2H); 6.80 (d, 1H); 6.65 (d, 2H); 6.25 (t, 1H); 4.93 (s, 2H); 3.94 (s, 2H); 3.84 (s, 3H).

Example 8

4-{1-[4-(5-Chloro-2-oxo-2H-pyridin-1-yl)-benzyl]-1H-imidazol-2-ylmethyl}-benzonitrile Step 1: 5-Chloro-1-(4-hydroxymethyl-phenyl)-1H-pyridin-2-one 5-Chloro-2-pyridinol (0.61 g, 4.7 mmol), 4-iodobenzylalcohol (1.00 g, 4.27 mmol), Copper (0.27 g, 4.27 mmol) and K$_2$CO$_3$ (0.65 g, 4.70 mmol) were heated at 180° C. for 16 hrs. The brown reaction mixture was cooled, diluted with EtOAc and washed with saturated NaHCO$_3$. The aqueous layer was extracted with EtOAc (2x) and the combined organic extracts were washed with brine, dried (Na$_2$SO$_4$) and evaporated in vacuo. The residue was chromatographed (silica gel, EtOAc as eluent) to afford the title compound as a white solid.

$^1$H NMR (400 MHz, CD$_3$OD) δ 7.74 (d, J=2.7 Hz, 1H), 7.59 (dd, J=3.0 and 9.6 Hz, 1H), 7.51 (d, J=8.6 Hz, 2H), 7.37 (d, J=8.4 Hz, 2H), 6.61 (d, J=9.4 Hz, 1H) and 4.67(s,1H) ppm.

Step 2: 1-(4-Bromomethyl-phenyl)-5-chloro-1H-pyridin-2-one

To N-bromosuccinimide (0.166 g, 0.929 mmol) in CH$_2$Cl$_2$ (3 mL) at 0° C. was added dimethylsulfide (0.082 mL, 1.11 mmol). The resulting suspension was cooled to −20° C. and a solution of the alcohol from Step 1 (0.146 g, 0.62 mmol) in CH$_2$Cl$_2$ was added dropwise over 2 minutes. The reaction mixture was stirred at 0° C. for 6 hrs and then poured into water and extracted with CH$_2$Cl$_2$. The extracts were dried (Na$_2$SO$_4$) and evaporated in vacuo. The residue was chromatographed (silica gel, EtOAc: CH$_2$Cl$_2$ 1:1 as eluent) to afford the title compound as a white solid.

$^1$H NMR (400 MHz, CDCl$_3$) δ 7.54 (d, J=8.4 Hz, 2H), 7.40–7.32 (m, 4H), 6.63 (dd, J=9.7 and 0.7 Hz, 1H) and 4.51(s,2H) ppm.

Step 3: 4-{1-[4-(5-Chloro-2-oxo-2H-pyridin-1-yl)-benzyl]-1H-imidazol-2-ylmethyl}-benzonitrile The bromide from Step 2 (0.154 g, 0.516 mmol) and 4-(1-trityl-1H-imidazol-4-ylmethyl)-benzonitrile (0.22 g, 0.516 mmol) in CH$_3$CN (2 mL) were heated at 55° C. After 18 hr methanol (3 mL) was added and the reaction was heated at reflux for 3 hrs, cooled and the solvent evaporated in vacuo. The residue was partitioned between sat. NaHCO$_3$ and CH$_2$Cl$_2$ and extracted with CH$_2$Cl$_2$. The organic extracts were dried (Na$_2$SO$_4$) and evaporated in vacuo. The residue was chromatographed (silica gel, MeOH: CH$_2$Cl$_2$ 5:95 as eluent) to afford the free base which was converted to the hydrochloride salt to afford the title compound as a white solid.

$^1$H NMR (400 MHz, CD$_3$OD) δ 9.03 (s, 1H), 7.80–7.55 (m, 4H), 7.55–7.20 (m, 7H) 6.64 (d, J=9.7 Hz, 1H), 5.45 (s,2H) and 4.18 (s,2H) ppm. Analysis: % Calc for C$_{22}$H$_{17}$N$_5$O.1.00HCl,0.55H$_2$O, 0.25 CH$_3$CN; C 61.39, H 4.39, N 16.31; % Found C 61.42, H 4.61, N 16.58

Example 9

4-[1-(2-Oxo-2H-[1,2']bipyridinyl-5'-ylmethyl)-1H-imidazol-2-ylmethyl]-benzonitrile Step 1: 5'-Methyl-[1,2']bipyridinyl-2-one 2-Pyridinone (1.00 g, 10.5 mmol), 2-bromo-5-methyl-pyridine (1.81 g, 10.5 mmol), Copper (0.013 g, 0.20 mmol) and K$_2$CO$_3$ (1.60 g, 11.6 mmol) were heated at 180° C. for 16 hrs. The brown reaction mixture was cooled, diluted with EtOAc and washed with saturated NaHCO$_3$. The aqueous layer was extracted with EtOAc (2x) and the combined organic extracts were washed with brine, dried (Na$_2$SO$_4$) and evaporated in vacuo. The residue was chromatographed (silica gel, EtOAc as eluent) to afford the title compound as a white solid.

$^1$H NMR (400 MHz, CDCl$_3$) δ 8.37 (brs, 1H), 7.86–7.78 (m,2H), 7.64(dd, J=2.3 and 8.3 Hz, 1H), 7.38(m, 1H), 6.63(d, J=9.2 Hz, 1H), 6.27(dt, J=1.3 and 7.0 Hz, 1H) and 2.39(s,3H)ppm.

Step 2: 5'-Bromomethyl-[1,2']bipyridinyl-2-one

A solution of the pyridine from Step 1 (0.10 g, 0.537 mmol), N-bromosuccinimide (0.096 g, 0.537 mmol) and AIBN ((0.005 g, 0.027 mmol) in CCl$_4$ (4 mL) was heated at reflux for 2 hrs. The solvent was evaporated in vacuo and the residue was chromatographed (silica gel, EtOAc: CH$_2$Cl$_2$ 25:75 to 50:50 gradient elution) to afford the title bromide.

$^1$H NMR (400 MHz, CD$_3$OD) δ 8.63 (brs, 1H), 8.04( dd, J=8.4 and 2.3 Hz, 1H), 7.87 (m, 1H), 7.77(d, J=8.3 Hz, 1H), 7.61(m, 1H), 6.62(d, J=9.7 Hz, 1H), 6.49 (dt, J=1.3 and 7.0 Hz, 1H) and 4.68 (s,2H) ppm.

Step 3: 4-[1-(2-Oxo-2H-[1,2']bipyridinyl-5'-ylmethyl)-1H-imidazol-2-ylmethyl]-benzonitrile The bromide from Step 2 (0.151 g, 0.565 mmol) and the 4-(1-trityl-1H-imidazol-4-ylmethyl)-benzonitrile (0.241 g, 0.565 mmol) in CH$_3$CN (3 mL) were heated at 60° C. After 18 hr methanol (4 mL) was added and the reaction was heated at reflux for 2 hrs, cooled and the solvent evaporated in vacuo. The residue was partitioned between sat. NaHCO$_3$ and CH$_2$Cl$_2$ and extracted with CH$_2$Cl$_2$. The organic extracts were dried (Na$_2$SO$_4$) and evaporated in vacuo. The residue was chromatographed (silica gel, MeOH: CH$_2$Cl$_2$ 2:98 to 5:95 gradient elution) to afford the free base which was converted to the hydrochloride salt to afford the title compound as a white solid.

$^1$H NMR (400 MHz, CD$_3$OD) δ 9.14 (s, 1H), 8.34(s, 1H), 7.88–7.70 (m, 3H), 7.67–7.56 (m, 3H), 7.47 (s, 1H), 7.30 (d, J=8.2 Hz, 2H), 6.64 (d, J=9.3 Hz, 1H), 6.52(t, J=6.6 Hz, 1H), 5.55(s, 2H) and 4.26 (s, 2H) ppm.

Analysis: % Calc for C$_{22}$H$_{17}$N$_5$O. 1.70HCl; C 61.39, H 4.39, N 16.31; % Found: C 61.42, H 4.61, N 16.58

Example 10

4-[1-(5-Chloro-2-oxo-2H-[1,2']bipyridinyl-5'-ylmethyl)-1H-imidazol-2-ylmethyl]-benzonitrile Step 1: 5-Chloro-5'-methyl-[1,2']bipyridinyl-2-one 5-Chloro-2-pyridinol (2.26 g, 17.4 mmol), 2-bromo-5-methylpyridine (3.00 g, 17.4 mmol), copper (0.022 g, 0.35 mmol) and K$_2$CO$_3$ (2.66 g, 19.2 mmol) were heated at 180° C. for 16 hrs. The brown reaction mixture was cooled, diluted with EtOAc and washed with saturated NaHCO$_3$. The aqueous layer was extracted with EtOAc (2×) and the combined organic extracts were washed with brine, dried (Na$_2$SO$_4$) and evaporated in vacuo. The residue was chromatographed (silica gel, EtOAc: CH$_2$Cl$_2$ 20:80 to 50:50 gradient elution) to afford the title compound as a white solid.

$^1$H NMR (400 MHz, CDCl$_3$) δ 8.37 (s, 1H), 7.96(d, J=3.0 Hz, 1H), 7.83 (d, J=8.4 Hz, 1H), 7.65(dd, J=2.4 and 8.2 Hz, 1H), 7.32(dd, J=2.9 and 9.7 Hz, 1H), 6.61(d, J=9.7 Hz, 1H) and 2.39(s,3H)ppm.

Step 2: 5'-Bromomethyl-5-chloro-[1,2']bipyridinyl-2-one

A solution of the pyridine from Step 1(1.00 g, 4.53 mmol), N-bromosuccinimide (0.81 g, 4.53 mmol) and AIBN (0.030 g, 0.18 mmol) in CCl$_4$ (40 mL) was heated at reflux for 2 hrs. The solids were filtered and the filtrate collected. The solvent was evaporated in vacuo and the residue chromatographed (silica gel, EtOAc: CH$_2$Cl$_2$ 25:75 to 50:50 gradient elution) to afford the title bromide.

$^1$H NMR (400 MHz, CDCl$_3$) δ 8.55 (s, 1H), 8.04( d, J=2.9 Hz, 1H), 8.01 (d, J=8.4 Hz, 1H), 7.88 (dd, J=2.4 and 8.6 Hz, 1H), 7.34(dd, J=2.9 and 9.8 Hz, 1H), 6.61(d, J=9.9 Hz, 1H) and 4.51 (s,2H) ppm.

Step 3: 4-[1-(5-Chloro-2-oxo-2H-[1,2']bipyridinyl-5'-ylmethyl)-1H-imidazol-2-ylmethyl]-benzonitrile hydrochloride The bromide from Step 2 (0.750 g, 2.50 mmol) and the 4-(1-trityl-1H-imidazol-4-ylmethyl)-benzonitrile (1.06 g, 2.50 mmol) in CH$_3$CN (10 mL) were heated at 60° C. The reaction was cooled to room temperature and the solids collected by filtration and washed with EtOAc (10 mL). The solid was suspended in methanol (50 mL) and heated at reflux for 1 hr, cooled and the solvent evaporated in vacuo. The sticky residue was stirred in EtOAc (40 mL) for 4 hrs and the resulting solid hydrobromide salt collected by filtration and washed with EtOAc (40 mL) and dried in vacuo. The hydrobromide salt was partitioned between sat. NaHCO$_3$ and CH$_2$Cl$_2$ and extracted with CH$_2$Cl$_2$. The organic extracts were dried (Na$_2$SO$_4$) and evaporated in vacuo. The residue was chromatographed (silica gel, MeOH: CH$_2$Cl$_2$ 4:96 to 5:95 gradient elution) to afford the free base which was converted to the hydrochloride salt to afford the title compound as a white solid.

$^1$H NMR (400 MHz, CD$_3$OD) δ 9.11 (s, 1H), 8.35 (s, 1H), 8.03(d, J=2.9 Hz, 1H), 7.83 (d, J=8.4 Hz, 1H), 7.76 (dd, J=2.4 and 9.6 Hz, 1H), 7.68–7.58 (m, 3H), 7.48 (s, 1H), 7.31(d, J=8.6 Hz, 2H), 6.68 (d, J=9.3 Hz, 1H), 5.53 (s, 2H) and 4.24 (s, 2H) ppm. Analysis: % Calc for C$_{22}$H$_{16}$N$_5$OCl. 1.75 HCl, 0.15 EtOAc; C 56.69, H 3.99, N 14.62; % Found: C 56.72, H 4.05, N 14.54

Example 11

4-[3-(6-Methyl-2-oxo-2-H-[1,2']bipyridinyl-5'-ylmethyl)-3H-imidazol-4-ylmethyl]-benzyonitrile Step 1: 2-Bromo(5-hydroxymethyl)pyridine 2-Bromonicotinic acid (5.00 g, 24.75 mmol) in 10 ml THF was cooled to 0° C. To the suspension was added a solution of 1M B$_3$H.THF (74.25 ml,74.25 mmol) dropwise via syringe. Removed ice bath and warmed to ambient temperature for 3 hrs. Cooled the reaction again to 0° C. and added dropwise 60 ml of sat'd K$_2$CO$_3$ solution. Stirred this mixture overnight. Diluted the reaction with water and the aqueous layer was extracted with EtOAc (2×). The combined organic extracts were washed with brine, dried (MgSO$_4$) and evaporated in vacuo. The residue was chromatographed (silica gel, 1–2% MeOH—CH$_2$Cl$_2$ solution) to afford the title compound as a white solid.

Step 2: 5'-Hydroxymethyl-6-methyl-[1,2']bipyridinyl-2-one 2-bromo(5-hydroxymethyl)pyridine (3.00 g, 15.95 mmol), 6-methylpyridone (2.08 g, 19.14 mmol), Copper (2.64, 19.14 mmol) and K$_2$CO$_3$ (0.635 g, 10.0 mmol) were heated at 140° C. for 3 hrs. Added CHC$_{13}$ to reaction when still warm and let stirred overnight. Filtered the mixture through a frit, concentrated in vacuo and the residue was chromatographed (silica gel, 0–4% MeOH-EtOAc solution). Obtained the title compound as a brown oil.

Step 3: 5'-Bromomethyl-6-methyl-[1,2']bipyridinyl-2-one

A solution of 5'-hydroxymethyl-6-methyl-[1,2'] bipyridinyl-2-one (0.90 g, 4.16 mmol) and CBr$_4$ (1.65 g, 5.0 mmol) in 30 ml CH$_2$Cl$_2$ at 0° C. was added a solution of triphenylphosphine (1.31 g, 5.0 mmol) in 10 ml CH$_2$Cl$_2$. Ice bath was removed and the solution was stirred for 2 hrs at ambient temperature. The solvent was evaporated in vacuo and the residue was chromatographed (silica gel, 100% EtOAc) to afford the title bromide.

Step 4: 4-[3-(6-Methyl-2-oxo-2-H-[1,2']bipyridinyl-5'-ylmethyl)-3H-imidazol-4-ylmethyl]-benzyonitrile The bromide from Step 3 (0.63 g, 2.20 mmol) and the 4-(1-trityl-1H-imidazol-4-ylmethyl)-benzonitrile (0.936 g, 2.20 mmol) in CH$_3$CN (15 mL) were heated at 90° C. for 15 hrs. The reaction was cooled to room temperature and concentrated in vacuo. The resulting foam was suspended in methanol (50 mL) and heated at reflux for 3 hr, cooled and the solvent evaporated in vacuo. The sticky residue was partitioned between sat'd. NaHCO$_3$ and CHCl$_3$ and extracted with CHCl$_3$. The organic extracts were dried (MgSO$_4$) and evaporated in vacuo. The residue was chromatographed (silica gel, 4% IPA-NH3 Sat'd CHCl$_3$) to afford an oil which was triturated with 90% EtOAc-hexanes to afford the title compound as a white solid.

$^1$H NMR (400 MHz, CDCl$_3$) δ 8.30 (s, 1H), 7.61–7.58 (m, 3H), 7.39–7.30(m, 3H), 7.23 (d, J=7.87 Hz, 2H), 6.98 (s, 1H), 6.53 (d, J=9.16 Hz 3H), 6.12 (d, J=6.96 Hz 1H), 5.01(s, 2H), 3.92 (s, 2H), 1.94 (s, 3H); Analysis: % Calc for C$_{23}$H$_{19}$N$_5$O. C 72.42, H 5.02, N 18.36; % Found: C 72.26, H 5.09, N 18.42

Example 12

4-[1-(5-Trifluoromethyl-2-oxo-2H-[1,2']bipyridinyl-5'-ylmethyl)-1H-imidazol-2-ylmethyl]-benzonitrile The title compound was prepared according to the procedures described in Steps 1 to 3 of Example 9, using 5 trifluoromethyl-2-pyridinol.

Analysis: % Calc for $C_{23}H_{16}N_5OF_3 \cdot 1.70$ HCl, C 56.54, H 3.59, N 14.08; % Found: C 55.61, H 3.90, N 13.92; FAB HRMS exact mass calcd for $C_{23}H_{17}N_5OF_3$ 436.1379614 (MH$^+$); found 436.1374620.

Example 13

4-[1-(3,5-dibromo-2-oxo-2H-[1,2']bipyridinyl-5'-ylmethyl)-1H-imidazol-2-ylmethyl]-benzonitrile Step 1 3,5-Dibromopyridin-2-ol A suspension of 2-pyridinol (3.00 g, 31.55 mmol) and bromine (1.79 ml, 34.7 mmol)) in 1,2-dichloroethane(35 mL) was stirred at room temperature and then at reflux for 18 hrs. The solids were collected by filtration and chromatographed (silica gel, MeOH: $CH_2Cl_2$ 5:95) to afford the dibromide.

$^1$H NMR (400 MHz, CD$_3$OD) δ 8.07 (d, J=2.9 Hz, 1H), and 7.62 (d, J=2.9 Hz, 1H) ppm.

Step 2: 3,5,-Dibromo-5'-methyl-[1,2']bipyridinyl-2-one 3,5,-Dibromo-2-pyridinol (1.47 g, 5.81 mmol), 2-bromo-5-methylpyridine (1.00 g, 5.81 mmol), copper (0.008 g, 0.116 mmol) and K$_2$CO$_3$ (0.883 g, 6.39 mmol) were heated at 180° C. for 18 hrs. The brown reaction mixture was cooled, diluted with EtOAc and stirred with saturated NaHCO$_3$ for 1 hr. The aqueous layer was extracted with EtOAc (2×) and the combined organic extracts were washed with brine, dried (Na$_2$SO$_4$) and evaporated in vacuo. The residue was chromatographed (silica gel, EtOAc: $CH_2Cl_2$ 10:90 to 30:70 gradient elution) to afford the title compound as a white solid.

$^1$H NMR (400 MHz, CDCl$_3$) δ 8.36 (s, 1H), 8.07(d, J=2.6 Hz, 1H), 7.86 (d, J=2.6 Hz, 1H), 7.83(d, 8.4 Hz, 1H), 7.66(d, J=8.4 Hz, 1H), and 2.41(s,3H) ppm.

Step 3: 5'-Bromomethyl-3,5-dibromo-[1,2']bipyridinyl-2-one

A solution of the pyridine from Step 2 (0.57 g, 1.73 mmol), N-bromosuccinimide (0.307 g, 1.73 mmol) and AIBN (0.011 g, 0.07 mmol) in CCl$_4$ (15 mL) was heated at reflux for 2 hrs. The solids were filtered and the filtrate collected. The solvent was evaporated in vacuo and the residue chromatographed (silica gel, EtOAc: $CH_2Cl_2$ 10:90 to 30:70 gradient elution) to afford the title bromide.

$^1$H NMR (400 MHz, CDCl$_3$) δ 8.55 (d, J=2.2 Hz, 1H), 8.14(d, J=2.6 Hz, 1H), 8.00 (d, J=8.3 Hz, 1H), 7.90(dd, 8.3 and 2.9 Hz, 1H), 7.87(d, J=2.6 Hz, 1H), and 4.51(s,2H) ppm.

Step 4: 4-[1-(3,5-Dibromo-2-oxo-2H-[1,2']bipyridinyl-5'-ylmethyl)-1H-imidazol-2-yl methyl]-benzonitrile hydrochloride The bromide from Step 3 (0.291 g, 0.687 mmol) and the 4-(1-trityl-1H-imidazol-4-ylmethyl)-benzonitrile (0.293 g, 0.687 mmol) in CH$_3$CN (4 mL) were heated at 60° C. The reaction was cooled to room temperature and the solids collected by filtration and washed with EtOAc (10 mL). The solid was suspended in methanol (20 mL) and heated at reflux for 1 hr, cooled and the solvent evaporated in vacuo. The hydrobromide salt was partitioned between sat. NaHCO$_3$ and CH$_2$Cl$_2$ and extracted with CH$_2$Cl$_2$. The organic extracts were dried (Na$_2$SO$_4$) and evaporated in vacuo. The residue was chromatographed (silica gel, MeOH: CH$_2$Cl$_2$ 3:97 to 4:96 gradient elution) to afford the free base which was converted to the hydrochloride salt to afford the title compound as a white solid.

$^1$H NMR (400 MHz, CD$_3$OD) δ 9.11 (d, J=1.4 Hz 1H), 8.31 (d, J=2.6 Hz, 1H), 8.16(d, J=2.6 Hz, 1H), 8.10(d, J=2.6 Hz, 1H), 7.82–7.72(m, 2H), 7.60 (d, J=8.2 Hz, 2H), 7.47 (s, 1H), 7.28(d, J=8.2 Hz, 2H), 5.53 (s, 2H) and 4.24 (s, 2H) ppm. Analysis: % Calc for $C_{22}H_{15}N_5OBr_2 \cdot 1.20$ HCl, C 46.44, H 2.87, N 12.31; % Found: C 46.75, H 3.22, N 11.91; FAB HRMS exact mass calcd for $C_{22}H_{16}N_5OBr_2$ 523.9716084 (MH$^+$); found 523.9716170.

Example 14

4-[1-(3-Bromo-2-oxo-2H-[1,2']bipyridinyl-5'-ylmethyl)-1H-imidazol-2-ylmethyl]-benzonitrile Step 1: 5'-Bromomethyl-3-bromo-[1,2']bipyridinyl-2-one A solution of 5'-Methyl-[1,2']bipyridinyl-2-one from example 9 Step 1 (1.20 g, 6.44 mmol), N-bromosuccinimide (1.15 g, 0.6.44 mmol) and AIBN ((0.060 g, 0.321 mmol) in CCl$_4$(20 mL) was heated at reflux for 2 hrs. The solvent was evaporated in vacuo and the residue was chromatographed (silica gel, EtOAc: CH$_2$Cl$_2$ 25:75 to 50:50 gradient elution) to afford the title bromide.

$^1$H NMR (400 MHz, CDCl$_3$) δ 8.56 (d, 1H), 8.05–7.80(m, 4H) 6.24 (t, J=9.5, 1H) and 4.53 (s,2H) ppm.

Step 2: 4-[1-(3-Bromo-2-oxo-2H-[1,2']bipyridinyl-5'-ylmethyl)-1H-imidazol-2-ylmethyl]-benzonitrile hydrochloride The bromide from Step 1 (0.161 g, 0.465 mmol) and the 4-(1-trityl-1H-imidazol-4-ylmethyl)-benzonitrile (0.198 g, 0.465 mmol) in CH$_3$CN (2.5 mnL) were heated at 60° C. for 18 hrs. The reaction was cooled to room temperature and the solids collected by filtration and washed with EtOAc. The solid was suspended in methanol (20 mL) and heated at reflux for 1 hr, cooled and the solvent evaporated in vacuo. The hydrobromide salt was partitioned between sat. NaHCO$_3$ and CH$_2$Cl$_2$ and extracted with CH$_2$Cl$_2$. The organic extracts were dried (Na$_2$SO$_4$) and evaporated in vacuo. The residue was chromatographed (silica gel, MeOH: CH$_2$Cl$_2$ 3:97 to 4:96 gradient elution) to afford the free base which was converted to the hydrochloride salt to afford the title compound as a white solid. FAB HRMS exact mass calcd for $C_{22}H_{17}N_5OBr$ 446.0610974 (MH$^+$); found 446.0614040.

Example 15

4-[1-(5-Bromo-2-oxo-2H-[1,2']bipyridinyl-5'-ylmethyl)-1H-imidazol-2-ylmethyl]-benzonitrile Step 1 5-Bromopyridin-2-ol To a solution of 2-pyridinol (4.70 g, 49.4 mmol) in CH$_2$Cl$_2$ (300 mL) at 0° C. was added a solution of bromine (7.90 g, 49.4 mmol) in CH$_2$Cl$_2$ dropwise. A precipitate was noted and the reaction was allowed to warm to room temperature and then heated at reflux for 1 hr. The reaction was allowed to cool to room temperature. CH$_2$Cl$_2$ was added the solution was washed sequentially with NaHCO$_3$ and 5% sodium thiosulphate solutions. The organic extracts were dried (MgSO$_4$) and evaporated in vacuo. (chromatographed (silica gel, EtOAc: CH$_2$Cl$_2$ 20:80 to 70:30) to afford the bromide.

$^1$H NMR (400 MHz, CD$_3$OD) δ 7.60–7.40 (m, 2H) and 6.52 (d, J=9.7 Hz, 1H) ppm.

Step 2: 5,-Bromo-5'-methyl-[1,2']bipyridinyl-2-one

5,-Bromo -2-pyridinol (0.76 g, 4.37 mmol), 2-bromo-5-methylpyridine (1.13 g, 6.55 mmol), copper (0.008 g, 0.13 mmol) and K$_2$CO$_3$ (0.664 g, 4.8 mmol) were heated at 155° C. for 1 hr. The brown reaction mixture was cooled, diluted with EtOAc (100 ml) and water (15 ml) and stirred for 1 hr. The aqueous layer was extracted with EtOAc (2×) and the combined organic extracts were washed with brine, dried (MgSO$_4$) and evaporated in vacuo. The residue was chromatographed (silica gel, EtOAc: CH$_2$Cl$_2$ 10:90 to 40:60 gradient elution) to afford the title compound as a white solid.

$^1$H NMR (400 MHz, CDCl$_3$) δ 8.37 (s, 1H), 8.03(d, J=2.6 Hz, 1H), 7.81 (d, J=8.2 Hz, 1H), 7.66(dd, J=8.2 and 2.3 Hz, 1H), 7.40(dd, J=9.7 and 2.6 Hz, 1H) 6.57 (d, J=9.7 Hz, 1H) and 2.40(s,3H) ppm.

Step 3 4-[1-(5-Bromo-2-oxo-2H-[1,2']bipyridinyl-5'-ylmethyl)-1H-imidazol-2-ylmethyl]-benzonitrile The title compound was prepared according to the procedures described in Steps 3 to 4 of Example 13 using 5-bromo-5'-methyl-[1,2']bipyridinyl-2-one from step 2.

Analysis: % Calc for $C_{22}H_{16}N_5OBr$. 1.00 HCl, 1.70$H_2O$; C 51.47, H 4.01, N 13.64; % Found: C 51.51, H 4.10, N 13.73; FAB HRMS exact mass calcd for $C_{22}H_{17}N_5OBr$ 446.0610974 (MH$^+$); found 446.0611700.

Example 16

4-[1-(5-Cyano-2-oxo-2H-[1,2']bipyridinyl-5'-ylmethyl)-1H-imidazol-2-ylmethyl]-benzonitrile Step 1: 5-Cyano-5'-methyl-[1,2']bipyridinyl-2-one To a suspension of 5-bromo-5'-methyl-[1,2']bipyridinyl-2-one (0.29 g, 1.09 mmol) and zinc cyanide (0.154 g, 1.30 mmol) in degassed DMF (3 ml) was added tetrakis (triphenylphosphine) palladium (151 mg, 0.13 mmol) and the reaction warmed to 95° C. for 4 hrs. The reaction was cooled and quenched with NH$_4$OH (10 ml) and water (30 ml). The aqueous phase was extracted with CH$_2$Cl$_2$, dried (MgSO$_4$), and evaporated in vacuo The residue was chromatographed (silica gel, EtOAc: CH$_2$Cl$_2$ 10:90 to 12:88 gradient elution) to afford the title compound.

$^1$H NMR (400 MHz, CDCl$_3$) δ 8.46 (d, J=2.6 Hz, 1H), 8.39(s, 1H), 7.80(d, J=8.4 Hz, 1H), 7.69 (d, J=8.4 and 2.2 Hz, 1H), 7.45(dd, J=9.7 and 2.6 Hz, 1H), 6.67 (d, J=9.5 Hz, 1H) and 2.42(s,3H) ppm.

Step 2: 4-[1-(5-Cyano-2-oxo-2H-[1,2']bipyridinyl-5'-ylmethyl)-1H-imidazol-2-ylmethyl]-benzonitrile The title compound was prepared according to the procedures described in Steps 3 to 4, Example 13, using 5,-cyano-5'-methyl-[1,2']bipyridinyl-2-one from step 1. FAB HRMS exact mass calcd for $C_{23}H_{17}N_6O$ 393.1458354 (MH$^+$); found 393.1445190.

Example 17

4-[1-(3,5-Dichloro-2-oxo-2H-[1,2']bipyridinyl-5'-ylmethyl)-1H-imidazol-2-ylmethyl]-benzonitrile Step 1: 5'-Methyl-3,5-dichloro-[1,2']bipyridinyl-2-one A solution of 5-Chloro-5'-methyl-[1,2']bipyridinyl-2-one from example 10 Step 1(2.00 g, 4.53 mmol) and N-chlorosuccinimide (1.21 g, 9.06 mmol) in acetonitrile (25 mL) was heated at reflux for 4 hrs. The solvent was evaporated in vacuo and the residue chromatographed (silica gel, EtOAc: CH$_2$Cl$_2$ 10:90 to 30:70 gradient elution) to afford the title compound.

$^1$H NMR (400 MHz, CDCl$_3$) δ 8.37 (s, 1H), 7.97( d, J=2.9 Hz, 1H), 7.86 (d, J=8.4 Hz, 1H), 7.67 (dd, J=2.4 and 8.4 Hz, 1H), 7.59(d, J=2.4 Hz, 1H), and 2.42 (s,3H) ppm.

Step 2: 4-[1-(3,5-Dichloro-2-oxo-2H-[1,2']bipyridinyl-5'-ylmethyl)-1H-imidazol-2-ylmethyl]-benzonitrile The title compound was prepared according to the procedures described in Steps 3 to 4, Example 13 using 5'-methyl-3,5-dichloro[1,2']bipyridinyl-2-one from step 1.

Analysis: % Calc for $C_{22}H_{15}N_5OCl_2$. 1.00 HCl; C 55.89, H 3.41, N 14.81; % Found: C 55.82, H 3.71, N 14.73

Example 18

(R,S) 4-{[3-(5-chloro-2-oxo-2H-[1,2']bipyridinyl-5'-ylmethyl)-3H-imidazol-4-yl]-hydroxy-methyl}-benzonitrile Step 1: (R,S) 4-[Hydroxy-(1-trityl-1H-imidazol-4-yl)-methyl]-benzonitrile To a solution of trityl-4-iodoimidazole (10.0 g, 22.92 mmol) in CH$_2$Cl$_2$ (93 ml) at 0° C. was added a solution of ethylmagnesium bromide (8.4 ml of a 3M solution in diethylether, 25.21 mmol) and the mixture stirred for 2 hr. 4-Cyanobenzaldehyde (3.36 g 25.21 mmol) was added and the reaction was stirred a furthur 18 hrs at room temperature. Saturated NH4Cl solution (100 ml) was added and the reaction stirred until the solids had dissolved. The pH of the solution was adjusted to 8.5 with sat NaHCO$_3$ solution and the aqueous extracted with CH$_2$Cl$_2$. The combined extracts were washed with brine, dried (MgSO$_4$) and evaporated in vacuo. The residue was suspended in EtOAc (200 ml) and the resulting solid was collected by filtration and dried in vacuo to afford the title compound.

$^1$H NMR (400 MHz, CDCl$_3$) δ 7.60 (d, J=8.4 Hz, 2H), 7.52 (d, J=8.4 Hz, 2H), 7.41(d, J=1.5 Hz, 1H), 7.38–7.28 (m, 15H), 7.15–7.05 (m, 6H), 6.62(s, 1H), 5.78(d, J=4.6 Hz, 1H) and 3.11(d, J=4.6 Hz, 1H) ppm.

Step 2: Acetic acid (4-cyano-phenyl)-(1-trityl-1H-imidazol-4-yl)-methyl ester

To a solution of the alcohol from step 1 (2.0 g, 4.53 mmol) in DMF (20 ml) at 0° C. was added acetic anhydride (0.641 ml 68.0 mmol) and the mixture stirred for 24 hr. Saturated NaHCO$_3$ solution (50 ml) was added and the aqueous extracted with EtOAc. The combined extracts were washed with brine, dried (MgSO$_4$) and evaporated in vacuo. The residue was suspended in diethylether (25 ml) and the resulting solid was collected by filtration and dried in vacuo to afford the title compound.

$^1$H NMR (400 MHz, CDCl$_3$) δ 7.62 (d, J=8.4 Hz, 2H), 7.53 (d, J=8.4 Hz, 2H), 7.40(d, J=1.3 Hz, 1H), 7.38–7.28 (m, 15H), 7.15–7.05 (m, 6H), 6.80(m, 2H), and 2.12(s, 3H) ppm.

Step 3: (R,S) 4-[1-(5-Chloro-2-oxo-2H-[1,2']bipyridinyl-5'-ylmethyl)-1H-imidazol-2-ylacetoxymethyl]-benzonitrile The bromide from Example 10 Step 2 (0.500 g, 1.67 mmol) and the 4-(1-trityl-1H-imidazol-4-ylacetoxymethyl)-benzonitrile (0.807 g, 1.67 mmol) in CH$_3$CN (2 mL) were heated at 60° C. for 20 hrs. The solvent was evaporated in vacuo The residue was suspended in methanol (10 mL) and heated at reflux for 1 hr, cooled and the solvent evaporated in vacuo. The residue was partitioned between CH$_2$Cl$_2$ and NaHCO$_3$ and the organic extracts were washed with brine, dried (Na$_2$SO$_4$) and evaporated in vacuo. The residue was chromatographed (silica gel, MeOH: CH$_2$Cl$_2$ 4:96 to 10:90 gradient elution) to afford the title compound.

$^1$H NMR (400 MHz, CD$_3$OD) δ 8.23 (s, 1H), 8.05–7.99 (m, 2H), 7.70–7.60(m, 3H), 7.44(dd, J=2.5 and 8.5 Hz, 1H), 7.40–7.32 (m, 3H), 6.90 (d, J=5.5 Hz, 2H), 6.60 (d, J=9.7 Hz, 1H), 5.18 (s, 2H) and 1.96 (s, 3H) ppm.

Step 4: (R,S) 4-{[3-(5-chloro-2-oxo-2H-[1,2']bipyridinyl-5'-ylmethyl)-3H-imidazol-4-yl]-hydroxy-methyl}-benzonitrile To a solution of the acetate from Step 3 (0.290 g, 0.694 mmol) in THF (3.8 ml) was added aqueous lithium hydoxide (0.763 ml, 0.763 mmol) and the reaction was stirred for 2 hours at room temperature. The reaction was partitioned between CH$_2$Cl$_2$ and NaHCO$_3$ and the organic extracts were washed with brine, dried (Na$_2$SO$_4$) and evaporated in vacuo. The residue was chromatographed (silica gel, MeOH: CH$_2$Cl$_2$ 4:96 to 10:90 gradient elution) to afford the title compound.

$^1$H NMR (400 MHz, CD$_3$OD) δ 8.29 (d, J=2.2 Hz, 1H), 7.97 (d, J=2.6 Hz, 1H), 7.81(d, J=8.4 Hz, 1H), 7.63(d, J=8.2 Hz, 2H), 7.55–7.45 (m, 3H), 7.37 (dd, J=9.8 and 2.8 Hz, 1H), 6.65 (s, 1H), 6.60 (d, J=9.7 Hz, 1H) 5.87(s, 1H), 5.15(d, J=15.7 Hz, 1H) and 5.06(d, J=15.7 Hz, 1H) ppm.

Example 19

(R,S) 4-{[3-(5-chloro-2-oxo-2H-[1,2']bipyridinyl-5'-ylmethyl)-3H-imidazol-4-yl]-fluoro-methyl}-benzonitrile To a solution of the alcohol from Step 4 Example 18 (0.0564 g, 0.135 mmol) in CH$_2$Cl$_2$ (3 ml) at 0° C. was added diethylamino-sulfur trifluoride (0.018 ml, 0.14 mmol) and the reaction was stirred for 1 hour and then allowed to warm to room temperature. The reaction was partitioned between $CH_2Cl_2$ and $NaHCO_3$ and the organic extracts were washed with brine, dried ($Na_2SO_4$) and evaporated in vacuo. The residue was chromatographed (silica gel, MeOH: $CH_2Cl_2$ 3:97 to 5:95 gradient elution) to afford the free base of the title compound which was converted to its hydrochloride salt. Analysis: % Calc for $C_{22}H_{15}N_5OFCl$ 1.10 HCl; C 57.40, H 3.63, N 14.94; % Found: C 57.41, H 3.73, N 14.78

Example 20

4-[3-(5-Chloro-2-oxo-2H-[1,2']bipyridinyl-5'-ylmethyl)-3H-imidazole-4-carbonyl]-benzonitrile To a solution of the alcohol from Step 4 Example 18 (0.039 g, 0.135 mmol) in $CH_2Cl_2$ (3 ml) at room temperature was added manganese dioxide (100 mg) and the mixture stirred for 1 hr The solids were removed by filtration and the filtrate evaporated in vacuo. The residue was chromatographed (silica gel, MeOH: $CH_2Cl_2$ 3:97 to 5:95 gradient elution) to afford the free base of the title compound which was converted to its hydrochloride salt.

Analysis: % Calc for $C_{22}H_{14}N_5O_2Cl$ 1.10HCl 1.00 $H_2O$; C 56.18, H 3.64, N 14.89; % Found: C 56.35, H 3.69, N 14.90

Example 21

4-{[3-(5-chloro-2-oxo-2H-[1,2']bipyridinyl-5'-ylmethyl)-3H-imidazol-4-yl]-methoxy-methyl}-benzonitrile Step 1: (R,S) 4-[Methoxy-(1-trityl-1H-imidazol-4-yl)-methyl]-benzonitrile To a solution of the alcohol from Step 1 Example 18 (0.600 g, 1.35 mmol) in $CH_2Cl_2$ (10 ml) at 0° C. was added diethylaminosulfurtrifluoride (0.268 ml, 2.02 mmol) and the reaction was stirred for 1 hour and then allowed to warm to room temperature. The reaction added to methanol (10 ml) and stirred at room temperature for 18 hrs and then the solvent was evaporated in vacuo. The residue was partitioned between $CH_2Cl_2$ and $Na_2CO_3$ and the organic extracts were washed with brine, dried ($Na_2SO_4$) and evaporated in vacuo. The residue was chromatographed (silica gel, EtOAc: $CH_2Cl_2$ 20:80) to afford the title compound.

$^1$H NMR (400 MHz, $CDCl_3$) δ 7.62 (d, J=8.4 Hz, 2H), 7.54(d, J=8.4 Hz, 2H), 7.41(d, J=1.5 Hz, 1H), 7.38–7.28 (m, 15H), 7.15–7.05 (m, 6H), 6.70(s, 1H), 5.28(s, 1H) and 3.35(s, 3H) ppm.

Step 2: (R,S) 4-{[3-(5-chloro-2-oxo-2H-[1,2']bipyridinyl-5'-ylmethyl)-3H-imidazol-4-yl]-methoxy-methyl}-benzonitrile The title compound was prepared according to the procedures described in step 3 example 10 using the imidazole from step 1.

FAB MS 432 (MH$^+$); Analysis: % Calc for $C_{23}H_{18}N_5O_2Cl$ 1.00 HCl 0.45$H_2O$; C 57.98, H 4.21, N 14.70; % Found: C 58.02, H 4.24, N 14.67

Example 22

(R,S) 4-[1-(5-Chloro-2-oxo-2H-[1,2']bipyridinyl-5'-ylmethyl)-1H-imidazol-2-ylbutyloxy-methyl]-benzonitrile Step 1: (R,S) 4-[Butoxy-(1-trityl-1H-imidazol-4-yl)-methyl]-benzonitrile To a solution of the alcohol from Step 1, Example 18 (0.600 g, 1.35 mmol) in $CH_2Cl_2$ (10 ml) at 0° C. was added diethylaminosulfurtrifluoride (0.268 ml, 2.02 mmol) and the reaction was stirred for 1 hour and then allowed to warm to room temperature. The reaction added to butanol (10 ml) and stirred at room temperature for 18 hrs and then the solvent was evaporated in vacuo. The residue was partitioned between $CH_2Cl_2$ and $Na_2CO_3$ and the organic extracts were washed with brine, dried ($Na_2SO_4$) and evaporated in vacuo. The residue was chromatographed (silica gel, EtOAc: $CH_2Cl_2$ 20:80) to afford the title compound.

$^1$H NMR (400 MHz, $CDCl_3$) δ 7.62 (d, J=8.4 Hz, 2H), 7.54(d, J=8.4 Hz, 2H), 7.40(d, J=1.5 Hz, 1H), 7.38–7.28 (m, 15H), 7.15–7.05 (m, 6H), 6.70(s, 1H), 5.37(s, 1H), 3.45(m, 2H), 1.57(m, 2H), 1.37(m, 2H), and 0.85(t, J=6.4 Hz, 3H) ppm.

Step 2: (R,S) 4-[1-(5-Chloro-2-oxo-2H-[1,2']bipyridinyl-5'-ylmethyl)-1H-imidazol-2-ylbutyloxy-methyl]-benzonitrile The title compound was prepared according to the procedures described in Step 3, Example 10 using the imidazole from step 1.

FAB MS 474 (MH$^+$); Analysis: % Calc for $C_{26}H_{24}N_5O_2Cl$ 1.25 HCl; C 60.26, H 4.91, N 13.51; % Found: C 60.53, H 4.92, N 13.56

Example 23

4-[5-(5-chloro-2-oxo-2H-[1,2']bipyridinyl-5'-ylmethyl)-imidazol-1-ylmethyl]-benzonitrile Step 1: 5'-Dibromomethyl-5-chloro-r[1,2']bipyridinyl-2-one A solution of the pyridine from Example 10 Step 1 (1.00 g, 4.53 mmol), N-bromosuccinimide (0.81 g, 4.53 mmol) and AIBN (0.030 g, 0.18 mmol) in $CCl_4$ (40 mL) was heated at reflux for 2 hrs. The solids were filtered and the filtrate collected. The solvent was evaporated in vacuo and the residue chromatographed (silica gel, EtOAc: $CH_2Cl_2$ 25:75 to 50:50 gradient elution) to afford the title dibromide.

$^1$H NMR (400 MHz, $CDCl_3$) δ 8.65 (s, 1H), 8.15–8.10 (m,2H), 8.07(d, J=2.9 Hz, 1H), 7.34(dd, J=2.8 and 9.7 Hz, 1H), 6.70(s, 1H), and 6.61 (d, J=9.9 Hz, 1H) ppm.

Step 2: 5'-Formyl-5-chloro-[1,2']bipyridinyl-2-one

To a suspension of the dibromide from Step 1(10.69 g, 29.33 mmol) in 95% aqueous ethanol (500 ml) was added silver nitrate (12.3 g, 176 mmol) and the mixture was heated at reflux for 3 hrs. The suspension was allowed to cool and the solids were removed by filtration. The filtrate was evaporated in vacuo and the residue chromatographed (silica gel, EtOAc: $CH_2Cl_2$ 20:80 to 40:60 gradient elution) to afford the title compound.

$^1$H NMR (400 MHz, $CDCl_3$) δ 10.15(s,1H), 9.02(s,1H), 8.31 (s, 2H), 8.18(d, J=2.7 Hz, 1H), 7.35(dd, J=2.7 and 9.7 Hz, 1H), and 6.63(d, J=9.7 Hz, 1H) ppm.

Step 3: 5-Chloro-5'-[hydroxy-(1-trityl-1H-imidazol-4-yl)-methyl]-[1,2']bipyridinyl-2-one To a solution of trityl-4-iodoimidazole (4.0 g, 9.16 mmol) in $CH_2Cl_2$ (50 ml) at room temperature was added a solution of ethyl-magnesium bromide (3.21 ml of a 3M solution in diethylether, 9.63 mmol) and the mixture stirred for 2 hr. The aldehyde from step 2 (2.15 g 9.16 mmol) was added and the reaction was stirred a further 18 hrs at room temperature. Saturated $NH_4Cl$ solution (50 ml) was added and the reaction stirred until the solids had dissolved. The pH of the solution was adjusted to 8.5 with sat $NaHCO_3$ solution and the aqueous extracted with $CH_2Cl_2$. The combined extracts were washed with brine, dried ($MgSO_4$) and evaporated in vacuo. The residue was chromatographed (silica gel, MeOH: $CH_2Cl_2$ 2:98 to 5:95 gradient elution) to afford the title compound.

$^1$H NMR (400 MHz, $CDCl_3$) δ 8.57(s,1H), 7.98(d, J=2.7 Hz, 1H), 7.91(m, 2H), 7.44(s, 1H),7.40–7.30(m, 9H), 7.20–7.00(m, 6H), 6.71(s, 1H), 6.60(d, J=9.7 Hz, 1H) 5.83 (d, J=3.3 Hz), and 3.15(brs, 1H) ppm.

Step 4: Thiocarbonic acid O-[(5-chloro-2-oxo-2H-[1,2'] bipyridinyl-5'-yl)-(1-trityl-1H-imidazol-4-yl)-methyl]ester O-phenyl ester To a solution of the alcohol from Step 3(1.01 g, 1.85 mmol) in $CH_2Cl_2$ (10 ml) at 0° C. was added DMAP (0.498 g, 4.08 mmol) and phenylthiochloroformate (0.282 ml, 2.04 mmol)and the mixture was stirred at room temperature for 18 hrs. The pH of the solution was adjusted to 8.5 with sat $NaHCO_3$ solution and the aqueous extracted with $CH_2Cl_2$. The combined extracts were washed with brine, dried ($MgSO_4$) and evaporated in vacuo. The residue was chromatographed (silica gel, MeOH: $CH_2Cl_2$ 2:98 to 3:97 gradient elution) to afford the title compound.

$^1$H NMR (400 MHz, $CDCl_3$) δ 8.69(d, J=2.2 Hz, 1H), 8.10(dd, J=2.4 and 8.4 Hz 1H), 8.02(d, J=2.7 Hz, 1H), 7.94(d, J=8.4 Hz,1H), 7.44(d, J=1.3 Hz), 7.40–7.20(m, 15H), 7.18–7.00(m, 6H), 6.81(s,1H), 6.60(d, J=9.7 Hz, 1H), and 5.77(s,1H) ppm.

Step 5: 5-chloro-5'-(1-trityl-1H-imidazol-4-ylmethyl)-[1,2'] bipyridinyl-2-one

To a solution of the thiocarbonate from Step 4 (0.263 g, 0.386 mmol) in benzene (3 ml) at room temperature was added tributyl tin hydride (0.159 ml, 3.74 mmol) and AIBN (0.012 g, 0.50 mmol) and the mixture was heated at 80° C. for 3 hrs. The solvent was evaporated in vacuo. The residue was chromatographed (silica gel, MeOH: $CH_2Cl_2$ 2:98 to 4:96 gradient elution) to afford the title compound.

$^1$H NMR (400 MHz, $CDCl_3$) δ 8.42(d, J=2.2 Hz, 1H), 7.95(d, J=2.9 Hz 1H), 7.83(d, J=8.2 Hz,1H), 7.70(dd, J=8.4 and 2.4 Hz,1H), 7.39(d, J=1.5 Hz), 7.35–7.30(m, 9H), 7.18–7.10(m, 6H), 6.63(s,1H), 6.59(d, J=9.7 Hz, 1H), and 3.94(s,2H) ppm.

Step 6: 4-[5-(5-chloro-2-oxo-2H-[1,2']bipyridinyl-5'-ylmethyl)-imidazol-1-ylmethyl]-benzonitrile 4-Cyanobenzyl bromide (0.159 g, 0.813 mmol) and the imidazole from step 5 (0.430 g, 0.813 mmol) in $CH_3CN$ (4 mL) were heated at 60° C. for 18 hrs. The reaction was cooled to room temperature and the solvent evaporated in vacuo The residue was suspended in methanol (10 mL) and heated at reflux for 1 hr, cooled and the solvent evaporated in vacuo. The residue was partitioned between sat. $NaHCO_3$ and $CH_2Cl_2$ and extracted with $CH_2Cl_2$. The organic extracts were dried ($MgSO_4$) and evaporated in vacuo. The residue was chromatographed (silica gel, MeOH: $CH_2Cl_2$ 3:97 to 4:96 gradient elution) to afford the free base which was converted to the hydrochloride salt to afford the title compound as a white solid.

$^1$H NMR (400 MHz, $CD_3OD$) δ 9.10 (d, J=1.5 Hz, 1H), 8.25 (s, 1H), 7.98 (d, J=2.9 Hz, 1H), 7.75–7.66(m,4H), 7.60 (dd, J=2.7 and 9.6 Hz, 1H), 7.51 (s, 1H), 7.29 (d, J=8.3 Hz, 2H), 6.64 (d, J=9.9 Hz, 1H), 5.59 (s, 2H) and 4.15 (s, 2H) ppm. FABMS 402 (MH$^+$).

Example 24

5'-(3-Benzyl-3H-imidazol-4-ylmethyl)-5-chloro-[1, 2']bipyridinyl-2-one

Step 1: 5'-(3-Benzyl-3H-imidazol-4-ylmethyl)-5-chloro-[1, 2']bipyridinyl-2-one (L-824,630)

A mixture of 5-chloro-5'-(1-triphenylmethyl-1H-imidazol-4-ylmethyl)-[1,2']bipyridinyl-2-one from Example 23, Step 5 (0.10 g, 0.189 mmol) and benzyl bromide (0.036 g, 0.208 mmol) in $CH_3CN$ (1 mL) was heated at 50° C. for 18 h. The solvent was removed in vacuo and the residue was heated to reflux in MeOH (3 mL) for 1 h, then concentrated under reduced pressure. The residue was partitioned between saturated $NaHCO_3$ (3 mL) and $CH_2Cl_2$ (3 mL). The organic layer was removed and the aqueous phase extracted further with $CH_2Cl_2$ (2×3 mL). The combined organic extracts were dried ($MgSO_4$), filtered, and concentrated under reduced pressure. The residue was purified by flash column chromatography, eluting with $CH_2Cl_2$; 4% MeOH; 0.4% $NH_4OH$, to give the title compound:

$^1$H NMR (400 MHz, $CDCl_3$) δ 8.24 (d, J=2.4 Hz, 1H), 7.96 (d, J=2.9 Hz, 1H), 7.86 (d, J=8.3 Hz, 1H), 7.58 (s, 1H), 7.51 (dd, J=8.3 and 2.4 Hz, 1H), 7.36–7.28 (m, 4H), 6.97 (dd, J=7.0 and 2.2 Hz, 1H), 6.93 (s, 1H), 6.61 (d, J=9.7 Hz, 1H), 4.98 (s, 2H) and 3.82 (s, 2H) ppm. This was treated with HCl to give its hydrochloride salt as a white solid.

Analysis: % Calc for $C_{21}H_{17}N_4OCl.2.5HCl.2.2H_2O$; C 49.68, H 4.75, N 11.04; % Found: C 49.72, H 4.70, N 11.00

Example 25

5-Chloro-5'-(3-pyrazin-2-ylmethyl-3H-imidazol-4-ylmethyl)-[1,2']bipyridinyl-2-one Step 1: (2-Chloromethyl)pyrazine To a stirred solution of (2-hydroxymethyl)pyrazine (Maury et al. (1982) *Bull. Soc. Chim. Belg.* 91, 153–162) (0.40 g, 3.6 mmol) in $CH_2Cl_2$ (40 mL) at 0° C. was added thionyl chloride (1.6 g, 13 mmol), dropwise. The mixture was stirred for 18 h at ambient temperature then concentrated under reduced pressure. The residue was partitioned between saturated $NaHCO_3$ (20 mL) and $CH_2Cl_2$ (25 mL). The organic layer was removed and the aqueous phase extracted further with $CH_2Cl_2$ (3×25 mL). The combined organic extracts were dried ($MgSO_4$), filtered, and concentrated under reduced pressure. The resulting oil was purified by flash column chromatography, eluting with hexanes; 30% EtOAc, to give the title compound:

$^1$H NMR (400 MHz, $CDCl_3$) δ 8.76 (s, 1H), 8.58–8.54 (m, 2H), 4.72 (s, 2H) ppm. The compound was converted to its hydrochloride salt for storage.

Step 2: 5-Chloro-5'-(imidazol-4-ylmethyl)-[1,2']bipyridinyl-2-one

To a stirred solution of 5-chloro-5'-(1-triphenylmethyl-1H-imidazol-4-ylmethyl)-[1,2']bipyridinyl-2-one from Example 23 step 5 (1.00 g, 1.89 mmol) in $CH_2Cl_2$ (15 mL) was added trifluoroacetic acid (0.86 g, 7.6 mmol) and the dark yellow solution was stirred for 5 min at ambient temperature. Triethylsilane was added dropwise until the yellow color was dissipated and the solution was concentrated in vacuo. The residue was purified by flash column chromatography, eluting with $CH_2Cl_2$; 1% MeOH; 0.1% $NH_4OH$, to give the title compound:

$^1$H NMR (400 MHz, $CDCl_3$) δ 8.39 (d, J=2.2 Hz, 1H), 8.12 (br s, 1H), 7.88 (d, J=2.8 Hz, 1H), 7.74 (d, J=8.4 Hz, 1H), 7.66 (dd, J=8.4 and 2.2 Hz, 1H), 7.42 (s, 1H), 7.34 (ddd, J=9.8, 2.8 and 0.9 Hz, 1H), 6.70 (s, 1H), 6.57 (d, J=9.8 Hz, 1H) and 3.94 (s, 2H) ppm.

Step 3: 5-Chloro-5'-(3-pyrazin-2-ylmethyl-3H-imidazol-4-ylmethyl)-[1,2']bipyridinyl-2-one (L-824,867)

To a stirred solution of 5-chloro-5'-(imidazol-4-ylmethyl)-[1,2']bipyridinyl-2-one from Step 2 (0.200 g, 0.698 mmol) in dry, degassed DMF (1 mL) at 0° C. was added NaH (61 mg of a 60% dispersion in mineral oil, 1.53 mmol). The mixture was stirred at 0° C. for 30 min and then (2-chloromethyl)pyrazine hydrochloride from Step 1 (127 mg, 0.770 mmol) was added. The reaction mixture was allowed to warm to ambient temperature and stirred for 2 h, then concentrated in vacuo. The residue was partitioned between saturated $NaHCO_3$ (2 mL) and $CH_2Cl_2$ (5 mL). The organic layer was removed and the aqueous phase extracted further with $CH_2Cl_2$ (5×5 mL). The combined organic extracts were dried (MgSO$_4$), filtered, and concentrated under reduced pressure. The residue was purified by flash column chromatography, eluting with CH$_2$Cl$_2$; 4% MeOH; 0.4% NH$_4$OH, to give a mixture of regioisomers. Further purification by preparative TLC, eluting with CH$_2$Cl$_2$; 10% MeOH, gave the title compound:

$^1$H NMR (400 MHz, CDCl$_3$) δ 8.54–8.49 (m, 2H), 8.30 (d, J=2.0 Hz, 1H), 8.24 (s, 1H), 7.97 (d, J=2.8 Hz, 1H), 7.86 (d, J=8.4 Hz, 1H), 7.82 (s, 1H), 7.55 (dd, J=8.4 and 2.4 Hz, 1H), 7.34 (dd, J=9.7 and 2.8 Hz, 1H), 6.97 (s, 1H), 6.61 (d, J=9.7 Hz, 1H), 5.18 (s, 2H) and 4.00 (s, 2H) ppm. This was treated with HCl to give its hydrochloride salt as a white solid.

Analysis: % Calc for C$_{19}$H$_{15}$N$_6$OCl.2.1 HCl.2.5H$_2$O; C 45.60, H 4.45, N 16.79; % Found: C 45.57, H 4.50, N 16.80

Example 26

5-[5-(5-Chloro-2-oxo-2H-[1,2']bipyridinyl-5'-ylmethyl)-imidazol-1-ylmethyl]-furan-2-carbonitrile Step 1: 5-Cyano-furan-2-carboxylic acid methyl ester A solution of bromofuroate (1.176 g, 5.736 mmol), zinc cyanide (1.01 g, 8.60 mmol) and tetrakis triphenylphosphine palladium (0.663 g, 0.574 mmol) in DMF (8.0 ml) was degassed with argon and then heated at 80° C. for 4 hrs. Saturated NH$_4$Cl solution (50 ml) and water (100 ml) were added and the aqueous extracted with EtOAc. The combined extracts were washed with saturated NaHCO$_3$ solution, water, dried (MgSO$_4$) and evaporated in vacuo. The residue was chromatographed (silica gel, CH$_2$Cl$_2$) to afford the title compound.

$^1$H NMR (400 MHz, CDCl$_3$) δ 7.22 (d, J=3.7 Hz,1H), 7.15 (d, J=3.7 Hz,1H), and 3.95 (s, 3H) ppm.

Step 2: 5-hydroxymethyl-furan-2-carbonitrile

A solution of the ester from step 1 (0.098 g, 0.652 mmol), in ethanol (2.5 ml) at 0° C. was treated with sodium borohydride (0.11 g, 2.936 mmol) and the reaction was stirred for 2 hrs. Saturated NH$_4$Cl solution (1 ml) was added and the aqueous extracted with diethylether. The combined extracts were dried (MgSO$_4$) and evaporated in vacuo. The residue was chromatographed (silica gel, diethylether) to afford the title compound.

$^1$H NMR (400 MHz, CDCl$_3$) δ 7.06 (d, J=3.7 Hz,1H), 6.42 (d, J=3.7 Hz,1H), 4.65(d, J=5.9 Hz, 2H) and 2.48 (t, J=5.9 Hz, 1H) ppm.

Step 3: 5-[5-(5-chloro-2-oxo-2H-[1,2']bipyridinyl-5'-ylmethyl)-imidazol-1-ylmethyl]-furan-2-carbonitrile To a solution of the alcohol from step 2 (0.017 g, 0.137 mmol), 5-chloro-5'-(1-triphenylmethyl-1H-imidazol-4-ylmethyl)-[1,2']bipyridinyl-2-one from Example 23, Step 5 (0.0758 g, 0.143 mmol) and diisopropylethylamine (0.047 mL, 1.49 mmol) in dichloromethane (1.3 mL) at −78° C. was added trifluoromethanesulfonic anhydride (0.023 mL, 0.136 mmol) and the mixture stirred at −78° C. for 1 hour. The mixture was allowed to warm to 0° C. and stirred for 2 hours. The solvent was evaporated in vacuo. The residue was dissolved in methanol (1 mL), heated at reflux for 2 hour, and the solvent evaporated in vacuo. The residue was partitioned between CH$_2$Cl$_2$ and sat. aq. NaHCO$_3$ solution. The organic layer was dried, (Na$_2$SO$_4$) and the solvent evaporated in vacuo. The residue was chromatographed (Silica gel, 1:99 to 3:97 MeOH:CH$_2$Cl$_2$) to afford the title compound as a white solid.

FAB HRMS exact mass calcd for C$_{20}$H$_{15}$N$_5$O$_2$Cl 392.0908794 (MH$^+$); found 3920911740.

Example 27

(R,S) Acetic acid (5-chloro-2-oxo-2H-[1,2'] bipyridinyl-5'-yl)-[3-(4-cyano-benzyl)-3H-imidazol-4-yl]-methyl ester Step 1: (R,S) Acetic acid (4-cyano-phenyl)-(1-trityl-1H-imidazol-4-yl)-methyl ester To a solution of the alcohol from Example 23, Step 3 (2.29 g, 4.20 mmol) in CH$_2$Cl$_2$ (50 ml) at 0° C. was added pyridine (1.02 ml, 12.6 mmol) and acetic anhydride (0.595 ml 6.30 mmol) and the mixture stirred for 18 hr. Saturated NaHCO$_3$ solution (50 ml) was added and the aqueous extracted with CH$_2$Cl$_2$. The combined extracts were washed with water, dried (MgSO$_4$) and evaporated in vacuo. The residue was chromatographed (silica gel, MeOH: CH$_2$Cl$_2$ 3:97 to 4:96 gradient elution) to afford the title compound.

$^1$H NMR (400 MHz, CDCl$_3$) δ 8.62 (m, 1H), 8.00 (d, J=2.3 Hz,1H), 7.99 (s, 1H), 7.42 (m,1H), 7.38–7.30(m,11H), 7.18–7.05 (m, 6H), 6.90–6.80(m,2H) 6.60 (d, J=9.7 Hz, 1H), and 2.12 (s, 3H) ppm. FABMS 402 (MH$^+$).

Step 2: (R,S) Acetic acid (5-chloro-2-oxo-2H-[1,2'] bipyridinyl-5'-yl)-[3-(4-cyano-benzyl)-3H-imidazol-4-yl]-methyl ester The title compound was prepared according to the procedures described in Step 6, Example 23 using the imidazole from step 1.

FAB HRMS exact mass calcd for C$_{24}$H$_{18}$N$_6$O$_3$Cl 460.1170 (MH$^+$); found 460.1160.

Example 28

4-{5-[(5-chloro-2-oxo-2H-[1,2']bipyridinyl-5'-yl)-hydroxy-methyl]-imidazol-1-ylmethyl}-benzonitrile Step 1: (R,S) 4-{5-[(5-chloro-2-oxo-2H-[1,2']bipyridinyl-5'-yl)-hydroxy-methyl]-imidazol-1-ylmethyl}-benzonitrile hydrochloride To a solution of the acetate from Example 27 (0.433 g, 0.940 mmol) in THF (5.0 ml) was added aqueous lithium hydoxide (1.05 ml, 1.05 mmol) and the reaction was stirred for 18 hours at room temperature. The reaction was partitioned between CH$_2$Cl$_2$ and water. The organic extracts were washed with brine, dried (Na$_2$SO$_4$) and evaporated in vacuo to afford the free base which was converted to the hydrochloride salt to afford the title compound as a white solid. FAB HRMS exact mass calcd for C$_{22}$H$_{17}$N$_5$O$_2$Cl 418.1065 (MH$^+$); found 408.1076.

Analysis: % Calc for C$_{22}$H$_{16}$N$_5$O$_2$Cl 1.05 HCl, 0.90H$_2$O; C 60.26, H 4.91, N 13.51; % Found: C 60.53, H 4.92, N 13.56

Example 29

(R,S) 4-{5-[(5-chloro-2-oxo-2H-[1,2']bipyridinyl-5'-yl)-methoxy-methyl]-imidazol-1-ylmethyl}-benzonitrile Step 1: (R,S) 4-{5-[(5-chloro-2-oxo-2H-[1,2']bipyridinyl-5'-yl)-methoxy-methyl]-imidazol-1-ylmethyl}-benzonitrile To a solution of the alcohol from Example 28 (0.330 g, 0.79 mmol) in CH$_2$Cl$_2$ (10 ml) at 0° C. was added diethylaminosulfurtrifluoride (0.115 ml, 0.87 mmol) and triethylamine (0.121 ml, 0.87 mmol) and the reaction was stirred for 1 hour at room temperature. The reaction mixture was partitioned between CH$_2$Cl$_2$ and water and the organic extracts were washed with Na$_2$CO$_3$, dried (Na$_2$SO$_4$) and evaporated in vacuo The residue was dissolved in CH$_2$Cl$_2$ (6 ml) and added to methanol (10 ml) and stirred at room temperature for 24 hrs and then the solvent was evaporated in vacuo. The residue was partitioned between CH$_2$Cl$_2$ and Na$_2$CO$_3$ and the organic extracts were washed with brine, dried (Na$_2$SO$_4$) and evaporated in vacuo. The residue was chromatographed (silica gel, MeOH: CH$_2$Cl$_2$ 3:97) to afford the free base which was converted to the hydrochloride salt to afford the title compound as a white solid.

FAB HRMS exact mass calcd for C$_{23}$H$_{19}$N$_5$O$_2$Cl 432.122 (MH$^+$); found 432.123.

Example 30

(R,S) 4-{5-[butoxy-(5-chloro-2-oxo-2H-[1,2']bipyridinyl-5'-yl)-methyl]-imidazol-1-ylmethyl}-benzonitrile Step 1: (R,S) 4-{5-[Butoxy-(5-chloro-2-oxo-2H-[1,2']bipyridinyl-5'-yl)-methyl]-imidazol-1-ylmethyl}-benzonitrile To a solution of the alcohol from Example 28 (0.330 g, 0.79 mmol) in $CH_2Cl_2$ (10 ml) at 0° C. was added diethylaminosulfurtrifluoride (0.115 ml, 0.87 mmol) and triethylamine (0.121 ml, 0.87 mmol) and the reaction was stirred for 1 hour at room temperature. The reaction mixture was partitioned between $CH_2Cl_2$ and water and the organic extracts were washed with $Na_2CO_3$, dried ($Na_2SO_4$) and evaporated in vacuo The residue was dissolved in $CH_2Cl_2$ (6 ml) and added to n-butanol (10 ml) and triethylamine (0.121 ml, 0.87 mmol) and stirred at room temperature for 24 hrs and then the solvent was evaporated in vacuo. The residue was partitioned between $CH_2Cl_2$ and $Na_2CO_3$ and the organic extracts were washed with brine, dried ($Na_2SO_4$) and evaporated in vacuo. The residue was chromatographed (silica gel, $MeOH:CH_2Cl_2$ 3:97) to afford the free base which was converted to the hydrochloride salt to afford the title compound as a white solid. FABMS 474 ($MH^+$).

Example 31

1-{4-[5-(4-Cyanophenyloxy)imidazol-1-ylmethyl]phenyl}-1H-pyridin-2-one

Step 1: 4-(4-Bromophenyloxy)imidazole

To a mixture of liquid 4-bromophenol (25 g, mp 64–68° C.) at 100–110° C. and its sodium salt [Prepared from 3.5 g (20 mmol) 4-bromo-phenol and sodium metal (0.46 g, 20 mmol) in anhydrous methanol. The resultant solution was concentrated and the residual solvent removed under vacuum overnight], neat methyl N-(cyano-methyl)methanimidate (2 mL, 20 mmol; Hosmane, R. S. et al, J. Org. Chem., p. 1212, 1984) was added dropwise over a period of 10 minutes under a slow stream of dry argon. The resultant mixture was stirred at 100° C. for 2 h, and the reaction product partitioned between methylene chloride (250 mL) and aqueous sodium hydroxide (1M, 250 mL). The aqueous layer was separated and extracted with methylene chloride (3×50 mL). The organic extracts were combined, washed with brine (50 mL), dried over anhydrous potassium carbonate, filtered and concentrated. The residue was subjected to column chromatography on silica gel eluting with a mixture of 7:3 v/v chloroform and acetone. Collection and concentration of appropriate fractions provided the titled compound as white powder.

$^1$H NMR δ DMSO-$d_6$ 7.49 (1H, s), 7.48 (2H, d, J=9.0 Hz), 6.93 (2H, d, J=9.0 Hz), 6.85 (1H, s).

Step 2: 4-(4-Bromophenyloxy)-1-trityl-1H-imidazole

To a cold (0° C.) solution of 4-(4-bromophenyloxy)-imidazole (1.2 g, 5.0 mmol) and triethylamine (0.76 mL, 5.5 mmol) in DMF (5 mL) under an atmosphere of argon, solid trityl chloride (1.46 g, 5.3 mmol) was added. The resultant mixture was stirred at room temp overnight. The product mixture was concentrated onto silica gel, loaded onto a column of silica gel, and eluted with a mixture of 9:1 chloroform and acetone. Collection and concentration of appropriate fractions provided the titled compound as white powder.

Step 3: 1-{4-[5-(4-Bromophenyloxy)imidazol-1-ylmethyl]-phenyl}1H-pyridin-2-one

A mixture of 4-(4-bromophenyloxy)-1-trityl-1H-imidazole (0.345 g, 0.72 mmol) and the bromide from Example 1, Step 3 (0.19 g, 0.72 mmol) in anhydrous acetonitrile (10 mL) was heated under reflux at 60° C. for 24 h. The resultant solution was concentrated, and the residue dissolved in methanol. The methanolic solution was heated under reflux for 3 h, and concentrated under vacuum. The residue was subjected to column chromatography on silica gel eluting with 1:1 v/v 5% methanol in chloroform and chloroform saturated with ammonia gas. Collection and concentration of appropriate fractions provide the titled compound.

$^1$H NMR CDCl$_3$ δ 7.5–7.2 (10H, m), 6.85 (2H, d, J=9.0 Hz), 6.64 (2H, m), 6.25 (1H, t, J=5.4 Hz), 5.00 (2H, s).

Step 4: 1-{4-[5-(4-Cyanophenyloxy)imidazol-1-ylmethyl]phenyl}-1H-pyridin-2-one

A mixture of 1-{4-[5-(4-bromophenyloxy)imidazol-1-ylmethyl]-phenyl}-1H-pyridin-2-one (145 mg, 0.35 mmol) and zinc cyanide (24 mg, 0.2 mmol) in DMF (3 mL) was purged with argon for 10 min. A solution of tetrakis(triphenylphosphine)palladium(0) (40 mg, 35 μmol) in DMF (1 mL) was added. The resultant mixture was stirred under argon at 80° C. overnight, and concentrated under vacuum. The residue was subjected to column chromatography on silica gel eluting with 1:1 v/v 5% methanol in chloroform and chloroform saturated with ammonia gas. Collection and concentration of appropriate fractions provide the titled compound as white solid.

$^1$H NMR CDCl$_3$ δ 7.60 (2H, d, J=8.8 Hz), 7.5–7.2 (6H, m), 7.05 (2H, d, J=8.8 Hz), 6.76 (1H, s), 6.65 (1H, d, J=9.2 Hz), 6.64 (2H, m), 6.27 (1H, t, J=6.6 Hz), 5.00 (2H, s).

Example 32

1-{4-[5-(4-Cyanophenyloxy-3-methoxy)imidazol-1-ylmethyl]phenyl}-1H-pyridin-2-one Step 1: 4-(4-Bromo-3-methoxyphenyloxy)imidazole Following the procedure as described in Example 31—Step 1, substituting 4-bromophenol with 4-bromo-3-methoxyphenol (Bos, Mary Ellen et al J. Am. Chem. Soc., 9293, 1991), and running the reaction at 100–110 ° C., provided the titled compound as white solid.

$^1$H NMR δ DMSO-$d_6$ 7.48 (1H, s), 7.45 (1H, d, J=8.8 Hz), 6.84 (1H, s), 6.80 (1H, s), 6.45 (1H, br d, J=8.8 Hz), 3.80 (3H, s).

Step 2: 4-(4-Bromo-3-methoxyphenyloxy)-1-trityl-1H-imidazole

Following the procedure as described in Example 31—Step 2, substituting 4-(4-bromophenyloxy)imidazole with 4-(4-bromo-3-methoxyphenyloxy)-imidazole. The titled compound was isolated as white solid.

Step 3: 1-{4-[5-(4-Bromo-3-methoxyphenyloxy)imidazol-1-ylmethyl]-phenyl}-1H-pyridin-2-one Following the procedure as described in Example 31—Step 3, substituting 4-(4-bromophenyloxy)-1-trityl-1H-imidazole with 4-(4-bromo-3-methoxyphenyloxy)-1-trityl-1H-imidazole.

$^1$H NMR CDCl$_3$ δ 7.5–7.2 (m), 6.65 (2H, m), 6.5 (2H, m), 6.25 (1H, t, J=5.4 Hz), 5.01 (2H, s), 3.79 (3H, s).

Step 4: 1-{4-[5-(4-Cayno-3-methoxyphenyloxy)imidazol-1-ylmethyl]-phenyl}-1H-pyridin-2-one Following the procedure as described in Example 31—Step 4, substituting 1-{4-[5-(4-bromophenyloxy)imidazol-1-ylmethyl]-phenyl)-1H-pyridin-2-one with 1-{4-[5-(4-Bromo-3-methoxyphenyl-oxy)imidazol-1-ylmethyl]-phenyl}-1H-pyridin-2-one, and the reaction mixture was heated at 80° C. for 48 h.

$^1$H NMR CDCl$_3$ δ 7.5–7.2 (m), 6.8–6.2 (m), 5.01 (2H, s), 3.83 (3H, s).

Example 33

Preparation of 4-[3-(5-chloro-2-oxo-2H-[1,2']bipyridinyl-5'-ylmethyl)-4,5,6,7-tetrahydro-3H-imidazo[4,5-c]pyridin-4-yl]-benzonitrile Step 1: 4-(4-bromo-phenyl)-4,5,6,7-tetrahydro-3H-imidazo[4,5-c]pyridine Histamine dihydrochloride (3.68 g, 0.02 mole), KOH (3.36 g, 0.06 mole), and 4-bromobenzaldehyde were dissolved in water (250 mL) and 95% EtOH(100 mL). The reaction was heated for 24 h at reflux while being open to the atmosphere. The resulting white precipitate was filtered and dried under vacuum at 40° C. to give the title compound.

Step 2: 4-(4-bromo-phenyl)-6,7-dihydro-4H-imidazo[4,5-c]pyridine-1,5-dicarboxylic acid di-tert-butyl ester 4-(4-bromo-phenyl)-4,5,6,7-tetrahydro-3H-imidazo[4,5-c]pyridine (1.0 g, 3.6 mmol), $Boc_2O$ (1.74 g, 7.9 mmol), and $Et_3N$ (1.1 mL, 7.9 mmol) were dissolved in $CH_2Cl_2$ (35 mL) and stirred overnight at room temperature under Ar. The reaction was washed with water, brine, and dried over anh. $Na_2SO_4$. Filtration, concentration, and silica gel chromatography (1:6 EtOAc/hexane) gave the title compound.

Step 3: 4-(4-cyano-phenyl)-1,4,6,7-tetrahydro-imidazo[4,5-c]pyridine-5-carboxylic acid tert-butyl ester 4-(4-Bromo-phenyl)-6,7-dihydro-4H-imidazo[4,5-c]pyridine-1,5-dicarboxylic acid di-tert-butyl ester (0.55 g, 1.14 mmol) and $Zn(CN)_2$ (0.13 g, 1.14 mmol) were stirred in anh. DMF (10 mL) and degassed with Ar for 15 min. Tetrakis(triphenylphosphine)-palladium(0) was added to the solution and stirred at 80° C. under Ar overnight. The solution was concentrated in vacuo, partitioned between EtOAc and sat. $NaHCO_3$ soln, washed with $H_2O$, brine, and dried over $MgSO_4$. Filtration, concentration, and silica gel chromatography (0–2% MeOH/$CH_2Cl_2$ with $NH_4OH$) gave the title compound.

Step 4: 3-(5-chloro-2-oxo-2H-[1,2']bipyridinyl-5'-ylmethyl)-4-(4-cyano-phenyl)-3,4,6,7-tetrahydro-imidazo[4,5-c]pyridine-5-carboxylic acid tert-butyl ester 4-(4-Cyano-phenyl)-1,4,6,7-tetrahydro-imidazo[4,5-c]pyridine-5-carboxylic acid tert-butyl ester (0.16 g, 0.50 mmol) and 5'-bromomethyl-5-chloro-[1,2']bipyridinyl-2-one (Example 10, Step 2)(0.15 g, 0.50 mmol) were dissolved in DMF (6 mL). NaH (0.02 g, 0.60 mmol) was added and stirred at RT under Ar for 1.5 h. The reaction was concentrated in vacuo and partitioned between EtOAc and satd $NaHCO_3$ soln, washed with $H_2O$, brine, dried ($MgSO_4$), filtered and concentrated to give the title compound as a mixture of racemic regioisomers.

Step 5: 4-[3-(5-chloro-2-oxo-2H-[1,2']bipyridinyl-5'-ylmethyl)-4,5,6,7-tetrahydro-3H-imidazo[4,5-c]pyridin-4-yl]-benzonitrile 3-(5-Chloro-2-oxo-2H-[1,2']bipyridinyl-5'-ylmethyl)-4-(4-cyano-phenyl)-3,4,6,7-tetrahydro-imidazo[4,5-c]pyridine-5-carboxylic acid tert-butyl ester (0.27 g, 0.50 mmol) was dissolved in EtOAc, cooled to 0° C., degassed with Ar, and saturated with anh. HCl gas. The solution was concentated in vacuo and the diastereomers separated using a Chiralcel OD column (25 cm×2 cm, 10/90-0/100Hexane/EtOH with 0.1% DEA, flow 5.0 mL/min) followed by enantiomer seperation using a Delta Pak C18 column (0–100% H2O (0.1% $NH_4HCO_3$)/$CH_3CN$) to give the title compound. $^1H$ NMR ($CDCl_3$); δ 8.01–7.96 (m, 3H), 7.60 (d, 2H, J=8 Hz), 7.54 (s, 1H), 7.37–7.30 (m, 2H), 7.27–7.21 (m, 3H), 6.61 (d, 1H, J=10 Hz), 4.85 (d, 1H, J=16 Hz), 4.79 (s, 1H), 4.45 (s, 1H, J=16 Hz), 3.05–3.01 (m, 2H), 2.80–2.77 (m, 2H). High res. MS Measured=443.1386 Theoretical= 443.1382

Example 34

Preparation of 2-(5-Chloro-2-oxo-2H-[1,2'] bipyridinyl-5'-ylmethoxy)-4-imidazol-1-ylmethyl-benzonitrile Step 1: Preparation of methyl 4-amino-3-hydroxybenzoate Through a solution of 4-amino-3-hydroxybenzoic acid (75 g, 0.49 mol) in 2.0 L of dry $CH_3OH$ at room temperature was bubbled anhydrous HCl gas until the solution was saturated. The solution was stirred for 48 hr, then concentrated in vacuo. The product was partitioned between EtOAc and saturated aq. $NaHCO_3$ solution, and the organic layer was washed with brine, dried ($Na_2SO_4$), and concentrated in vacuo to provide the title. $^1H$ NMR ($CDCl_3$, 400 MHz): d 7.51 (dd, 1H, J=8.1 and 1.9 Hz, ArH); 7.46 (d, 1H, J=1.9 Hz, ArH); 6.66 (d, 1H, J=8.1 Hz, ArH); 5.31 (bs, 1H, OH); 4.13 (bs, 2H, $NH_2$) and 3.85 (s, 3H, $OCH_3$).

Step2: Preparation of methyl 3-hydroxy-4-iodobenzoate

A solution of methyl 4-amino-3-hydroxybenzoate (79 g, 0.47 mol), 3N HCl (750 mL), and THF (250 mL) was cooled to 0° C.

A solution of $NaNO_2$ (35.9 g, 0.52 mol) in 115 mL of water was added over ca. 5 minutes, and the solution was stirred for another 25 minutes. A solution of potassium iodide (312 g, 1.88 mol) in 235 mL of water was added all at once, and the reaction was stirred for an additional 15 minutes. The mixture was poured into EtOAc, shaken, and the layers were separated. The organic phase was washed with water and brine, dried ($Na_2SO_4$), and concentrated in vacuo to provide the crude product (148 g). Purification by column chromatography through silica gel (0%–50% EtOAc/hexane) provided the title compound. $^1H$ NMR ($CDCl_3$, 400 MHz): d 7.75 (d, 1H, J=8.2 Hz, ArH); 7.62 (d, 1H, J=2.0 Hz, ArH); 7.33 (dd, 1H, J=8.2 and 2.0 Hz, ArH); 5.56 (s, 1H, OH) and 3.91 (s, 3H, $OCH_3$).

Step 3: Preparation of methyl 4-cyano-3-hydroxybenzoate

A mixture of methyl 3-hydroxy-4-iodobenzoate (101 g, 0.36 mol) and zinc(II)cyanide (30 g, 0.25 mol) in 400 mL of dry DMF was degassed by bubbling argon through the solution for 20 minutes. Tetrakis(triphenylphosphine) palladium (8.5 g, 7.2 mmol) was added, and the solution was heated to 80° C. for 4 hours. The solution was cooled to room temperature, then stirred for an additional 36 hr. The reaction was poured into EtOAc/water, and the organic layer was washed with brine (4×), dried ($Na_2SO_4$), and concentrated in vacuo to provide the crude product. Purification by column chromatography through silica gel (30%–50% EtOAc/hexane) provided the title compound. $^1H$ NMR ($CDCl_3/CD_3OD$, 400 MHz): d 7.53–7.56 (m, 3H, 3ArH) and 3.93 (s, 3H, $OCH_3$).

Step 4: Preparation of 4-Hydroxymethyl-2-hydroxybenzonitrile

Methyl 4-cyano-2-hydroxybenzoate (0.50 g, 2.82 mmol) was dissolved in dry THF (30 mL), treated with $LiBH_4$ (2.0M solution in THF) (5.64 mL, 11.28 mmol), and heated at reflux for 18 hr. The reaction mixture was cooled to room temperature, poured into 1N HCl solution and extracted with EtOAc (2×). Organics combined and dried ($MgSO_4$), filtered and concentrated to dryness to give the title compound which was used without further purification.

$^1H$ NMR($CD_3OD$) δ 7.45 (d, 1H, J=8 Hz), 6.97 (d, 1H, J=0.7 Hz), 6.88 (dd, 1H, J=0.7, 8 Hz), 4.58 (s, 2H).

Step 5: Preparation of 4-Bromomethyl-2-hydroxybenzonitrile

4-Hydroxymethyl-3-hydroxybenzonitrile (0.20 g, 1.34 mmol) was dissolved in DMF (5 mL): $CH_2Cl_2$ (5 mL), treated with $CBr_4$ (0.666 g, 2.01 mmol) and $Ph_3P$ (0.527 g, 2.01 mmol), and stirred for 1.5 hr at ambient temperature. The reaction mixture was partitioned between EtOAc (100 mL)—$H_2O$ (100 mL), the organic layer separated, dried ($MgSO_4$), filtered, and concentrated to give the title compound after chromatography ($SiO_2$, 15% EtOAc in hexane).

Step 6: Preparation of 2-Hydroxy 4-imidazol-1-ylmethyl-benzonitrile

4-Bromomethyl-2-hydroxybenzonitrile (0.222 g, 1.045 mmol) and imidazole (0.356 g, 5.23 mmol) were stirred in DMF (10 mL) at ambient temperature for 18 hr. The reaction mixture was concentrated in vacuo to remove the DMF, and the residue was chromatographed ($SiO_2$, 2–5% $CH_3OH$ in $CH_2Cl_2$) to give the title compound.

Step 7: Preparation of 2-(5-Chloro-2-oxo-2H-[1,2']bipyridinyl-5'-ylmethoxy)-4-imidazol-1-ylmethyl-benzonitrile 2-Hydroxy 4-imidazol-1-ylmethyl-benzonitrile (0.050 g, 0.25 mmol) and 5'-bromomethyl-5-chloro-[1,2']bipyridinyl-2-one (Example 10 Step 2) (0.079 g, 0.262 mmol) were dissolved in dry DMF (5 mL), treated with $CsCO_3$ (0.123 g, 0.376 mmol) and stirred at ambient temperature for 18 hr. The reaction mixture was partitioned between EtOAc and aqueous satd $NaHCO_3$ solution, the organic layer washed with $H_2O$, brine, and dried ($MgSO_4$). Chromatography ($SiO_2$, 1–4% $CH_3OH$ in $CH_2Cl_2$) gave the title compound.

Anal. $C_{22}H_{16}ClN_5O_2 \cdot 0.40\ H_2O$ Calcd: C, 62.16; H, 3.98; N, 16.48; Found: C, 62.15; H, 3.98; N, 16.19. MS (M+1) 418

Example 35

4-{3-[5-(5-Chloro-2-oxo-2H-pyridin-1-yl)-pyrazin-2-ylmethyl]-3H-imidazol-4-ylmethyl}-benzonitrile Step 1: 5-Bromo-pyrazine-2-carboxylic acid methyl ester A solution of 5-hydroxy-pyrazine-2-carboxylic acid methyl ester (2.56 g, 16.61 mmol) in phosphorous oxybromide 9.9 g, 34.9 mmol) were heated at 90° C. for 70 mins. The reaction was allowed to cool and the resulting solid carefully dissolved in methanol and then the solvent was evaporated in vacuo. The residue was partitioned between EtOAc and sat. $NaHCO_3$ and the organic extracts were washed with brine, dried ($Na_2SO_4$) and evaporated in vacuo. The residue was chromatographed (silica gel, EtOAc:Hexanes 40:60) to afford the title compound.

$^1$H NMR (400 MHz, $CDCl_3$) δ 9.06 (d, J=1.4 Hz,1H), 8.80 (d, J=1.4 Hz,1H), and 4.04 (s, 3H) ppm.

Step 2: 5-(5-chloro-2-oxo-2H-pyridin-1-yl)-pyrazine-2-carboxylic acid methyl ester 5-Chloro-2-pyridinol (1.43 g, 11.05 mmol), the bromide from step 1 (2.39 g, 11.05 mmol), copper (0.021 g, 0.33 mmol) and $K_2CO_3$ (1.68 g, 12.15 mmol) were heated at 120° C. for 3 hrs. Xylene (2 ml) was added and heating was continued at 1 reflux for 2 hrs. The reaction mixture was cooled, diluted with EtOAc and water and the pH was adjusted to 9 with $NH_4Cl$. The aqueous layer was extracted with EtOAc (2x) and the combined organic extracts were washed with brine, dried ($Na_2SO_4$) and evaporated in vacuo. The residue was chromatographed (silica gel, EtOAc: hexanes 20:80 to EtOAc: $CH_2Cl_2$ 10:90 gradient elution) to afford the title compound as a solid.

$^1$H NMR (400 MHz, $CDCl_3$) δ 9.60 (d, J=1.3 Hz, 1H), 9.23 (d, J=1.3 Hz,1H), 8.13 (d, J=2.9 Hz,1H), 7.38(dd, J=9.8 and 2.9 Hz, 1H), 6.66(d, J=9.7 Hz, 1H) and 4.07 (s, 3H) ppm.

Step 3: 5-chloro-1-(5-hydroxymethyl-pyrazin-2-yl)-1H-pyridin-2-one

A solution of the ester from step 2 (1.41 g, 5.317 mmol), in $CH_2Cl_2$ and methanol (1:1 50 ml) at 0° C. was treated with sodium borohydride (2.01 g, 53.17 mmol) and the reaction was stirred at room temperature for 18 hrs. The solvent was evaporated in vacuo and the residue was dissolved in EtOAc and sat. $NaHCO_3$. The aqueous layer was extracted with EtOAc and the combined extracts were dried ($MgSO_4$) and evaporated in vacuo. The residue was chromatographed (silica gel, MeOH: $CH_2Cl_2$ 2:98 to 5:95 gradient elution) to afford the title compound.

$^1$H NMR (400 MHz, $CDCl_3$) δ 9.33 (d, J=1.3 Hz,1H), 8.59(d, J=1.3 Hz,1H), 8.01 (m,1H), 7.37(dd, J=9.7 and 2.8 Hz, 1H), 6.67(d, J=9.7 Hz, 1H) 4.92(d, J=6.7 Hz, 2H) and 2.82 (t, J=6.7 Hz, 1H) ppm.

Step 4: 1-(5-bromomethyl-pyrazin-2-yl)-5-chloro-1H-pyridin-2-one

To a slurry of NBS (0.598 g, 3.36 mmol) in $CH_2Cl_2$ (10 ml) at 0° C. was added methylsulfide (0.296 ml, 4.035 mmol). The slurry was cooled to −20° C. and the alcohol from step 3 (0.532 g, 2.24 mmol) was added followed by $CH_2Cl_2$ (10 ml). The reaction was stirred at 0° C. for 3 hrs and then at room temperature for 24 hrs. The reaction was poured into water and extracted into $CH_2Cl_2$ and the combined extracts were dried ($MgSO_4$) and evaporated in vacuo. The residue was chromatographed (silica gel, EtOAc: $CH_2Cl_2$ 30:70) to afford the title compound.

$^1$H NMR (400 MHz, $CDCl_3$) δ 9.36 (d, J=1.4 Hz,1H), 8.64(d, J=1.3 Hz,1H), 8.02 (d, J=2.9 Hz,1H), 7.36(dd, J=9.7 and 2.8 Hz, 1H), 6.64(d, J=9.7 Hz, 1H) and 4.61(s, 2H) ppm.

Step 5: 4-{3-[5-(5-Chloro-2-oxo-2H-pyridin-1-yl)-pyrazin-2-ylmethyl]-3H-imidazol-4-ylmethyl}-benzonitrile The title compound was prepared according to the procedure described in Step 3, Example 9 using the bromide from step 4.

Analysis: % Calc for $C_{23}H_{16}N_5OF_3 \cdot 1.00\ HCl$, C 57.42, H 3.67, N 19.13; % Found: C 57.67, H 4.03, N 19.17; FABMS 403 ($MH^+$)

Example 36

2-(2-Amino-ethoxy)-4-[5-(5-chloro-2-oxo-2H-[1,2']bipyridinyl-5'-ylmethyl)-imidazol-1-ylmethyl]-benzonitrile Step 1: (2-Bromoethyl)carbamic acid tert-butyl ester 2-Bromoethylamine HBr (2.0 g, 9.76 mmol) was suspended in $CH_2Cl_2$ (50 ml). $Boc_2O$ (2.1 g, 9.76 mmol) was added and the reaction mixture was cooled to 0° C. $Et_3N$ (1.4 ml, 9.76 mmol) was then added and the reaction stirred at 0° C. for 5 min. The reaction mixture was then warmed to room temperature and stirred for 2 hours. The reaction was extracted with water (3x10 mL), brine (10 mL), dried ($MgSO_4$), filtered and concentrated to give the desired compound.

$^1$H NMR (400 MHz, $CDCl_3$) δ 4.98 (bs, 1H, NH), 3.58–3.40 (m, 4H), 1.42 (s, 9H).

Step 2: 3-(2-tert-Butoxycarbonylamino-ethoxy)-4-cyano-benzoic acid methyl ester (2-Bromoethyl)carbamic acid tert-butyl ester (700 mg, 3.12 mmol) from step 1 and 4-cyano-3-hydroxybenzoic acid methyl ester (Example 34 Step 3, 550 mg, 3.12 mmol) was dissolved in DMF (4.5 ml). $Cs_2CO_3$ (2.03 g, 6.24 mmol) was added and the reaction stirred at room temperature for 2 hours. The reaction mixture was filtered through celite and washed with DMF (3x10 mL). The DMF was removed in vacuo. The residue was purified by flash chromatography (12% EtOAc/Hexane) to yield the desired product.

$^1$H NMR (400 MHz, $CDCl_3$) δ 7.70–7.59 (m, 3H), 5.05 (bs, 1H, NH), 4.20 (t, 2H, J=2.25 Hz), 3.61 (m, 2H), 3.98 (s, 3H), 1.24 (s, 9H). FAB MS: m/z 321 ($M^+$+H)

Step 3: [2-(2-cyano-5-hydroxymethyl-phenoxy)-ethyl]-carbamic acid tert-butyl ester 3-(2-tert-Butoxycarbonylamino-ethoxy)-4-cyano-benzoic acid methyl ester from Step 2 (346 mg, 1.08 mmol) was dissolved in THF (5.5 ml). $LiBH_4$ in THF (2M, 1.1 ml, 2.16 mmol) was added. The reaction mixture was heated to 70° C. for 3 hours. The reaction was quenched carefully with 3N HCl and then extracted with EtOAc (3x10 mL). The organic layers were combined, washed with brine, dried ($MgSO_4$), filtered and concentrated to yield the desired compound.

$^1$H NMR (400 MHz, $CDCl_3$) δ 7.48 (d, 1H, d, J=4.54 Hz), 7.10 (s, 1H), 6.98 (d, 1H, J=4.30 Hz), 5.10 (bs, 1H, NH), 4.76 (s, 2H), 4.12 (m, 2H), 3.55 (m, 2H), 1.40 (s, 9H).

Step 4: (2-{5-[5-(5-chloro-2-oxo-2H-[1,2']bipyridinyl-5'-ylmethyl)-imidazol-1-ylmethyl]-2-cyano-phenoxy}-ethyl)-carbamic acid tert-butyl ester To a cooled solution (−78° C.) of [2-(2-cyano-5-hydroxymethylphenoxy)-ethyl]-carbamic acid tert-butyl ester from step 3 (248 mg, 0.85 mmol) and 5-chloro-5'-(1-trityl-1H-imidazol-4-ylmethyl)-[1,2']bipyridinyl-2-one from Example 23, Step 5 (450 mg, 0.85 mmol) in $CH_2Cl_2$ (4.5 ml) was added DIEA (325 μl, 1.87 mmol) followed immediately by the addition of $Tf_2O$ (215 μl, 1.27 mmol). The reaction mixture stirred at −78° C. for 1 hour and was then transferred to an ice bath and stirred at 0° C. for another hour. The solvent was removed in vacuo. The residue was then dissolved in MeOH (4.5 ml) and heated to 60° C. for 4 hours. The MeOH was then removed in vacuo and the residue treated with saturated $NaHCO_3$ and extracted with $CH_2Cl_2$. The organic layer was washed with brine, dried ($MgSO_4$), filtered and concentrated. The residue was purified by flash chromatography with 0 to 4% MeOH($NH_4$OH5%) in $CH_2Cl_2$ to yield the desired product.

$^1$H NMR (400 MHz, $CDCl_3$) δ 8.22 (d, 1H, J=0.55 Hz), 7.97 (dd, 1H, J=0.55, 2.90 Hz), 7.88 (d, 1H, J=8.42 Hz), 7.58 (d, 1H, J=0.92 Hz), 7.53–7.49 (m, 2H), 7.34 (dd, 1H, J=2.90, 9.70 Hz), 7.01 (s, 1H), 6.62 (d, 1H, J=9.71 Hz), 6.56 (d, 1H, J=7.87 Hz), 6.48 (s, 1H), 5.18 (bs, 1H, NH), 5.00 (s, 2H), 4.02 (t, 2H, J=5.40 Hz), 4.84 (s, 2H), 3.57 (q, 2H, J=5.40, 10.9 Hz), 1.40 (s, 9H).

Step 5: 2-(2-Amino-ethoxy)-4-[5-(5-chloro-2-oxo-2H-[1,2']bipyridinyl-5'-ylmethyl)-imidazol-1-ylmethyl]-benzonitrile (2-{5-[5-(5-chloro-2-oxo-2H-[1,2']bipyridinyl-5'-ylmethyl)-imidazol-1-ylmethyl]-2-cyano-phenoxy}-ethyl)-carbamic acid tert-butyl ester from step 4 (260 mg, 0.46 mmol) was dissolved in MeOH (15 ml) and cooled to 0° C. HCl(g) was then bubbled into the solution until saturated. The reaction mixture was allowed to warm up to room temperature. The solvent was removed in vacuo to yield the final product.

$^1$H NMR (400 MHz, $CD_3OD$) δ 9.18 (s, 1H), 8.18 (bs, 1H), 7.95 (d, 1H, J=4.59 Hz), 7.72–7.52 (m, 5H), 7.03 (bs, 1H), 6.78 (d, 1H, J=12 Hz), 6.64 (d, 1H, J=12 Hz), 5.61 (s, 2H), 4.34 (t, 2H, J=6.54 Hz), 4.24 (s, 2H), 3.44 (t, 2H, J=6.54 Hz).

Analysis calculated for ($C_{24}H_{21}N_6O_2Cl.2.5$ HCl.0.55 $CH_2Cl_2$); C,49.24; H,4.14; N,14.04; Found C,49.06; H,4.54; N,13.74; FAB MS: m/z 461 (M$^+$+H)

Example 37

4-[5-(5-Chloro-2-oxo-2H-[1,2']bipyridinyl-5'-ylmethyl)-imidazol-1-ylmethyl]-2-(2-dimethylamino-ethoxy)-benzonitrile 2-(2-Amino-ethoxy)-4-[5-(5-chloro-2-oxo-2H-[1,2']bipyridinyl-5'-ylmethyl)-imidazol-1-ylmethyl]-benzonitrile (L-824,459, 43 mg, 0.09 mmol) was dissolved in THF (1 mL) and $CH_2O$ (37% wt. in $H_2O$, 14 μl, 0.18 mmol) was added. The solution was treated with $NaCNBH_3$ (11.7 mg, 0.18 mmol) and the reaction mixture stirred at room temperature for 2 hours. 10% aqueous NaOH was added to the mixture and extracted with $CH_2Cl_2$. The water layer was extracted with $CH_2Cl_2$ (2×10 mL) and the combined organic layers were dried ($MgSO_4$), filtered and concentrated. Flash chromatography [8% MeOH($NH_4$OH5%)/$CH_2Cl_2$] yielded the final product.

$^1$H NMR (400 MHz, $CDCl_3$) δ 8.23 (bs, 1H), 7.98 (d, 1H, J=2.5 Hz), 7.87 (d, 1H, J=7.5 Hz), 7.58 (s, 1H), 7.51–7.48 (m, 2H), 7.33 (dd, 1H, J=7.5, 2.5 Hz), 6.98 (s, 1H), 6.63–6.55 (m, 2H), 6.45 (bs, 1H), 4.99 (s, 2H), 4.04 (t, 2H, J=6.2 Hz), 3.80 (s, 2H), 2.77 (t, 2H, J=6.2 Hz), 2.27 (s, 6H).

Analysis calculated for ($C_{26}H_{25}N_6O_2Cl.2.45$ HCl.1.2 $CH_2Cl_2$); C,48.02; H,4.42; N,12.36; Found C,47.51; H,5.22; N,12.95; FAB MS: m/z 489 (M$^+$+H)

Example 38

N-(2-{5-[5-(5-chloro-2-oxo-2H-[1,2']bipyridinyl-5'-ylmethyl)-imidazol-1-ylmethyl]-2-cyano-phenoxy}-ethyl)-acetamide 2-(2-Amino-ethoxy)-4-[5-(5-chloro-2-oxo-2H-[1,2']bipyridinyl-5'-ylmethyl)-imidazol-1-ylmethyl]-benzonitrile (L-824,459, 50 mg, 0.11 mmol) was dissolved in $CH_2Cl_2$ (550 tl) and treated with acetic anhydride (208 μl, 0.22 mmol). DIEA was then added until pH=7–8. The reaction mixture was stirred at room temp. for 2 hours. Saturated $NaHCO_3$ was added (10 mL) and the solution was extracted with $CH_2Cl_2$ (2×10 mL). The organic layer was washed with brine, dried ($MgSO_4$), filtered, and concentrated to yield the final product.

$^1$H NMR (400 MHz, $CDCl_3$) δ 8.17 (d, 1H, J=2.2 Hz), 7.96 (d, 1H, J=2.8 Hz), 7.87 (d, 1H, J=8.4 Hz), 7.59 (s, 1H), 7.51–7.48 (m, 2H), 7.33 (dd, 1H, J=10.0, 2.8 Hz), 7.03 (s, 1H), 6.62–6.58 (m, 2H), 6.40 (bs, 1H), 5.02 (s, 2H), 4.01 (t, 2H, J=5.13 Hz), 3.85 (s, 2H), 3.67 (q, 2H, J=5.3, 10.3 Hz), 2.03 (s, 3H).

Analysis calculated for ($C_{26}H_{23}N_6O_3Cl.2.5H_2O.1.45$ $CH_2Cl_2$); C,49.12; H,4.64; N,12.52; Found C,49.12; H,4.91; N,12.52; FAB MS: m/z 503 (M$^+$+H)

Example 39

3-Chloro-N-(2-{5-[5-(5-chloro-2-oxo-2H-[1,2']bipyridinyl-5'-ylmethyl)-imidazol-1-ylmethyl]-2-cyano-phenoxy}-ethyl)-benzamide 2-(2-Amino-ethoxy)-4-[5-(5-chloro-2-oxo-2H-[1,2']bipyridinyl-5'-ylmethyl)-imidazol-1-ylmethyl]-benzonitrile (L-824,459, 75 mg, 0.16 mmol) was dissolved in DMF (800 μl) and treated with 3-chlorobenzoylchloride (20 μl, 0.18 mmol). The reaction mixture was stirred at room temp. for 2 hours. The solvent was removed in vacuo and the crude product purified by flash chromatography [4% MeOH ($NH_4OH$ 5%)/$CH_2Cl_2$] to yield the final product.

$^1$H NMR (400 MHz, $CD_3OD$) δ 8.17 (s, 1H), 7.89 (d, 1H, J=2.93 Hz), 7.84 (s, 1H), 7.76 (d, 1H, 7.32 Hz), 7.61–7.41 (m, 7H), 6.99 (s, 1H), 6.72 (s, 1H), 6.56 (dd, 2H, J=9.0, 16.2 Hz), 5.28 (s, 2H), 4.21 (t, 2H, J=5.61 Hz), 4.01 (s, 2H), 3.76 (t, 2H, J=5.3, 10.3 Hz). Analysis calculated for ($C_{31}H_{24}N_6O_3Cl_2.2.50$ HCl.1.85$H_2O$); C,51.43; H,4.20; N,11.61; Found: C,51.44; H,4.09; N,11.58; FAB MS: m/z 600 (M$^+$+H)

Example 40

4-[5-(5-Chloro-2-oxo-2H-[1,2']bipyridinyl-5'-ylmethyl)-imidazol-1-ylmethyl]-2-(2,2,2-trifluoro-ethoxy)-benzonitrile Step 1: 4-Cyano-3-(2,2,2-trifluoro-ethoxy)-benzoic acid methyl ester $CF_3SO_2Cl$ (2.7 ml, 25.5 mmol) was added under argon atmosphere to diethylether (60 ml) and cooled to 0° C. $CF_3CH_2OH$ (1.8 ml, 25.5 mmol) and $Et_3N$ (3 ml, 21.25 mmol) were then added dropwise. The reaction mixture was stirred at 0° C. for 0.5 hour. The reaction was cooled to −20° C. to maximize ppt. of $Et_3NHCl$. The mixture was filtered and washed with cold diethylether (1×20 mL). The filtrate was concentrated to approx. ½ the volume in vacuo, keeping the flask at room temp. to minimize the loss of trifluoromethanesulfonic acid 2,2,2-trifluoro-ethyl ester. The resulting solution was treated with 4-cyano-3-hydroxybenzoic acid methyl ester, Example 34, Step 3 (1.5 g, 8.5 mmol) in DMF (28 ml) containing $Cs_2CO_3$ (5 g, 21.25 mmol). The reaction mixture stirred for several hours. The mixture was filtered and washed with DMF (3×5 mL). The solvent was removed in vacuo and the residue was purified by flash chromatography (5% EtOAc/Hexane) to yield the desired product.

$^1$H NMR (400 MHz, $CDCl_3$) δ 7.81 (dd, 1H, J=2.0, 8.54 Hz), 7.71 (d, 1H, J=8.54 Hz), 7.54 (d, 1H, 2.0 Hz), 4.55 (q, 2H, J=3.6, 6.5 Hz), 3.98 (s, 3H).

Step 2: 2-(2,2,2-Trifluoro-ethoxy)-4-hydroxymethyl-benzonitrile

4-Cyano-3-(2,2,2-trifluoro-ethoxy)-benzoic acid methyl ester from step 1 (1.6 g, 6.2 mmol) was dissolved in THF (62 ml). $LiBH_4$ in THF (2M, 6.2 ml, 12.4 mmol) was added. The reaction mixture was heated to 70° C. for 3 hours. The reaction was quenched carefully with 3N HCl and then extracted with EtOAc (3×10 mL). The organic layers were combined, washed with brine, dried ($MgSO_4$) filtered and concentrated to yield the desired product.

$^1$H NMR (400 MHz, $CDCl_3$) δ 7.60 (d, 5.2 Hz), 7.18 (m, 2H), 4.82 (s, 2H), 4.55 (q, 2H, J=3.6, 6.5 Hz). FAB MS: m/z 232 ($M^+$+H)

Step 3: 4-Bromomethyl-2-(2,2,2-trifluoro-ethoxy)-benzonitrile 2-(2,2,2-Trifluoro-ethoxy)-4-hydroxymethyl-benzonitrile (1.4 g, 6.1 mmol) was dissolved in THF (31 ml) and treated with $Ph_3P$ (2.4 g, 9.15 mmol) followed by $CBr_4$ (3 g, 9.15 mmol). The reaction mixture was stirred at room temp. for 2 hours. The solvent was removed in vacuo and the residue purified by flash chromatography (20% EtOAc/Hexane) to yield the desired product.

$^1$H NMR (400 MHz, $CDCl_3$) δ 7.60 (d, 1H, J=8.80 Hz), 7.15 (dd, 1H, J=1.80, 8.80 Hz), 7.06 (d, 1H, J=1.80 Hz), 4.53 (q, 2H, J=3.4, 6.1 Hz), 4.45 (s, 2H). FAB MS: m/z 295 ($M^+$+H)

Step 4: 4-[5-(5-Chloro-2-oxo-2H-[1,2']bipyridinyl-5'-ylmethyl)-imidazol-1-ylmethyl]-2-(2,2,2-trifluoro-ethoxy)-benzonitrile 4-Bromomethyl-2-(2,2,2-trifluoro-ethoxy)-benzonitrile from Step 3 (200 mg, 0.68 mmol) and 5-chloro-5'-(1-trityl-1H-imidazol-4-ylmethyl)-[1,2']bipyridinyl-2-one from Example 23, Step 5 (360 mg, 0.68 mmol) were dissolved in $CH_3CN$ (3.5 ml) and heated to 60° C. for 4 hours. The solvent was removed in vacuo and redissolved in MeOH (3.5 ml). The reaction mixture was heated to 60° C. for 3 more hours. The solvent was removed in vacuo and the crude residue purified by flash chromatography [4% MeOH (5% $NH_4OH$)/$CH_2Cl_2$] to yield the final product.

$^1$H NMR (400 MHz, $CDCl_3$) δ 8.23 (d, 1H, J=2.2 Hz), 7.94 (d, 1H, J=2.8 Hz), 7.89 (d, 1H, J=8.4 Hz), 7.61 (s, 1H), 7.57 (d, 1H, J=9.0 Hz), 7.52 (dd, 1H, J=9.0, 2.2 Hz), 7.34 (dd, 1H, J=10.0, 2.8 Hz), 7.03 (s, 1H), 6.21 (d, 1H, J=10.2 Hz), 6.0 (d, 1H, J=11.6 Hz), 6.46 (bs, 1H), 5.01 (s, 2H), 4.40 (q, 2H, J=3.5, 6.2 Hz), 3.82 (s, 2H).

Analysis calculated for ($C_{24}H_{17}N_5O_2F_3Cl.1.45$ HCl.1.10 $CH_2Cl_2$); C,46.65; H,3.22; N,10.84; Found C,46.67; H,3.42; N,10.84; FAB MS: m/z 500 ($M^+$+H)

Example 41

2-Benzyloxy-4-[5-(5-chloro-2-oxo-2H-[1,2']bipyridinyl-5'-ylmethyl)-imidazol-1-ylmethyl]-benzonitrile Step 1: 3-Benzyloxy-4-cyano-benzoic acid methyl ester 4-cyano-3-hydroxybenzoic acid methyl ester, Example 34, Step 3 (300 mg, 1.7 mmol) was dissolved in DMF (8.5 ml) and treated with benzyl bromide (200 µl, 1.7 mmol). $Cs_2CO_3$ (610 mg, 1.87 mmol) was then added and the reaction mixture stirred at room temp. for 6 hours. The mixture was filtered and washed with DMF (3×10 mL). The solvent was removed in vacuo and the residue was purified by flash chromatography (15% EtOAc/Hexane) to yield the desired product.

$^1$H NMR (400 MHz, $CDCl_3$) δ 7.71–7.65 (m, 3H), 7.50–7.47 (m, 2H), 7.43–7.35 (m, 3H), 5.28 (s, 2H), 3.98 (s, 3H).

Step 2: 2-Benzyloxy-4-hydroxymethyl-benzonitrile

3-Benzyloxy-4-cyano-benzoic acid methyl ester from step 1 (400 mg, 1.5 mmol) was dissolved in THF (7.5 ml). $LiBH_4$ in THF (2M, 1.5 ml, 3 mmol) was added. The reaction mixture was heated at 70° C. for 3 hours. The reaction was quenched carefully with 3N HCl and then extracted with EtOAc (3×10 mL). The organic layers were combined, washed with brine, dried ($MgSO_4$), filtered and concentrated to yield the desired product.

$^1$H NMR (400 MHz, $CDCl_3$) δ 7.55 (d, 1H, J=6.45 Hz), 7.49–7.44 (m, 2H), 7.42–7.32 (m, 3H), 7.08 (s, 1H), 6.6.95 (d, 1H, J=6.80 Hz), 5.22 (s, 2H), 4.71 (s, 2H).

Step 3: 2-Benzyloxy-4-[5-(5-chloro-2-oxo-2H-[1,2']bipyridinyl-5'-ylmethyl)-imidazol-1-ylmethyl]-benzonitrile To a cooled solution (–78° C.) of 2-benzyloxy-4-hydroxymethyl-benzonitrile from step 2 (100 mg, 0.42 mmol) and 5-chloro-5'-(1-trityl-1H-imidazol-4-ylmethyl)-[1,2']bipyridinyl-2-one from Example 23, Step 5 (221 mg, 0.42 mmol) in $CH_2Cl_2$ (2.1 ml) was added DIEA (325 µl, 0.92 mmol) followed immediately by the addition of $Tf_2O$ (160 µl, 0.63 mmol). The reaction mixture was stirred at –78° C. for 1 hour and was then transferred to an ice bath and stirred at 0° C. for another hour. The solvent was removed in vacuo. The residue was then dissolved in MeOH and heated to 60° C. for several hours. The MeOH was then removed in vacuo and the residue treated with saturated $NaHCO_3$ (5 mL) and extracted with $CH_2Cl_2$ (2×10 mL). The organic layer was washed with brine, dried ($MgSO_4$), filtered and concentrated. The residue was purified by flash chromatography [4% MeOH(5% $NH_4OH$)/$CH_2Cl_2$] to yield the final product.

$^1$H NMR (400 MHz, $CDCl_3$) δ 8.16 (d, 1H, J=2.20 Hz), 7.97 (d, 1H, J=3.75), 7.86 (d, 1H, J=8.22 Hz), 7.54 (s, 2H), 7.43–7.31 (m, 7H), 6.98 (s, 1H), 6.61 (d, 2H, J=9.15 Hz), 6.40 (s, 1H), 5.12 (s, 2H), 4.95 (s, 2H), 3.67 (s, 2H).

Analysis calculated for ($C_{29}H_{22}N_5O_2Cl.1.4$ HCl.1.6$H_2O$); C,59.25; H,4.56; N,11.91; Found C,59.26; H,4.57; N,12.01; FAB MS: m/z 508 ($M^+$+H)

Example 42

4-[5-(5-Chloro-2-oxo-2H-[1,2']bipyridinyl-5'-ylmethyl)-imidazol-1-ylmethyl]-2-phenethyloxy-benzonitrile Step 1: 4-Cyano-3-phenethyloxy-benzoic acid methyl ester 4-cyano-3-hydroxybenzoic acid methyl ester, Example 34, Step 3 (300 mg, 1.7 mmol) was dissolved in DMF (8.5 ml) and treated with phenethylchloride (224 µl, 1.7 mmol). $Cs_2CO_3$ (610 mg, 1.87 mmol) was then added and the reaction mixture stirred at room temp. for 16 hours. The mixture was filtered and washed with DMF(3×10 mL). The solvent was removed in vacuo and the residue was purified by flash chromatography (10% EtOAc/Hexane) to yield the desired product.

¹H NMR (400 MHz, CDCl₃) δ 7.65–7.62 (m, 2H), 7.58 (s, 1H), 7.37–7.35 (m, 5H), 4.33 (t, 2H, J=6.50 Hz), 3.94 (s, 3H), 3.20 (t, 2H, J=6.78 Hz).

Step 2: 4-Hydroxymethyl-2-phenethyloxy-benzonitrile

3-Benzyloxy-4-cyano-benzoic acid methyl ester from step 1 (84 mg, 0.30 mmol) was dissolved in THF (1.5 ml). LiBH₄ in THF (2M, 300 μl, 0.60 mmol) was added. The reaction mixture was heated at 70° C. for 3 hours. The reaction mixture was quenched carefully with 3N HCl and then extracted with EtOAc (3×10 mL). The organic layers were combined, washed with brine, dried (MgSO₄), filtered and concentrated to yield the desired product.

Step 3: 4-[5-(5-Chloro-2-oxo-2H-[1,2']bipyridinyl-5'-ylmethyl)-imidazol-1-ylmethyl]-2-phenethyloxy-benzonitrile To a cooled solution (–78° C.) of 4-hydroxymethyl-2-phenethyloxy-benzonitrile from step 2 (65 mg, 0.26 mmol) and 5-chloro-5'-(1-trityl-1H-imidazol-4-ylmethyl)-[1,2']bipyridinyl-2-one from Example 23 Step 5 (136 mg, 0.26 mmol) in CH₂Cl₂ (2 ml) was added DIEA (100 μl, 0.56 mmol) followed immediately by the addition of Tf₂O (65 μl, 0.39 mmol). The reaction mixture was stirred at –78° C. for 1 hour and was then transferred to an ice bath and stirred at 0° C. for another hour. The solvent was removed in vacuo. The residue was then dissolved in MeOH (2 ml) and heated to 60° C. for several hours. The MeOH was then removed in vacuo and the residue treated with saturated aqueous NaHCO₃ (5 mL) and extracted with CH₂Cl₂ (2×10 mL). The organic layer was washed with brine, dried (MgSO₄), filtered and concentrated. The residue was purified by flash chromatography [4% MeOH(5% NH₄OH)/CH₂Cl₂] to yield the final product.

¹H NMR (400 MHz, CDCl₃) δ 8.21 (d, 1H, J=1.38 Hz), 7.97 (d, 1H, J=2.9, 0.6), 7.86 (d, 1H, J=8.24 Hz ), 7.56–7.48 (m, 3H), 7.37–7.31 (m, 6H), 6.99 (s, 1H), 6.61 (dd, 1H, J=9.75, 0.6 Hz), 6.57 (d, 1H, J=7.87 Hz), 6.37 (s, 1H), 6.49 (s, 2H), 4.12 (t, 2H, J=6.78 Hz), 3.72 (s, 2H), 3.14 (t, 2H, J=6.69 Hz).

Analysis calculated for ($C_{30}H_{24}N_5O_2Cl$.0.7 HCl.1.65 $H_2O$); C,62.42; H,4.89; N,12.13; Found C,62.41; H,4.90; N,12.00; FAB MS: m/z 523 (M⁺+H)

Example 43

4-[5-(5-Chloro-2-oxo-2H-[1,2']bipyridinyl-5'-ylmethyl)-imidazol-1-ylmethyl]-2-(4-phenyl-butoxy)-benzonitrile Step 1: 4-Cyano-3-(4-phenyl-butoxy)-benzoic acid methyl ester 4-Cyano-3-hydroxybenzoic acid methyl ester, Example 34 Step 3 (300 mg, 1.7 mmol) was dissolved in DMF (85 ml) and treated with phenylbutylchloride (287 mg, 1.7 mmol). Cs₂CO₃ (610 mg, 1.87 mmol) was then added and the reaction mixture stirred at room temp. for 18 hours. The mixture was filtered and washed with DMF (3×10 mL). The solvent was removed in vacuo and the residue was purified by flash chromatography (10% EtOAc/Hexane) to yield desired product.

¹H NMR (400 MHz, CDCl₃) δ 7.67–7.64 (m, 2H), 7.59 (s, 1H), 7.34–7.18 (m, 5H), 4.15 (t, 2H, J=5.55 Hz), 3.96 (s, 2H), 2.75 (t, 2H, J=6.52 Hz), 1.85–1.83 (m, 4H).

Step 2: 4-Hydroxymethyl-2-(4-phenyl-butoxy)-benzonitrile

4-Cyano-3-(4-phenyl-butoxy)-benzoic acid methyl ester from step 1 (285.1 mg, 0.92 mmol) was dissolved in THF (4.6 ml). LiBH₄ in THF (2M, 923 μl, 1.85 mmol) was added. The reaction mixture was heated to 70° C. for 3 hours. The reaction mixture was quenched carefully with 3N HCl and then extracted with EtOAc (3×10 mL). The organic layers were combined, washed with brine, dried (MgSO₄), filtered and concentrated to yield the desired product.

¹H NMR (400 MHz, CDCl₃) δ 7.51 (d, 1H, J=7.54 Hz), 7.30–7.15 (m, 5H), 6.98 (s, 1H), 6.93 (d, 1H, J=6.98 Hz), 4.75 (s, 2H), 4.08 (t, 2H, J=5.50 Hz), 2.65 (t, 2H, J=6.52 Hz), 1.90–1.75 (m, 4H).

Step 3: 4-[5-(5-Chloro-2-oxo-2H-[1,2']bipyridinyl-5'-ylmethyl)-imidazol-1-ylmethyl]-2-(4-phenyl-butoxy)-benzonitrile To a cooled solution (–78° C.) of 4-hydroxymethyl-2-(4-phenyl-butoxy)-benzonitrile from step 2 (100 mg, 0.36 mmol) and 5-chloro-5'-(1-trityl-1H-imidazol-4-ylmethyl)-[1,2']bipyridinyl-2-one from Example 23 Step 5 (188 mg, 0.36 mmol) in CH₂Cl₂ (2 ml) was added DIEA (136 μl, 0.78 mmol) followed immediately by the addition of Tf₂O (90 μl, 0.53 mmol). The reaction mixture stirred at –78° C. for 1 hour and was then transferred to an ice bath and stirred at 0° C. for another hour. The solvent was removed in vacuo. The residue was then dissolved in MeOH (2 ml) and heated to 60° C. for several hours. The MeOH was then removed in vacuo and the residue treated with saturated NaHCO₃ (5 mL) and extracted with CH₂Cl₂ (2×10 mL). The organic layer was washed with brine, dried (MgSO₄), filtered and concentrated. The residue was purified by flash chromatography [4% MeOH(5% NH₄OH)/CH₂Cl₂] to yield the final product.

¹H NMR (400 MHz, CDCl₃) δ 8.21 (d, 1H, J=1.72 Hz), 7.97 (d, 1H, J=2.93), 7.88 (d, 1H, J=9.55 Hz ), 7.57 (s, 1H), 7.50 (d, 2H, J=8.50 Hz), 7.35–7.19 (m, 6H), 6.99 (s, 1H), 6.61–6.55 (m, 2H), 6.38 (s, 1H), 4.98 (s, 2H), 3.93 (t, 2H, J=5.37 Hz), 3.80 (s, 2H), 2.70 (t, 2H, J=6.34 Hz), 1.85–1.83 (m, 4H).

Analysis calculated for ($C_{32}H_{28}N_5O_2Cl$.1.0 HCl.1.25 $H_2O$); C,63.10; H,5. 21; N,11.50; Found: C,63.08; H,5.22; N,11.19; FAB MS: m/z 553 (M⁺+H)

Example 44

4-[5-(5-chloro-2-oxo-2H-[1,2']bipyridinyl-5'-ylmethyl)-imidazol-1-ylmethyl]-2-(3-phenyl-propoxy)-benzonitrile Step 1: 2-Hydroxy-4-hydroxymethyl-benzonitrile 4-cyano-3-hydroxybenzoic acid methyl ester, Example 34, Step 3 (2.5 g, 14 mmol) was dissolved in THF (70 ml). LiBH₄ in THF (2M, 14 ml, 28 mmol) was added. The reaction mixture was heated to 70° C. for 60 hrs. The reaction mixture was quenched carefully with 3N HCl. The solvent was removed in vacuo and the crude material was purified by flash chromatography [10% MeOH(5% NH₄OH)/CH₂Cl₂] to yield the desired product.

¹H NMR (400 MHz, CD₃OD) δ 7.44 (d, 1H, J=8.6 Hz), 6.96 (s, 1H), 6.86 (d, 1H, J=8.48 Hz), 4.59 (s, 2H).

Step 2: 4-(tert-Butyl-dimethyl-silanyloxymethyl)-2-hydroxy-benzonitrile

2-Hydroxy-4-hydroxymethyl-benzonitrile from step 1 (1.16 g, 4.58 mmol) was dissolved in CH₂Cl₂ (23 ml) and treated with tert-butyldimethyl-silylchloride (345 mg, 9.16 mmol). Et₃N (1.3 ml, 9.16 mmol) was added and the reaction mixture stirred at room temp. for 10 hours. The reaction was stopped when 50% complete and the solvent was removed in vacuo. The crude material was purified by flash chromatography (100% CH₂Cl₂) to yield the desired product.

¹H NMR (400 MHz, CDCl₃) δ 7.50 (d, 1H, J=7.4 Hz), 6.95 (d, 1H, J=8.0 Hz), 6.92 (s,1H), 4.70 (d, 2H, J=4.6 Hz), 1.10 (s, 9H), 0.28 (s, 6H).

Step 3: 4-Hydroxymethyl-2-(3-phenyl-propoxy)-benzonitrile 4-(tert-Butyl-dimethyl-silanyloxymethyl)-2-hydroxy-benzonitrile from step 2 (50 mg, 0.19 mmol) was dissolved in DMF (1 ml) and treated with phenylpropylbromide (29 μl, 0.19 mmol). $Cs_2CO_3$ (68 mg, 0.21 mmol) was then added and the reaction mixture stirred at room temp. for 14 hours. The mixture was filtered and washed with DMF (3×10 mL). The solvent was removed in vacuo and the residue was purified by flash chromatography (10% EtOAc/Hexane) to yield desired product.

$^1$H NMR (400 MHz, $CDCl_3$) δ 7.28–7.15 (m, 5H), 7.48 (d, 1H, J=6.54 Hz) 6.95–6.87 (m, 2H), 4.65 (s, 2H), 4.05 (t, 2H, J=6.10 Hz), 2.80 (t, 2H, J=8.2 Hz), 2.15 (m, 2H). FAB MS: 268 m/z ($M^+$+H)

Step 4: 4-[5-(5-chloro-2-oxo-2H-[1,2']bipyridinyl-5'-ylmethyl)-imidazol-1-ylmethyl]-2-(3-phenyl-propoxy)-benzonitrile To a cooled solution (−78° C.) of 4-hydroxymethyl-2-(3-phenyl-propoxy)-benzonitrile from step 3 (35 mg, 0.13 mmol) and 5-chloro-5'-(1-trityl-1H-imidazol-4-ylmethyl)-[1,2']bipyridinyl-2-one from Example 23, Step 5 (70 mg, 0.13 mmol) in $CH_2Cl_2$ (650 μl) was added DIEA (50 μl, 0.27 mmol) followed immediately by the addition of $Tf_2O$ (33 μl, 0.19 mmol). The reaction mixture was stirred at −78° C. for 1 hour and was then transferred to an ice bath and stirred at 0° C. for another hour. The solvent was removed in vacuo. The residue was then dissolved in MeOH (650 μl) and heated to 60° C. for 14 hours. The MeOH was then removed in vacuo and the residue treated with saturated $NaHCO_3$ (5 mL) and extracted with $CH_2Cl_2$ (2×10 mL). The organic layer was washed with brine, dried ($MgSO_4$), filtered and concentrated. The residue was purified by flash chromatography [4% MeOH(5% $NH_4OH$)/$CH_2Cl_2$] to yield the final product.

$^1$H NMR (400 MHz, $CDCl_3$) δ 8.21 (d, 1H, J=2.38 Hz), 7.91 (d, 1H, J=2.93 Hz), 7.87 (d, 1H, J=J=8.24 Hz), 7.57 (s, 1H), 7.52–7.48 (m, 3H), 7.35–7.18 (m, 5H), 6.98 (s, 1H), 6.60 (d, 1H, J=9.30 Hz), 6.56 (d, 1H, J=7.87 Hz), 6.36 (s, 1H), 4.96 (s, 2H), 3.92 (t, 2H, J=6.23 Hz), 3.79 (s, 2H), 2.84 (t, 2H, J=8.33 Hz), 2.13 (q, 2H, J=15.8, 7.0 Hz).

Analysis calculated for ($C_{31}H_{26}N_5O_2Cl.2.20$ HCl.2.10 $H_2O$); C,56.92; H,4.99; N,10.71; Found: C,56.95; H,5.0; N, 10.58; FAB MS: m/z 537 ($M^+$+H)

Example 45

4-[5-(5-Chloro-2-oxo-2H-[1,2']bipyridinyl-5'-ylmethyl)-imidazol-1-ylmethyl]-2-methoxy-benzonitrile Step 1: 4-Cyano-3-methoxy-benzoic acid methyl ester 4-cyano-3-hydroxybenzoic acid methyl ester, Example 34, Step 3 (4 g, 22.6 mmol) was dissolved in DMF (115 ml) and treated with NaH (1 g, 45.2 mmol) and $CH_3I$ (2.8 ml, 45.2 mmol). The reaction mixture was stirred at room temperature for 24 hours. EtOAc was added to the mixture and extracted with 5% citric acid (2×10 mL), saturated $NaHCO_3$ (2×10 mL) and brine (1×10 mL). The organic layer was dried ($MgSO_4$), filtered, and concentrated to yield the desired product.

$^1$H NMR (400 MHz, $CDCl_3$) δ 7.68–7.62 (m, 3H), 4.00 (s, 3H), 3.95 (s, 3H).

Step 2: 4-Hydroxymethyl-2-methoxy-benzonitrile

4-Cyano-3-methoxy-benzoic acid methyl ester from step 1 (4.7 g, 25 mmol) was dissolved in THF (125 ml). $LiBH_4$ in THF (2M, 25 ml, 50 mmol) was added. The reaction mixture was heated at 70° C. for 3 hours. The reaction mixture was quenched carefully with 3N HCl and then extracted with EtOAc (3×10 mL). The organic layers were combined, washed with brine, dried ($MgSO_4$), filtered and concentrated to yield the desired product.

$^1$H NMR (400 MHz, $CDCl_3$) δ 7.52 (d, 1H, J=4.98 Hz), 7.05 (s, 1H), 6.95 (d, 1H, J=7.0 Hz), 4.75 (d, 2H, J=6.38 Hz), 3.95 (s, 3H).

Step 3: 4-[5-(5-Chloro-2-oxo-2H-[1,2']bipyridinyl-5'-ylmethyl)-imidazol-1-ylmethyl]-2-methoxy-benzonitrile To a cooled solution (−78° C.) of 4-hydroxymethyl-2-methoxy-benzonitrile from step 2 (100 mg, 0.61 mmol) and 5-chloro-5'-(1-trityl-1H-imidazol-4-ylmethyl)-[1,2'] bipyridinyl-2-one from Example 23, Step 5 (325 mg, 0.613 mmol) in $CH_2Cl_2$ (3 ml) was added DIEA (235 μl, 1.35 mmol) followed immediately by the addition of $Tf_2O$ (103 μl, 0.92 mmol). The reaction mixture was stirred at −78° C. for 1 hour and was then transferred to an ice bath and stirred at 0° C. for another hour. The solvent was removed in vacuo. The residue was then dissolved in MeOH (3 ml) and heated to 60° C. for 8 hours. The MeOH was then removed in vacuo and the residue treated with saturated $NaHCO_3$ (5 mL) and extracted with $CH_2Cl_2$ (2×10 mL). The organic layer was washed with brine, dried ($MgSO_4$), filtered and concentrated. The residue was purified by flash chromatography [4% MeOH(5% $NH_4OH$)/$CH_2Cl_2$] to yield the final product.

$^1$H NMR (400 MHz, $CDCl_3$) δ 9.52 (bs, 1H), 8.29 (bs, 1H), 7.94 (d, 1H, J=2.38 Hz), 7.89–7.83 (m, 2H), 7.65–7.61 (m, 1H), 7.54 (d, 1H, J=7.69 Hz), 7.37 (d, 1H, J=8.93 Hz), 7.10 (s, 1H), 6.99 (s, 1H), 6.72 (d, 1H, J=7.78 Hz), 6.60 (d, 1H, J=9.71 Hz), 5.46 (s, 2H), 3.95 (s, 2H), 3.93 (s, 3H).

Analysis calculated for ($C_{23}H_{18}N_5O_2Cl.0.90$ HCl.1.35 $H_2O$); C,56.49; H,4.45; N,14.32; Found: C,56.43; H,4.45; N, 14.35; FAB MS: m/z 432 ($M^+$+H)

Example 46

5-[5-(5-Chloro-2-oxo-2H-[1,2']bipyridinyl-5'-ylmethyl)-imidazol-1-ylmethyl]-biphenyl-2-carbonitrile Step 1: 4-Cyano-3-(trifluoromethanesulfonyloxy)-benzoic acid methyl ester 4-cyano-3-hydroxybenzoic acid methyl ester, Example 34, Step 3 (2 g, 11.3 mmol) was dissolved in $CH_2Cl_2$ (57 ml) and cooled to 0° C. in an ice bath. The mixture was treated with $Et_3N$ (3 ml, 22.6 mmol) followed by the addition of $Tf_2O$ (1.9 ml, 11.3 mmol). The reaction mixture was warmed to room temp. and stirred for 4 hours. Saturated $NaHCO_3$ (10 mL) was added and the mixture was extracted with EtOAc (2×10 mL). The organic layers were combined and dried ($MgSO_4$), filtered, and concentrated. The residue was then purified by flash chromatography (15% EtOAc/Hexane) to yield the desired product.

$^1$H NMR (400 MHz, $CDCl_3$) δ 8.15 (dd, 1H, J=2.30, 6.48 Hz), 8.09 (d, 1H, J=2.30 Hz), 7.85 (d, 1H, J=6.46 Hz), 3.98 (s, 3H).

Step 2: 6-Cyano-biphenyl-3-carboxylic acid methyl ester

4-Cyano-3-(trifluoromethanesulfonyloxy)-benzoic acid methyl ester from step 1 (2.5 g, 8.1 mmol) and phenylboronic acid (2 g, 16.2 mmol) were dissolved in DMF (33 ml) and treated with $Et_3N$ (3.1 ml, 17.8 mmol). Argon was bubbled into the solution for 20 min. and then a catalytic amount of $PdCl_2(PPh_3)_2$ (285 mg, 0.405 mmol) was added. The reaction mixture was warmed to 90° C. and stirred for 3 hours under argon atmosphere. The reaction was quenched with satd. $NaHCO_3$ (20 mL) and extracted with EtOAc (2×20 mL). The organic layer was dried ($MgSO_4$), filtered, and concentrated. The residue was purified by flash chromatography (10% EtOAc/Hexane) to yield the desired product. FAB MS: 238 m/z ($M^+$+H)

Step 3: 5-Hydroxymethyl-biphenyl-2-carbonitrile

6-Cyano-biphenyl-3-carboxylic acid methyl ester from step 2 (1.4 g, 5.9 mmol) was dissolved in THF (24 ml).

LiBH$_4$ in THF (2M, 5.9 ml, 11.8 mmol) was added. The reaction mixture was heated to 70° C. for 3 hours. The reaction mixture was quenched carefully with 3N HCl and then extracted with EtOAc (3×20 mL). The organic layers were combined, washed with brine, dried (MgSO$_4$), filtered and concentrated to yield the desired product. FAB MS: 210 m/z (M$^+$+H)

Step 4: 5-Bromomethyl-biphenyl-2-carbonitrile

5-Hydroxymethyl-biphenyl-2-carbonitrile from step 3 (1.3 g, 6.2 mmol) was dissolved in THF (31 ml) and treated with Ph$_3$P (2.4 g, 9.3 mmol) followed by CBr$_4$ (3 g, 9.3 mmol). The reaction was mixture stirred at room temp. for 16 hours. The solvent was removed in vacuo and the residue was purified by flash chromatography (10% EtOAc/Hexane) to yield the desired product. FAB MS: 273 m/z (M$^+$+H)

Step 5: 5-[5-(5-Chloro-2-oxo-2H-[1,2']bipyridinyl-5'-ylmethyl)-imidazol-1-ylmethyl]-biphenyl-2-carbonitrile 5-Bromomethyl-biphenyl-2-carbonitrile from step 4 (51 mg, 0.19 mmol) and 5-chloro-5'-(1-trityl-1H-imidazol-4-ylmethyl)-[1,2']bipyridinyl-2-one from Example 23, Step 5 (100 mg, 0.19 mmol) were dissolved in CH$_3$CN (950 µl) and heated to 60° C. for 14 hours. The solvent was removed in vacuo and th ressidue dissolved in MeOH (950 µl). The reaction mixture was heated to 60° C. for 4 hours. Solvent was removed in vacuo and the residue was purified by flash chromatography [15% MeOH(5% NH$_4$OH)/CH$_2$Cl$_2$] to yield the final product.

$^1$H NMR (400 MHz, CDCl$_3$) δ 8.24 (s, 1H), 7.95 (s, 1H), 7.91 (d, 1H, J=5.63 Hz), 7.70 (d, 1H, J=4.3 Hz), 7.62 (s, 1H), 7.55–7.42 (m, 6H), 7.34 (dd, 1H, J=6.54, 2.20 Hz), 7.07 (s, 1H), 6.98–7.01 (m, 2H), 6.62 (d, 1H, J=9.71 Hz), 5.05 (s, 2H), 3.82 (s, 2H).

Analysis calculated for (C$_{28}$H$_{20}$N$_5$OCl.2.4 HCl.0.4 CH$_3$CN); C,59.44; H. 4.09; N,13.00; Found: C,59.37; H,4.33; N,12.97; FAB MS: 478 m/z (M$^+$+H)

Example 47

4-[5-(5-Chloro-2-oxo-2H-[1,2']bipyridinyl-5'-ylmethyl)-imidazol-1-ylmethyl]-phthalonitrile Step 1: 3,4-Dicyano-benzoic acid methyl ester 4-Cyano-3-(trifluoromethanesulfonyloxy)-benzoic acid methyl ester (from L-819,063 step 1, 4.92 g, 16 mmol) was dissolved in DMF (22.9 ml) and treated with Zn(CN)$_2$ (1.3 g, 11.2 mmol). The reaction mixture was degassed by bubbling in argon for 1 hr. Pd(PPh$_3$)$_4$ (924 mg, 0.8 mmol) was then added and the reaction was heated to 100° C. for 15 hours. The reaction mixture was poured into water (20 mL) and extracted with EtOAc (2×20 mL). The organic layer was washed with water (2×10 mL), 5% HCl (1×10 mL), brine (1×10 mL), dried (MgSO$_4$), filtered and concentrated. The residue was purified by flash chromatography (100% CH$_2$Cl$_2$) to yield the desired compound. FAB MS: 187 m/z (M$^+$+H)

Step 2: 4-Hydroxymethyl-phthalonitrile 3,4-Dicyano-benzoic acid methyl ester from step 1 (2.4 g, 12.9 mmol) was dissolved in THF (65 ml). LiBH$_4$ in THF (2M, 12.9 ml, 25.8 mmol) was added. The reaction mixture was heated to 70° C. for 3 hours. The reaction was quenched carefully with 3N HCl and then extracted with EtOAc (3×20 mL). The organic layers were combined, washed with brine, dried (MgSO$_4$), filtered and concentrated to yield the desired product. FAB MS: 159 m/z (M$^+$+H)

Step 3: 4-Bromomethyl-phthalonitrile

4-Hydroxymethyl-phthalonitrile from step 2 (1.3 g, 8.2 mmol) was dissolved in THF (41 ml) and treated with Ph$_3$P (3.2 g, 12.3 mmol) followed by CBr$_4$ (4 g, 12.3 mmol). The reaction mixture was stirred at room temp. for 21 hours. The solvent was removed in vacuo and the residue purified by flash chromatography (15% EtOAc/Hexane) to yield the desired product. FAB MS: 222 m/z (M$^+$+H)

Step 4: 4-[5-(5-Chloro-2-oxo-2H-[1,2']bipyridinyl-5'-ylmethyl)-imidazol-1-ylmethyl]-phthalonitrile 4-Bromomethyl-phthalonitrile from step 3 (50 mg, 0.28 mmol) and 5-chloro-5'-(1-trityl-1H-imidazol-4-ylmethyl)-[1,2']bipyridinyl-2-one from Example 23, Step 5 (150 mg, 0.28 mmol) were dissolved in CH$_3$CN (1.4 ml) and heated to 60° C. for 16 hours. The solvent was removed in vacuo and redissolved in MeOH (1.4 ml). The reaction mixture was heated to 60° C. for several hours. Solvent was removed in vacuo and the resulting residue was purified by flash chromatography [4% MeOH(5% NH$_4$OH)/CH$_2$Cl$_2$] to yield the final product.

$^1$H NMR (400 MHz, CDCl$_3$) δ 8.20 (d, 1H, J=2.20 Hz), 7.96 (d, 1H, J=3.93 Hz), 7.89 (d, 1H, J=8.24 Hz), 7.75 (d, 1H, J=7.80 Hz), 7.60 (s, 1H), 7.54–7.51 (m, 2H), 7.36 (d, 1H, J=2.93 Hz), 7.16 (d, 1H, J=8.97 Hz), 7.06 (s, 1H), 6.61 (d, 1H, J=8.89 Hz), 5.10 (s, 2H), 3.84 (s, 2H). Analysis calculated for (C$_{23}$H$_{15}$N$_6$OCl.2.5 MeOH.2.5 CH$_2$Cl$_2$); C,46.75; H,4.20; N,11.68; Found: C,46.67; H,4.59; N, 11.64; FAB MS: 427 m/z (M$^+$+H)

Example 48

5-[5-(5-Chloro-2-oxo-2H-[1,2']bipyridinyl-5'-ylmethyl)-imidazol-1-ylmethyl]-pyridine-2-carbonitrile Step 1: 3-(tert-Butyl-dimethyl-silanyloxymethyl)-pyridin-1-ol 3-Pyridylcarbinol n-oxide (from Aldrich, 3 g, 24 mmol) was dissolved in CH$_2$Cl$_2$ (120 ml) and treated with tert-butyldimethyl-silylchloride (4 g, 28.8 mmol). Et$_3$N (6.7 ml, 48 mmol) was added and the reaction mixture stirred at room temp. for 18 hours. Saturated NaHCO$_3$ (50 mL) was added and the layers were separated. The organic layer was extracted with brine (1×50 mL), dried(MgSO$_4$), filtered, and concentrated to yield the desired product.

$^1$H NMR (400 MHz, CDCl$_3$) δ 8.22 (s, 1H), 8.10 (d, 1H, J=3.76 Hz), 7.28–7.15 (m, 2H), 4.68 (s, 2H), 0.90 (s, 9H), 0.11 (s, 6H).

Step 2: 3-(tert-Butyl-dimethyl-silanyloxymethyl)-pyridine-2-carbonitrile and 5-(tert-Butyl-dimethyl-silanyloxymethyl)-pyridine-2-carbonitrile 3-(tert-Butyl-dimethyl-silanyloxymethyl)-pyridin-1-ol from step 1 (2.4 g, 9.9 mmol) was dissolved in CH$_2$Cl$_2$ (100 mL) and treated with trimethylsilylcyanide (1.3 ml, 9.9 mmol). The reaction mixture was stirred for 5 min. at room temperature. The mixture was then treated with dimethylcarbamyl chloride (910 µl, 9.9 mmol) and stirred at room temperature for 15 hours. HPLC analysis showed that the reaction had not gone to completion. More trimethylsilylcyanide (264 µl, 1.98 mmol) and dimethylcarbamyl chloride (910 µl, 9.9 mmol) were added and the reaction mixture was heated to 75° C. for 3.5 hrs. The reaction was cooled to room temperature and saturated NaHCO$_3$ (50 mL) was added. The mixture was separated and the water layer was extracted with CH$_2$Cl$_2$ (2×40 mL). The combined organic layers were dried (MgSO$_4$), filtered, and concentrated. The residue was purified by flash chromatography [2% MeOH(5% NH$_4$OH)/CH$_2$Cl$_2$] to yield a mixture of of 3-(tert-Butyl-dimethyl-silanyloxymethyl)-pyridine-2-carbonitrile and 5-(tert-Butyl-dimethyl-silanyloxymethyl)-pyridine-2-carbonitrile (10:1).

3-(tert-Butyl-dimethyl-silanyloxymethyl)-pyridine-2-carbonitrile:

$^1$H NMR (400 MHz, CDCl$_3$) δ 8.58 (d, 1H, J=5.45 Hz), 8.00 (d, 1H, J=7.85 Hz), 7.54 (dd, 1H, J=5.40, 7.65 Hz), 4.92 (s, 2H), 0.95 (s, 9H), 0.15 (s, 6H).

5-(tert-Butyl-dimethyl-silanyloxymethyl)-pyridine-2-carbonitrile:

$^1$H NMR (400 MHz, CDCl$_3$) δ 8.65 (bs, 1H), 7.80 (dd, 1H, J=1.85, 5.30 Hz), 7.67 (d, 1H, J=5.30 Hz), 4.82 (s, 2H), 0.95 (s, 9H), 0.15 (s, 6H).

Step 3: 3-hydroxymethyl-pyridine-2-carbonitrile and 5-hydroxymethyl-pyridine-2-carbonitrile A mixture of of 3-(tert-Butyl-dimethyl-silanyloxymethyl)-pyridine-2-carbonitrile and 5-(tert-Butyl-dimethyl-silanyloxymethyl)-pyridine-2-carbonitrile from step 2 (1.58 g, 5.94 mmol) were dissolved in THF (30 ml) and treated with tetrabutylammoniumflouride (1M, 1.2 ml, 1.2 mmol). The reaction mixture was stirred at room temperature for 12 hours. The solvent was removed in vacuo and the residue was purified by flash chromatography (25% EtOAc/Hexane) to yield pure samples of the two regioisomers: 3-hydroxymethyl-pyridine-2-carbonitrile and 5-hydroxymethyl-pyridine-2-carbonitrile (10:1 ratio by weight).

3-hydroxymethyl-pyridine-2-carbonitrile:

$^1$H NMR (400 MHz, CDCl$_3$) δ 8.91 (d, 1H, J=5.80 Hz), 7.92 (d, 1H, J=7.30 Hz), 7.58 (dd, 1H, J=5.80, 7.30 Hz), 5.39 (s, 2H).

5-hydroxymethyl-pyridine-2-carbonitrile:

$^1$H NMR (400 MHz, CDCl$_3$) δ 8.70 (s, 1H), 7.87 (dd, 1H, J=2.0, 5.60 Hz), 7.70 (d, 1H, J=5.56 Hz), 4.84 (d, 2H, J=6.56 Hz).

Step 4: 5-[5-(5-Chloro-2-oxo-2H-[1,2']bipyridinyl-5'-ylmethyl)-imidazol-1-ylmethyl]-pyridine-2-carbonitrile To a cooled solution (−78° C.) of 5-hydroxymethyl-pyridine-2-carbonitrile from step 3 (37 mg, 0.28 mmol) and 5-chloro-5'-(1-trityl-1H-imidazol-4-ylmethyl)-[1,2'] bipyridinyl-2-one from Example 23, Step 5 (150 mg, 0.28 mmol) in CH$_2$Cl$_2$ (1.38 ml) was added DIEA (106 μl, 0.61 mmol) followed immediately by the addition of Tf$_2$O (70 μl, 0.41 mmol). The reaction mixture was stirred at −78° C. for 1 hour and was then transferred to an ice bath and stirred at 0° C. for another hour. The solvent was removed in vacuo. The residue was then dissolved in MeOH (1.38 ml) and heated to 60° C. for several hours. The MeOH was removed in vacuo and the residue treated with saturated NaHCO$_3$ (2 mL) and extracted with CH$_2$Cl$_2$ (2×10 mL). The organic layer was washed with brine (1×10 mL), dried (MgSO$_4$), filtered and concentrated. Residue was purified by flash chromatography [4% MeOH(5% NH$_4$OH)/CH$_2$Cl$_2$] to yield the final product.

$^1$H NMR (400 MHz, CDCl$_3$) δ 8.41 (d, 1H, J=1.02 Hz), 8.20 (d, 1H, J=1.4 Hz), 7.96 (d, 1H, J=2.15 Hz), 7.89 (d, 1H, J=8.24 Hz), 7.65–7.60 (m, 2H), 7.54 (dd, 1H, J=2.20, 6.60 Hz), 7.38 (dd, 1H, J=2.93, 7.70 Hz), 7.16 (d, 1H, J=8.97 Hz), 7.06 (s, 1H), 6.61 (d, 1H, J=7.89 Hz), 5.10 (s, 2H), 3.84 (s, 2H). Analysis calculated for (C$_{21}$H$_{17}$N$_6$OCl.0.85 HCl.1.15 CH$_2$Cl$_2$); C,49.86; H,3.81; N,15.75; Found: C,49.83; H,4.18; N,15.71; FAB MS: m/z 403 (M$^+$+H)

Example 49

4-[3-(5-chloro-2-oxo-2H-[1,2']bipyridinyl-5'-ylmethyl)-3H-imidazol-4-ylmethyl]-2-methoxy-benzonitrile Step 1: 4-bromomethyl-2-methoxy-benzonitrile 4-hydroxymethyl-2-methoxy-benzonitrile (from L-819, 538, step 2, 2.0 g, 12.3 mmol) was dissolved in THF (61.5 ml) and treated with Ph$_3$P (4.82 g, 18.4 mmol) followed by CBr$_4$(6.1 g, 18.4 mmol). The reaction was mixture stirred at room temp. for 17 hours. The solvent was removed in vacuo and the residue was purified by flash chromatography (10% EtOAc/Hexane) to yield the desired product. FAB MS: 226w m/z (M$^+$+H)

Step 2: 2-methoxy-4-(1-trityl-1H-imidazol-4-ylmethyl)-benzonitrile

To a suspension of activated zinc dust (150 mg, 2.29 mmol) in THF (0.75 mL) was added dibromoethane (0.02 mL, 0.23 mmol) and the reaction stirred under argon for 45 minutes, at 20° C. The suspension was cooled to 0° C. and 4-bromomethyl-2-methoxy-benzonitrile from step 1 above, (345.9 mg, 1.53 mmol) in THF (3 mL) was added dropwise over a period of 10 minutes. The reaction was then allowed to stir at 20° C. for 6 hours and bis(triphenylphosphine) Nickel II chloride (90.3 mg, 0.14 mmol) and 5-iodotrityl imidazole (601 mg, 1.38 mmol) were added in one portion. The resulting mixture was stirred 16 hours at 20° C. and then quenched by addition of saturated NH$_4$Cl solution (10 mL) and the mixture stirred for 2 hours. Saturated aq. NaHCO$_3$ solution was added to give a pH of 8 and the solution was extracted with EtOAc (2×25 mL), dried (MgSO$_4$) and the solvent evaporated in vacuo. The residue was chromatographed (silica gel, [0–5% MeOH (5% NH$_4$OH) in CH$_2$Cl$_2$]) to afford the title compound as a white solid.

$^1$H NMR (CDCl$_3$, 400 Mz) δ 7.43 (d, 1H, J=8.24 Hz), 7.40 (d, 1H, J=0.92 Hz), 6.86 (d, 1H, J=5.31 Hz), 6.61 (s, 1H), 3.92 (s, 2H), 3.85 (s, 3H).

Step 3: 4-[3-(5-chloro-2-oxo-2H-[1,2']bipyridinyl-5'-ylmethyl)-3H-imidazol-4-ylmethyl]-2-methoxy-benzonitrile 4-(-2-Oxo-2-H-pyridin-1-yl)benzyl bromide from Example 10, step 2 (108.4 mg, 0.63 mmol) and 2-methoxy-4-(1-trityl-1H-imidazol-4-ylmethyl)-benzonitrile from step 2 above (287 mg, 0.63 mmol) were suspended in CH$_3$CN and heated to reflux for 3 hours. The reaction mixture was concentrated and the residue taken up in MeOH and refluxed for 2 hours. The MeOH was removed in-vacuo. The resulting oil was partitioned between EtOAc and saturated NaHCO$_3$. The aqueous layer was extracted twice with EtOAc. The organic layers were combined, washed with brine, dried (MgSO$_4$), filtered and concentrated to yield an oil which was purified by flash chromatography using 0–20% MeOH (5% NH$_4$OH) in CH$_2$Cl$_2$ as an eluent. Pure fractions were collected and concentrated to give a white solid. The white solid was collected and dried under high for 12 hours to give the final product.

$^1$H NMR (400 MHz, CDCl$_3$) δ 8.10 (d, 1H, J=2.38 Hz), 8.00 (d, 1H, J=2.75 Hz), 7.98 (d, 1H, J=8.45 Hz), 7.61 (s, 1H), 7.45 (d, 1H, J=7.87 Hz), 7.39 (d, 1H, J=2.38 Hz), 7.37 (d, 1H, J=2.66 Hz), 7.34 (d, 1H, J=7.93 Hz), 6.99 (s, 1H), 6.73 (d, 1H, J=7.88 Hz), 6.63–6.60 (m, 2H), 4.99 (s, 2H), 3.87 (s, 2H), 3.85 (s, 3H). Analysis calculated for (C$_{23}$H$_{18}$N$_5$O$_2$Cl, 1.50 HC$_{1, 0.60}$ MeOH); C, 56.04; H, 4.36; N, 13.85; Found C, 56.05; H, 4.30; N, 13.69; FAB MS: m/z 432 (M$^+$+H)

Example 50

4-[3-(5-chloro-2-oxo-2H-[1,2']bipyridinyl-5'-ylmethyl)-3H-imidazol-4-ylmethyl]2-phthalonitrile Step 1: 4-(1-trityl-1H-imidazol-4-ylmethyl)-phthalonitrile To a suspension of activated zinc dust (194 mg, 2.97 mmol) in THF (1 mL) was added dibromoethane (0.026 mL, 0.03 mmol) and the reaction stirred under argon for 45 minutes, at 20° C. The suspension was cooled to 0° C. 4-bromomethyl-phthalonitrile from L-819,615, step 3 (430 mg, 1.53 mmol) in THF (4 mL) was added dropwise over a period of 10 minutes. The reaction was then allowed to stir at 20° C. for 6 hours and bis(triphenylphosphine)Nickel II chloride (116 mg, 0.18 mmol) and 5-iodotrityl imidazole (778 mg, 1.78 mmol) were added in one portion. The resulting mixture was stirred 16 hours at 20° C. and then quenched by addition of saturated NH₄Cl solution (10 mL) and the mixture stirred for 2 hours. Saturated aq. NaHCO₃ solution was added to give a pH of 8 and the solution was extracted with EtOAc (2×25 mL), dried (MgSO₄) and the solvent evaporated in vacuo. The residue was chromatographed (silica gel, using 0–5% MeOH (5% NH₄OH) in CH₂Cl₂) to afford the title compound as a white solid.

¹H NMR (CDCl₃, 400Mz) δ 7.70–7.60 (m, 3H), 7.42 (s, 1H), 6.66 (s, 1H), 3.98 (s, 2H).

Step 2: 4-[3-(5-chloro-2-oxo-2H-[1,2']bipyridinyl-5'-ylmethyl)-3H-imidazol-4-ylmethyl]-phthalonitrile 4-(-2-Oxo-2-H-pyridin-1-yl)benzyl bromide from Example 10, step 2 (107 mg, 0.38 mmol) and 4-(1-trityl-1H-imidazol-4-ylmethyl)-phthalonitrile from step 1 above (188 mg, 0.42 mmol) were suspended in CH₃CN and heated to reflux for 3 hours. The reaction mixture was concentrated and the residue taken up in MeOH and refluxed for 2 hours. The MeOH was removed in-vacuo. The resulting oil was partitioned between EtOAc and saturated NaHCO₃. The aqueous layer was extracted twice with EtOAc. The organic layers were combined, washed with brine, dried (MgSO₄), filtered and concentrated to yield an oil which was purified by flash chromatography using 5% MeOH (5% NH₄OH)/CH₂Cl₂ as an eluent. Pure fractions were collected and concentrated to give a white solid as the final product.

¹H NMR (400 MHz, CDCl₃) δ 8.28 (bs, 1H), 7.62 (s, 1H), 7.20 (d, 1H, J=1.90 Hz), 6.90–7.03 (m, 4H), 6.83 (dd, 1H, J=2.23, 5.20 Hz), 6.65–6.72 (m, 2H), 5.80 (d, 1H, J=5.2 Hz), 4.75 (s, 2H), 3.48 (s, 2H). Analysis calculated for (C₂₃H₁₅N₆OCl), 2.0 HCl, 2.20 MeOH, 1.45; CH₂Cl₂; C, 46.16; H, 4.17; N, 12.12; Found: C, 45.85; H, 4.63; N, 12.61; FAB MS: m/z 427 (M⁺+H)

Example 51

5-[5-(5-chloro-2-oxo-2H-[1,2']bipyridinyl-5'-ylmethyl)-imidazol-1-ylmethyl]-2-methoxy-benzonitrile Step 1: 3-cyano-4-hydroxybenzoic acid methyl ester The 3-cyano-4-hydroxybenzoic acid methyl ester was prepared in a manner similar to that described for 4-cyano-3-hydroxy-benzoic acid methyl ester (Example 34, steps 1–3).

¹H NMR (400 MHz, CDCl₃) δ 8.10 (s, 1H), 7.95 (d, 1H, J=6.54 Hz), 6.86 (d, 1H, J=6.95 Hz), 3.80 (s, 3H). FAB MS: m/z 178 (M⁺+H)

Step 2: 3-Cyano-4-methoxy-benzoic acid methyl ester 3-cyano-4-hydroxybenzoic acid methyl ester from step 1 (1 g, 3.6 mmol) was dissolved in DMF (18 ml) and treated with NaH (290 g, 7.2 mmol) and CH₃I (450 μl, 7.2 mmol). The reaction mixture was stirred at room temperature for 24 hours. EtOAc was added to the mixture and extracted with 5% citric acid (2×10 mL), saturated NaHCO₃ (2×10 mL) and brine (1×10 mL). The organic layer was dried (MgSO₄), filtered, and concentrated to yield the desired product.

Step 3: 2-Hydroxymethyl-5-methoxy-benzonitrile

3-Cyano-4-methoxy-benzoic acid methyl ester from step 2 (1.14 g, 6 mmol) was dissolved in THF (30 ml). LiBH₄ in THF (2M, 6 ml, 12 mmol) was added. The reaction mixture was heated at 70° C. for 3 hours. The reaction mixture was quenched carefully with 3N HCl and then extracted with EtOAc (3×10 mL). The organic layers were combined, washed with brine, dried (MgSO₄), filtered and concentrated to yield the desired product.

Step 4: 2-Bromomethyl-5-methoxy-benzonitrile

2-Hydroxymethyl-5-methoxy-benzonitrile from step 3 (1.12 g, 7.62 mmol) was dissolved in THF (38 ml) and treated with Ph₃P (3 g, 11.4 mmol) followed by CBr₄ (3.8 g, 11.4 mmol). The reaction mixture was stirred at room temp. for 21 hours. The solvent was removed in vacuo and the residue purified by flash chromatography (15% EtOAc/Hexane) to yield the desired product.

¹H NMR (400 MHz, CDCl₃) δ 7.62–7.55 (m, 2H), 6.95 (d, 1H, J=6.97 Hz), 4.43 (s, 2H), 3.93 (s, 3H).

Step 5: 5-[5-(5-chloro-2-oxo-2H-[1,2']bipyridinyl-5'-ylmethyl)-imidazol-1-ylmethyl]-2-methoxy-benzonitrile 2-Bromomethyl-5-methoxy-benzonitrile from step 4 (70 mg, 0.30 mmol) and 5-chloro-5'-(1-trityl-1H-imidazol-4-ylmethyl)-[1,2']bipyridinyl-2-one from Example 23, Step 5 (200 mg, 0.378 mmol) were dissolved in CH₃CN (2 ml) and heated to 60° C. for 16 hours. The solvent was removed in vacuo and redissolved in MeOH (2 ml). The reaction mixture was heated to 60° C. for several hours. Solvent was removed in vacuo and the resulting residue was purified by flash chromatography [4% MeOH(5% NH₄OH)/CH₂Cl₂] to yield the final product.

¹H NMR (400 MHz, CDCl₃) δ 9.58 (s, 1H), 8.27 (s, 1H), 7.98 (d, 1H, J=2.74 Hz), 7.94 (d, 1H, J=8.42 Hz), 7.64 (d, 1H, J=2.20 Hz), 7.62 (d, 1H, J=2.20 Hz), 7.47–7.45 (m, 2H), 7.34 (dd, 1H, J=3.93, 6.96 Hz), 7.14 (s, 1H), 6.98 (d, 1H, J=9.52 Hz), 6.58 (d, 1H, J=9.70 Hz), 5.47 (s, 2H), 4.02 (s, 2H), 3.93 (s, 3H). Analysis calculated for (C₂₃H₁₈N₅O₂Cl.0.89 HCl.1.55H₂O); C,56.07; H,4.50; N,14.22; Found C,56.06; H,4.50; N,13.86; FAB MS: m/z 432 (M⁺+H)

Example 52

4-[3-(5-chloro-2-oxo-2H-[1,2']bipyridinyl-5'-ylmethyl)-3H-imidazol-4-ylmethyl]-biphenyl-2-carbonitrile Step 1: 3-cyano-4-(trifluoromethanesulfonyloxy)benzoic acid methyl ester 3-cyano-4-hydroxybenzoic acid methyl ester from example 51, step 1 (2 g, 11.3 mmol) was dissolved in CH₂Cl₂ (57 ml) and cooled to 0° C. in an ice bath. The mixture was treated with Et₃N (3 ml, 22.6 mol) followed by the addition of Tf₂O (1.9 ml, 11.3 mmol). The reaction mixture was warmed to room temp. and stirred for 4 hours. Saturated NaHCO₃ (10 mL) was added and the mixture was extracted with EtOAc (2×10 mL). The organic layers were combined and dried (MgSO₄), filtered, and concentrated. The residue was then purified by flash chromatography (15% EtOAc/Hexane) to yield the desired product.

¹H NMR (400 MHz, CDCl₃) δ 8.45 (d, 1H, J=2.2 Hz), 8.38 (dd, J=2.2, 8.54 Hz), 7.59 (d, 1H, J=8.54 Hz), 3.99 (s, 3H).

Step 2: 6-Cyano-biphenyl-4-carboxylic acid methyl ester

3-Cyano-4-(trifluoromethanesulfonyloxy)-benzoic acid methyl ester from step 1 (2.5 g, 8.1 mmol) and phenylboronic acid (2 g, 16.2 mmol) were dissolved in DMF (33 ml) and treated with Et₃N (3.1 ml, 17.8 mmol). Argon was bubbled into the solution for 20 min. and then a catalytic amount of PdCl₂(PPh₃)₂ (285 mg, 0.405 mmol) was added. The reaction mixture was warmed to 90° C. and stirred for 3 hours under argon atmosphere. The reaction was quenched with satd. NaHCO₃ (20 mL) and extracted with EtOAc (2×20 mL). The organic layer was dried (MgSO₄), filtered, and concentrated. The residue was purified by flash chromatography (10% EtOAc/Hexane) to yield the desired product.

¹H NMR (400 MHz, CDCl₃) δ 8.43 (d, 1H, J=1.83 Hz), 8.28 (dd, 1H, J=1.28, 8.32 Hz), 7.62–7.50 (m, 6H), 3.98 (s, 3H). FAB MS: 238 m/z (M⁺+H)

Step 3: 4-Hydroxymethyl-biphenyl-2-carbonitrile

6-Cyano-biphenyl-4-carboxylic acid methyl ester from step 2 (1.4 g, 5.9 mmol) was dissolved in THF (24 ml).

LiBH$_4$ in THF (2M, 5.9 ml, 11.8 mmol) was added. The reaction mixture was heated to 70° C. for 3 hours. The reaction mixture was quenched carefully with 3N HCl and then extracted with EtOAc (3×20 mL). The organic layers were combined, washed with brine, dried (MgSO$_4$), filtered and concentrated to yield the desired product. FAB MS: 210 m/z (M$^+$+H)

Step 4: 4-Bromomethyl-biphenyl-2-carbonitrile

5-Hydroxymethyl-biphenyl-2-carbonitrile from step 3 (1.3 g, 6.2 mmol) was dissolved in THF (31 ml) and treated with Ph$_3$P (2.4 g, 9.3 mmol) followed by CBr$_4$ (3 g, 9.3 mmol). The reaction was mixture stirred at room temp. for 16 hours. The solvent was removed in vacuo and the residue was purified by flash chromatography (10% EtOAc/Hexane) to yield the desired product. FAB MS: m/z 272 (M$^+$+H)

Step 5: 4-(1-trityl-1H-imidazol-4-ylmethyl)-biphenyl-2-carbonitrile

To a suspension of activated zinc dust (107 mg, 1.63 mmol) in THF (0.55 mL) was added dibromoethane (0.014 mL, 0.16 mmol) and the reaction stirred under argon for 45 minutes, at 20° C. The suspension was cooled to 0° and 4-bromomethyl-biphenyl-2-carbonitrile from step 4 above (296.2 mg, 1.09 mmol) in THF (2.2 mL) was added dropwise over a period of 10 minutes. The reaction was then allowed to stir at 20° C. for 6 hours and bis (triphenylphosphine) Nickel II chloride (64.2 mg, 0.10 mmol) and 5-iodotrityl imidazole (428 mg, 0.98 mmol) were added in one portion. The resulting mixture was stirred 16 hours at 20° C. and then quenched by addition of saturated NH$_4$Cl solution (10 mL) and the mixture stirred for 2 hours. Saturated aq. NaHCO$_3$ solution was added to give a pH of 8 and the solution was extracted with EtOAc (2×25 mL), dried (MgSO$_4$) and the solvent evaporated in vacuo. The residue was chromatographed (silica gel, [0–5% MeOH (5% NH$_4$OH) in CH$_2$Cl$_2$]) to afford the title compound as a white solid.

$^1$H NMR (CDCl$_3$, 400 Mz) δ 7.57–7.42 (m, 9H), 6.66 (s, 1H), 3.95 (s, 2H).

Step 6: 4-[3-(5-chloro-2-oxo-2H-[1,2']bipyridinyl-5'-ylmethyl)-3H-imidazol-4-ylmethyl]-biphenyl-2-carbonitrile 4-(-2-Oxo-2-H-pyridin-1-yl)benzyl bromide from Example 10 step 2 (173 mg, 0.60 mmol) and 4-(1-trityl-1H-imidazol-4-ylmethyl)-biphenyl-2-carbonitrile from step 1 above (337 mg, 0.68 mmol) were suspended in CH$_3$CN and heated to reflux for 3 hours. The reaction mixture was concentrated and the residue taken up in MeOH and refluxed for 2 hours. The MeOH was removed in-vacuo. The resulting oil was partitioned between EtOAc and saturated NaHCO$_3$. The aqueous layer was extracted twice with EtOAc. The organic layers were combined, washed with brine, dried (MgSO$_4$), filtered and concentrated to yield an oil which was purified by flash chromatography using [5% MeOH (5% NH$_4$OH)/CH$_2$Cl$_2$] as an eluent. Pure fractions were collected and concentrated to give a white solid as the final product.

$^1$H NMR (400 MHz, CD$_3$OD) δ 9.17 (s, 1H), 8.24 (s, 1H), 7.79 (s, 1H), 7.77 (d, 1H, J=6.32 Hz), 7.26–7.49 (m, 11H), 6.48 (d, 1H, J=5.25 Hz), 5.56 (s, 2H), 4.25 (s, 2H). Analysis calculated for (C$_{28}$H$_{20}$N$_5$OCl), 1.45 HCl, 0.05H$_2$O ; C, 63.24; H, 4.09; N, 13.17; Found: C, 63.21; H, 4.08; N, 13.38; FAB MS: m/z 478 (M$^+$+H)

Example 53

5-[3-(5-chloro-2-oxo-2H-[1,2']bipyridinyl-5'-ylmethyl)-3H-imidazol-4-ylmethyl]-biphenyl-2-carbonitrile Step 1: 5-(1-trityl-1H-imidazol-4-ylmethyl)-biphenyl-2-carbonitrile To a suspension of activated zinc dust (125 mg, 1.92 mmol) in THF (0.6 mL) was added dibromoethane (0.016 mL, 0.19 mmol) and the reaction stirred under argon for 45 minutes, at 20° C. The suspension was cooled to 0° and 5-bromomethyl-biphenyl-2-carbonitrile from L-819,063, step 4 (347.5 mg, 1.28 mmol) in THF (2.4 mL) was added dropwise over a period of 10 minutes. The reaction was then allowed to stir at 20° C. for 6 hours and bis(triphenylphosphine) Nickel II chloride (75 mg, 0.115 mmol) and 5-iodotrityl imidazole (501 mg, 1.15 mmol) were added in one portion. The resulting mixture was stirred 16 hours at 20° C. and then quenched by addition of saturated NH$_4$C$_1$ solution (10 mL) and the mixture stirred for 2 hours. Saturated aq. NaHCO$_3$ solution was added to give a pH of 8 and the solution was extracted with EtOAc (2×25 mL), dried (MgSO$_4$) and the solvent evaporated in vacuo. The residue was chromatographed (silica gel, [0–5% MeOH (5% NH$_4$OH) in CH$_2$Cl$_2$]) to afford the title compound as a white solid.

$^1$H NMR (CDCl$_3$, 400 Mz) δ 7.65 (d, 1H, J=8.06 Hz), 7.49–39 (m, 8H), 6.61 (s,1H), 3.98 (s, 2H).

Step 2: 5-[3-(5-chloro-2-oxo-2H-[1,2']bipyridinyl-5'-ylmethyl)-3H-imidazol-4-ylmethyl]-biphenyl-2-carbonitrile 4-(-2-Oxo-2-H-pyridin-1-yl)benzyl bromide from Example 10 step 2 (173 mg, 0.60 mmol) and 5-(1-trityl-1H-imidazol-4-ylmethyl)-biphenyl-2-carbonitrile from step 1 above (337 mg, 0.68 mmol) were suspended in CH$_3$CN and heated to reflux for 3 hours. The reaction mixture was concentrated and the residue taken up in MeOH and refluxed for 2 hours. The MeOH was removed in-vacuo. The resulting oil was partitioned between EtOAc and saturated NaHCO$_3$. The aqueous layer was extracted twice with EtOAc. The organic layers were combined, washed with brine, dried (MgSO$_4$), filtered and concentrated to yield an oil which was purified by flash chromatography using [5% MeOH (5% NH$_4$OH)/CH$_2$Cl$_2$] as an eluent. Pure fractions were collected and concentrated to give a white solid as the final product.

$^1$H NMR (400 MHz, CDCl$_3$) δ 8.40 (s, 1H), 8.04 (d, 1H, J=3.50 Hz), 7.98 (d, 1H, J=2.75 Hz), 7.82 (m, 1H), 7.73 (d, 1H, J=8.06 Hz), 7.52–7.14 (m, 10H), 6.59 (d, 1H, J=9.71 Hz), 5.57 (s, 2H), 4.04 (s, 2H). Analysis calculated for (C$_{28}$H$_{20}$N$_5$OCl), 1.95 HCl, 0.50 MeOH; C, 60.57; H, 4.27; N, 12.39; Found: C, 60.59; H, 4.25; N, 12.17; FAB MS: m/z 478 (M$^+$+H)

Example 54

5-chloro-5'-[5-(4-[1,2,3]thiadiazol-4-yl-benzyl)-imidazol-1-ylmethyl]-[1,2']bipyridinyl-2-one 4-(4-bromomethyl-phenyl)-[1,2,3]thiadiazole (from Maybridge, 96.5 mg, 0.38 mmol) and 5-chloro-5'-(1-trityl-1H-imidazol-4-ylmethyl)-[1,2']bipyridinyl-2-one from example 10 step 2 (200 mg, 0.38 mmol) were dissolved in CH$_3$CN (2 ml) and heated to 60° C. for 16 hours. The solvent was removed in vacuo and redissolved in MeOH (2 ml). The reaction mixture was heated to 60° C. for several hours. Solvent was removed in vacuo and the resulting residue was purified by flash chromatography [0–5% MeOH(5% NH$_4$OH )/CH$_2$Cl$_2$] to yield the final product.

$^1$H NMR (400 MHz, CDCl$_3$) δ 9.52 (bs, 1H), 8.75 (s, 1H), 8.27 (s, 1H), 8.06 (d, 1H, J=7.87 Hz), 7.96 (m, 1H), 7.57 (d, 1H, J=6.78 Hz), 7.35–7.21 (m, 6H), 6.59 (d, 1H, J=9.71 Hz), 5.51 (s, 2H), 4.01 (s, 2H). Analysis calculated for (C$_{23}$H$_{17}$N$_6$OSCl.2.35 HCl); C, 50.53; H, 3.57; N 15.38; Found: C, 50.56; H, 3.92; N 15.71, FAB MS: m/z 461 (M$^+$+H)

Example 55

4-{3-[(5-chloro-2-oxo-2H-[1,2']bipyridinyl-5'-ylmethyl)-amino]-1-imidazol-1-yl-propyl}-benzonitrile Step 1: 4-Imidazol-1-ylmethyl-benzonitrile To imidazole (7 gm, 103 mmol) suspended in degassed DMF (250 mL) under argon was added NaH 60% dispersion in mineral oil (4.53 gm, 113 mmol) with stirring for 10 minutes. A solution of 4-bromomethyl benzonitrile in 50 mL of DMF was added and the reaction was stirred for 16 hrs. The reaction was quenched with the addition of 20 mL of water and the solvent was removed in vacuo. The residue was suspended in methylene chloride (500 mL) and extracted 3 times with water (200 mL) and the organic layer was dried over magnesium sulfate, filtered, and the solvent was removed in vacuo. The residue was chromatographed on silica gel with methylene chloride to remove the oil followed by 95:5 methylene chloride: methanol. The resulting fractions where reduced to a small volume in vacuo and the product spontaneously crystallized. The crystals were filtered to give the desired product.

$^1$H NMR (400 MHz, CDCl$_3$) δ 7.64 (d, 2H); 7.59 (s, 1H); 7.20 (d, 2H); 7.18 (s,1H); 6.90 (s,1H) 5.20 (s,2H)

Step 2: tert-Butyl-(2-iodo-ethoxy)-dimethyl-silane

To 2-iodoethanol (20 gm, 116 mmol) suspended in methylene chloride (500 mL) was added dimethylaminopyridine (100 mg) followed by diisopropylethylamine (30 mL, 174 mmol) and tert-butyldimethylsilyl chloride (19 gm, 128 mmol). The reaction was stirred overnight and the solvent was removed in vacuo and the residue was passed through a short column of silica gel and eluted with 95:5 methylene chloride: methanol. The desired fractions were combined and the solvent was removed in vacuo to give the desired product.

$^1$H NMR (400 MHz, CDCl$_3$) δ 3.84 (dd, 2H); 3.20 (dd, 2H); 0.9 (m, 9H); 0.1 (m, 6H).

Step 3: 4-[3-(tert-butyl-dimethyl-silanyloxy)-1-imidazol-1-yl-propyl]-benzonitrile 4-Imidazol-1-ylmethyl-benzonitrile (5.5 gms,30 mmol) was suspended in freshly distilled THF (150 mL) in dry glassware and stirred under argon in a −60° C. dry ice acetone bath then Lithium bis(trimethylsilyl)amide 1 molar in THF (33 mL) was added slowly. The mixture was stirred for 30 minutes and the temperature was reduced to −78° C. A suspension of tert-butyl-(2-iodo-ethoxy)-dimethyl-silane (9.5 gm, 33 mmol) in 20 mL of THF was cooled to −78° C. and added via cannula to the first solution and the resulting mixture was allowed to slowly warm to ambient temperature. After 16 hours the reaction was quenched by the addition of 10 mL of water and the solvent was removed in vacuo. The residue was suspended in ethyl acetate (200 mL) and extracted 2 times with saturated aqueous sodium bicarbonate (100 mL), then water (100 mL), then saturated sodium chloride solution (100 mL). The organic solvent was removed in vacuo and the residue was chromatographed on silica gel using 1:3 ethyl acatate: hexanes. The desired fractions were combined and the solvent was removed in vacuo to give the desired product.

$^1$H NMR (400 MHz, CDCl$_3$) δ 7.64 (d, 2H); 7.59 (d, 1H); 7.25 (m, 2H); 7.10 (d,1H); 6.90 d,1H) 5.58 (m, 1H); 3.48 (m, 2H); 2.38 (m, 2H); 0.9 (m, 9H); 0.1 (m, 6H)

Step 4: 4-(3-Hydroxy-1-imidazol-1-yl-propyl)-benzonitrile

The 4-[3-(tert-butyl-dimethyl-silanyloxy)-1-imidazol-1-yl-propyl]-benzonitrile (2.0 gm, mmol) was suspended in acetonitrile (20 mL) in a teflon flask and HF/pyridine (4 mL) was added and the reaction was stirred for 1 hour. The reaction was quenched with cold aqueous sodium hydroxide and the resulting solution was concentrated in vacuo. The residue was dissolved in methylene chloride and chromatographed on silica gel eluting with 1:1 ethyl acetate:hexanes. The desired fractions were concentrated in vacuo to give the desired product as an oil.

$^1$H NMR (400 MHz, CD$_3$OD) δ 7.9 (s, 1H); 7.75 (d, 2H); 7.50 (d, 2H); 7.22 (s,1H); 7.00 (s,1H) 5.70 (m,1H); 3.50 (m, 1H); 3.40 (m, 1H); 2.50 (m, 1H); 2.4 (m, 1H)

Step 5: Methanesulfonic acid 3-(4-cyano-phenyl)-3-imidazol-1-yl-propyl ester

The 4-(3-hydroxy-1-imidazol-1-yl-propyl)-benzonitrile (1.4 gm, 6.16 mmol) was suspended in 2:1 methylene chloride: THF (100 mL) under argon and cooled to 0° C. in an ice bath. Methanesulfonylchloride (1 mL, 12.4 mmol) was added followed by diisopropylethylamine (3.22 mL, 18.5 mmol). The reaction was stirred for 4 hours and the solvent was removed in vacuo. The residue was suspended in ethyl acetate (200 mL) and extracted 2 times with saturated aqueous sodium bicarbonate (100 mL), then water (100 mL), then saturated sodium chloride solution (100 mL). The organic solvent was removed in vacuo and the residue was chromatographed on silica gel using using 1:3 ethyl acatate: hexanes. The desired fractions were concentrated in vacuo to give the desired product.

$^1$H NMR (400 MHz, CD$_3$OD) δ 7.9 (s, 1H); 7.75 (d, 2H); 7.50 (d, 2H); 7.22 (s,1H); 7.00 (s,1H) 5.70 (m,1H); 4.25 (m, 1H); 4.12 (m, 1H);3.0 (s, 3H); 2.75 (m, 1H); 2.7 (m, 1H)

Step 6: 4-(3-Azido-1-imidazol-1-yl-propyl)-benzonitrile

The methanesulfonic acid 3-(4-cyano-phenyl)-3-imidazol-1-yl-propyl ester (600 mg, 2 mmol) was suspended in degassed DMF under argon and sodium azide (650 mg, 10 mmol) was added and the reaction was stirred for 4 hours. The solvent was removed in vacuo and the residue was suspended in ethyl acetate (200 mL) and extracted 2 times with saturated aqueous sodium bicarbonate (100 mL), then water (100 mL), then saturated sodium chloride solution (100 mL). The organic solvent was removed in vacuo and the residue was chromatographed on silica gel eluting with 1:2 ethyl acatate: hexanes. The desired fractions were concentrated in vacuo to give the desired product.

$^1$H NMR (400 MHz, CDCl$_3$) δ 7.68 (d, 2H); 7.6 (s, 1H); 7.30 (d, 2H); 7.18 (s,1H); 6.95 (s,1H) 5.42 (m,1H); 3.4 (m, 1H); 3.22 (m, 1H); 2.4 (m, 2H)

Step 7: 4-(3-Amino-1-imidazol-1-yl-propyl)-benzonitrile

The 4-(3-azido-1-imidazol-1-yl-propyl)-benzonitrile (490 mg, 1.9 mmol) was suspended in methanol (20 mL) and placed under argon. 10% Palladium on Carbon catalyst was carefully added under argon and the solution was evacuated under vacuum to bubbling and then purged with argon 3 times. The suspension was evacuated again and then a balloon filled with hydrogen was opened to the reaction. The reaction was left under hydrogen at room pressure for 16 hours. The reaction was evacuated again to bubbling and purged with argon. The catalyst was filtered off through a bed of celite under argon. The supernatant was concentrated in vacuo to give the desired product.

Step 8: 4-{3-[(5-chloro-2-oxo-2H-[1,2']bipyridinyl-5'-ylmethyl)-amino]-1-imidazol-1-yl-propyl}-benzonitrile The 4-(3-amino-1-imidazol-1-yl-propyl)-benzonitrile (50 mg, 0.22 mmol) was suspended in methanol under argon and the Example 23, Step 2 (52 mg, 0.22 mmol) was added followed by acetic acid (80 μl, 6 eq) and 4A crushed molecular sieves (20 mg). The reaction was stirred for 1 hour and then sodium cyanoborohydride (21 mg, 0.25 mmol) was added. The reaction was stirred for 16 hours. The solids were filtered off through a bed of celite and the supernatant was concentrated in vacuo. The residue was chromatographed on silica gel eluting with 95:5 methylene chloride: methanol. The desired fractions were combined and the solvent was removed in vacuo. The residue was redissolved in methanol (2 mL) and HCl saturated ether (100 μl) was added. The solvent was removed in vacuo and the residue was precipitated from ethyl acetate and hexane. The resulting solid was filtered and dried in vacuo to give the desired product as the HCl salt.

$^1$H NMR (400 MHz, CDCl$_3$) δ 8.44 (d, 1H);8.0 (d, 1H); 7.87 (d,1H); 7.78 (dd,1H); 7.65 (s, 1H); 7.63 (s, 1H); 7.60 (s, 1H); 7.35 (dd, 1H); 7.27 (d,2H); 7.12 (s,1H); 6.93 (s, 1H); 6.62 (d, 1H) 5.54 (m,1H); 3.80 (s, 2H); 2.67 (m, 1H); 2.58 (m, 1H); 2.38 (m, 1H); 2.30 (m, 1H) Analysis: % Calc for C$_{24}$H$_{21}$N$_6$OCl.2.00 HCl,1.55H$_2$O; C 52.81, H 4.82, N 15.40; % Found: C 52.79, H 4.91, N 14.84; FAB mass spec M+H=445

Example 56

2-Methoxy-4-{3-[4-(2-oxo-2H-pyridin-1-yl)-benzyl]-3H-imidazol-4-ylmethyl}-benzonitrile The title compound was prepared according to the procedure described in example 1 step 3 using the imidazole from Example 49 Step 2

Analysis: % Calc for C$_{24}$H$_{20}$N$_4$O$_2$ 0.2CHCl$_3$, C 57.42, H 3.67, N 19.13; % Found: C 57.67, H 4.03, N 19.17; FABMS 403 (MH$^+$)

Example 57

4-[3-(5-chloro-2-oxo-2H-[1,2']bipyridinyl-5'-ylmethyl)-3H-imidazol-4-ylmethyl]-2-(2,2,2-trifluoro-ethoxy)-benzonitrile The title compound was prepared according to the procedure described in example 10 step 3 and 2-(2,2,2-trifluoro-ethoxy)-4-(1-trityl-1H-imidazol-4-ylmethyl)-benzonitrile (which was prepared from the bromide from Example 40 Step 3)

$^1$H NMR (400 MHz, CD$_3$OD) δ 9.10 (s, 1H), 8.36 (d, J=1.8 Hz,1H), 8.02(d, J=2.7 Hz, 1H), 7.81 (d, J=8.4 Hz, 1H), 7.76 (dd, J=2.4 and 8.4 Hz, 1H), 7.60 (dd, J=2.9 and 9.9 Hz, 1H), 7.54 (d, J=7.9 Hz, 1H), 7.49(s, 1H), 7.04( s, 1H), 6.90(d, J=7.8 Hz, 1H) 6.64 (d, J=9.9 Hz, 1H), 5.53 (s, 2H) 4.69 (q, J=8.2 Hz, 2H) and 4.22(s, 2H) ppm. FAB HRMS exact mass calcd for C$_{24}$H$_{18}$N$_5$O$_2$ClF$_3$ 500.1096 (MH$^+$); found 500.1087.

Example 58

In Vitro Inhibition of Ras Farnesyl Transferase

Assays offarnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Examples 1–57 were tested for inhibitory activity against human FPTase by the assay described above and were found to have IC$_{50}$ of <50 μM.

Example 59

In Vivo Ras Farnesylation Assay

The cell line used in this assay is a v-ras line derived from either Rat1 or NIH$_3$T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 60

In Vivo Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound of the formula A$^1$:

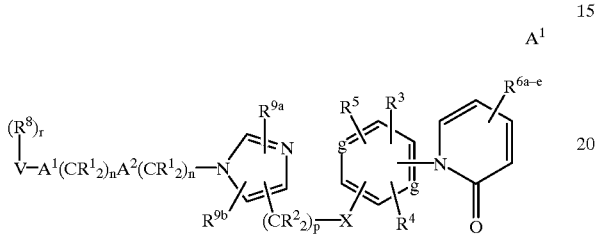

wherein:

R$^1$ and R$^2$ are independently selected from:
a) hydrogen,
b) aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, R$^{11}$C(O)O—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$C(O)NR$^{10}$—,
c) unsubstituted or substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$C(O)—NR$^{10}$—;

R$^3$, R$^4$ and R$^5$ are independently selected from:
a) hydrogen,
b) unsubstituted or substituted aryl, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$C(O)O—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N— C(NR$^{10}$)—, CN, R$^{10}$C(O)—, N$_3$, —N(R$^{10}$)$_2$, and R$^{11}$OC(O)—NR$^{10}$—;

R$^{6a}$, R$^{6b}$, R$^{6c}$, R$^{6d}$ and R$^{6e}$ are independently selected from:
a) hydrogen,
b) unsubstituted or substituted aryl, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$O—, (R$^{10}$)$_2$NC(O)—, R$^{11}$S(O)$_2$NR$^{10}$—, (R$^{10}$)$_2$NS(O)$_2$—, R$^{11}$C(O)O—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^7$ is selected from: H; C$_{1-4}$ alkyl, C$_{3-6}$ cycloalkyl, aryl, aroyl, arylsulfonyl, unsubstituted or substituted with:
a) C$_{1-4}$ alkoxy,
b) aryl, c) 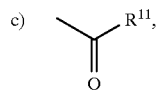

d) —SO$_2$R$^{11}$,
e) N(R$^{10}$)$_2$ or
f) C$_{1-4}$ perfluoroalkyl;

R$^8$ is independently selected from:
a) hydrogen,
b) aryl, substituted aryl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, NO$_2$, R$^{10}$C(O)—, N$_3$, —N(R$^{10}$)$_2$, or R$^{11}$C(O)NR$^{10}$—, and
c) C$_1$–C$_6$ alkyl unsubstituted or substituted by aryl, cyanophenyl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, R$^{10}$C(O)—, N$_3$, —N(R$^{10}$)$_2$, or R$^{10}$C(O)NH—;

R$^{9a}$ and R$^{9b}$ are independently selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O))NR$^{10}$—, (R$^{10}$)$_2$NC(O)—, R$^{10}$$_2$N—C(NR$^{10}$)—, CN, R$^{10}$C(O)—, N$_3$, —N$_1$(R$^{10}$)$_2$, or R$^{11}$OC(O)NR$^{10}$—;

R$^{10}$ is independently selected from hydrogen, C$_1$–C$_6$ alkyl, amino-C$_1$–C$_6$ alkyl, N-(unsubstituted or substituted benzolyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl;

R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, aryl, substituted aryl, C$_1$–C$_6$ perfluoroalkyl, 2-aminoethyl and 2,2,2-trifluoroethyl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

g is independently selected from: CH and N;

V is selected from: aryl and pyridyl;

X is a bond, —CH=CH—, O, —C(=O)—, —C(O)NR$^7$—, —NR$^7$C(O)—, —C(O)O—, —OC(O)—,

—C(O)NR$^7$C(O)—, —NR$^7$—, —S(O)$_2$N(R$^{10}$)—, —N(R$^{10}$)S(O)$_2$— or —S(=O)$_m$—;

m is 0, 1 or 2;

n is independently 0, 1, 2, 3 or 4;

p is independently 0, 1, 2, 3 or 4;

r is 0 to 5; and or a pharmaceutically acceptable salt thereof.

2. A compound of the formula A$^2$:

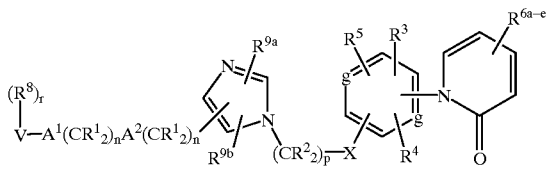

wherein:

R$^1$ and R$^2$ are independently selected from:
a) hydrogen,
b) aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, R$^{11}$C(O)O—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted or substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^3$, R$^4$ and R$^5$ are independently selected from:
a) hydrogen,
b) unsubstituted or substituted aryl, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$C(O)O—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^{6a}$, R$^{6b}$, R$^{6c}$, R$^{6d}$ and R$^{6e}$ are independently selected from:
a) hydrogen,
b) unsubstituted or substituted aryl, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$S(O)$_2$—, R$^{11}$C(O)O—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^7$ is selected from: H; C$_{1-4}$ alkyl, C$_{3-6}$ cycloalkyl, aryl, aroyl, arylsulfonyl, unsubstituted or substituted with:
a) C$_{1-4}$ alkoxy,
b) aryl, c) 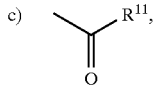

d) —SO$_2$R$^{11}$,
e) N(R$^{10}$)$_2$ or
f) C$_{1-4}$ perfluoroalkyl;

R$^8$ is independently selected from:
a) hydrogen,
b) aryl, substituted aryl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{11}$S(O)NR$^{10}$—, (R$^{10}$)$_2$NS(O)$_2$—, R$^{10}$$_2$N—C(NR$^{10}$)—, CN, R$^{10}$C(O)—, N$_3$, —N(R$^{10}$)$_2$, or R$^{10}$OC(O)NH—;

R$^{9a}$ and R$^{9b}$ are independently selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, amino-C$_1$–C$_6$ alkyl, N-(unsubstituted or substituted benzolyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl, R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, aryl, substituted aryl, C$_1$–C$_6$ perfluoroalkyl, 2-aminoethyl and 2,2,2-trifluoroethyl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

g is independently selected from: CH and N;

V is selected from: aryl and pyridyl;

X is a bond, —CH=CH—, O, —C(=O)—, —C(O)NR$^7$—, —NR$^7$C(O)—, —C(O)O—, —OC(O)—, —C(O)NR$^7$C(O)—, NR$^7$—, —S(O)$_2$N(R$^{10}$)—, —N(R$^{10}$)S(O)$_2$— or —S(=O)$_m$—;

m is 0, 1 or 2;

n is independently 0, 1, 2, 3 or 4;

p is independently 0, 1, 2, 3 or 4;

r is 0 to 5; and or a pharmaceutically acceptable salt thereof.

3. The compound according to claim 1 of the formula $B^1$:

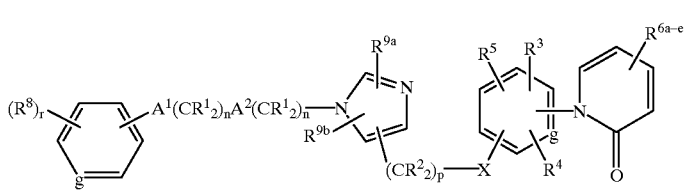

wherein:

$R^1$ and $R^2$ are independently selected from:
  a) hydrogen,
  b) aryl, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted or substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^3$, $R^4$ and $R^5$ are independently selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$— $C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{11}C(O)O$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}{}_2N$—$C(NR^{10})$—, CN, $R^{10}C(O)$—, —$N(R^{10})_2$, and $R^{11}OC(O)$—$NR^{10}$—;

$R^7$ is selected from: H; $C_{1-4}$ alkyl, $C_{3-6}$ cycloalkyl, aryl, aroyl, arylsulfonyl, unsubstituted or substituted with:
  a) $C_{1-4}$ alkoxy,
  b) aryl,
  c) 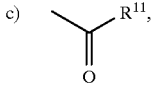
  d) —$SO_2R^{11}$,
  e) $N(R^{10})_2$ or
  f) $C_{1-4}$ perfluoroalkyl;

$R^8$ is independently selected from:
  a) hydrogen,
  b) aryl, substituted aryl, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by aryl, cyanophenyl, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}{}_2N$—$C(NR^{10})$—, CN, $R^{10}C(O)$—, $N_3$, —$N(R^{10})_2$, or $R^{10}OC(O)NH$—;

$R^{9a}$ and $R^{9b}$ are independently selected from:
  a) hydrogen,
  b) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, amino-$C_1$–$C_6$ alkyl, N-(unsubstituted or substituted benzolyl)-amino-$C_1$–$C_6$ alkyl, $(C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroetyl;

$A^1$ and $A^2$ are independently selected from: a bond, —CH═CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

g is independently selected from: CH and N;

X is a bond, —CH=CH—, O, —C(=O)—, —C(O)NR$^7$—, —NR$^7$C(O)—, —C(O)O—, —OC(O)—, —C(O)NR$^7$C(O)—, —NR$^7$—, —S(O)$_2$N(R$^{10}$)—, —N(R$^{10}$)S(O)$_2$— or —S(=O)$_m$—;

m is 0, 1 or 2;

n is independently 0, 1, 2, 3 or 4;

p is independently 0, 1, 2, 3 or 4;

r is 0 to 5; and or a pharmaceutically acceptable salt thereof.

4. The compound according to claim 2 of the formula C$^1$:

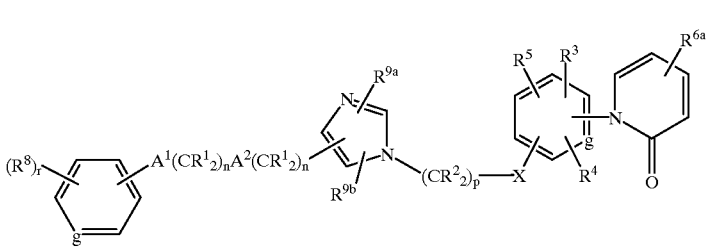

wherein:

R$^1$ and R$^2$ are independently selected from:
  a) hydrogen,
  b) aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, R$^{11}$C(O)O—, (R$^{10}$)$_2$NC(O)—, R$^{10}_2$N—C(NR$^{10}$)—, CN, NO$_2$, R$^{10}$C(O)—, N$_3$, —N(R$^{10}$)$_2$, or R$^{11}$OC(O)NR$^{10}$—,
  c) unsubstituted or substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}_2$N—C(NR$^{10}$)—, CN, R$^{10}$C(O)—, N$_3$, —N(R$^{10}$)$_2$, and R$^{11}$C(O)—NR$^{10}$—;

R$^3$, R$^4$ and R$^5$ are independently selected from:
  a) hydrogen,
  b) unsubstituted or substituted aryl, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$C(O)O—, R$^{10}_2$N—C(NR$^{10}$)—, CN, NO$_2$, R$^{10}$C(O)—, N$_3$, —N(R$^{10}$)$_2$, or R$^{11}$OC(O)NR$^{10}$—,
  c) unsubstituted C$_1$–C$_6$ alkyl,
  d) substituted C$_1$C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}_2$N— C(NR$^{10}$)—, CN, R$^{10}$C(O)—, N$_3$, —N(R$^{10}$)$_2$, and R$^{11}$OC(O)—NR$^{10}$—;

R$^{6a}$, R$^{6b}$, R$^{6c}$, R$^{6d}$ and R$^{6e}$ are independently selected from:
  a) hydrogen,
  b) unsubstituted or substituted aryl, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{11}$C(O)O—, R$^{10}_2$N—C(NR$^{10}$)—, CN, NO$_2$, R$^{10}$C(O)—, N$_3$, —N(R$^{10}$)$_2$, or R$^{11}$OC(O)NR$^{10}$—,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}_2$N—C (NR$^{10}$)—, CN, R$^{10}$C(O)—, N$_3$, —N(R$^{10}$)$_2$, and R$^{11}$OC(O)—NR$^{10}$—;

R$^7$ is selected from: H; C$_{1-4}$ alkyl, C$_{3-6}$ cycloalkyl, aryl, aroyl, arylsulfonyl, unsubstituted or substituted with:
  a) C$_{1-4}$ alkoxy,
  b) aryl,
  c) 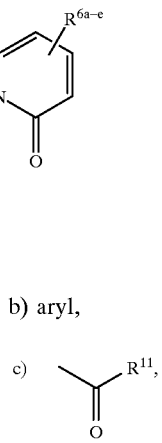
  d) —SO$_2$R$^{11}$,
  e) N(R$^{10}$)$_2$ or
  f) C$_{1-4}$ perfluoroalkyl;

R$^8$ is independently selected from:
  a) hydrogen,
  b) aryl, substituted aryl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC (O)—, R$^{11}$S(O)$_2$NR$^{10}$—, (R$^{10}$)$_2$NS(O)$_2$—, R$^{10}_2$N—C(NR$^{10}$)—, CN, NO$_2$, R$^{10}$C(O)—, N$_3$, —N(R$^{10}$)$_2$, or R$^{11}$OC(O)NR$^{10}$—, and
  c) C$_1$–C$_6$ alkyl unsubstituted or substituted by aryl, cyanophenyl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{10}_2$N— C(NR$^{10}$)—, CN, R$^{10}$C(O)—, N$_3$, —N(R$^{10}$)$_2$, or R$^{10}$OC(O)NH—;

R$^{9a}$ and R$^{9b}$ are independently selected from:
  a) hydrogen,
  b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}_2$N—C(NR$^{10}$)—, CN, NO$_2$, R$^{10}$C(O)—, N$_3$, —N(R$^{10}$)$_2$, or R$^{11}$OC(O)NR$^{10}$—, and
  c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, amino-C$_1$–C$_6$ alkyl, N-(unsubstituted or substituted benozyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl;

111

R¹¹ is independently selected from $C_1$–$C_6$ alkyl and aryl;

R¹² is independently selected from hydrogen, $C_1$–$C_6$ alkyl, $C_1$–$C_6$ aralkyl, $C_1$–$C_6$ substituted aralkyl, aryl, substituted aryl, $C_1$–$C_6$ perfluoroalkyl, 2-aminoethyl and 2,2,2-trifluoroethyl;

A¹ and A² are independently selected from: a bond, —CH=CH—, —C≡C—, —C(O)—, —C(O)NR¹⁰—, —NR¹⁰C(O)—, O, —N(R¹⁰)—, —S(O)₂N(R¹⁰)—, —N(R¹⁰)S(O)₂—, or S(O)ₘ—;

g is independently selected from: CH and N;

X is a bond, —CH=CH—, O, —C(=O)—, —C(O)NR⁷—, —NR⁷C(O)—, —C(O)O—, —OC(O)—, —C(O)NR⁷C(O)—, —NR⁷—, —S(O)₂N(R¹⁰)—, —N(R¹⁰)S(O)₂— or —S(=O)ₘ—;

m is 0, 1 or 2;

n is independently 0, 1, 2, 3 or 4;

p is independently 0, 1, 2, 3 or 4;

r is 0 to 5; and or a pharmaceutically acceptable salt thereof.

5. A compound selected from:

4-{3-[4-(-2-Oxo-2-H-pyridin-1-yl)benzyl]-3-H-imidazol-4-ylmethyl}benzonitrile;

4-{3-[4-(3-Methyl-2-oxo-2-H-pyridin-1-yl)benzyl]-3-H-imidazol-4-ylmethyl}benzonitrile;

4-{3-[2-Methoxy-4-(2-oxo-2-H-pyridin-1-yl)-benzyl]-3-H-imidazol-4-ylmethyl}-benzonitrile;

4-{1-[4-(5-Chloro-2-oxo-2H-pyridin-1-yl)-benzyl]-1H-imidazol-2-ylmethyl}-benzonitrile;

4-[1-(2-Oxo-2H-[1,2']bipyridinyl-5'-ylmethyl)-1H-imidazol-2-ylmethyl]-benzonitrile;

4-[1-(5-Chloro-2-oxo-2H-[1,2']bipyridinyl-5'-ylmethyl)-1H-imidazol-2-ylmethyl]-benzonitrile;

4-[3-(6-Methyl-2-oxo-2-H-[1,2']bipyridinyl-5'-ylmethyl)-3H-imidazol-4-ylmethyl]-benzonitrile;

4-[1-(5-Trifluoromethyl-2-oxo-2H-[1,2']bipyridinyl-5'-ylmethyl)-1H-imidazol-2-ylmethyl]-benzonitrile;

4-[1-(3,5-dibromo-2-oxo-2H-[1,2']bipyridinyl-5'-ylmethyl)-1H-imidazol-2-ylmethyl]-benzonitrile;

4-[1-(3-Bromo-2-oxo-2H-[1,2']bipyridinyl-5'-ylmethyl)-1H-imidazol-2-ylmethyl]-benzonitrile;

4-[1-(5-Bromo-2-oxo-2H-[1,2']bipyridinyl-5'-ylmethyl)-1H-imidazol-2-ylmethyl]-benzonitrile;

4-[1-(5-Cyano-2-oxo-2H-[1,2']bipyridinyl-5'-ylmethyl)-1H-imidazol-2-ylmethyl]-benzonitrile;

4-[1-(3,5-Dichloro-2-oxo-2H-[1,2']bipyridinyl-5'-ylmethyl)-1H-imidazol-2-ylmethyl]-benzonitrile;

(R,S) 4-{[3-(5-chloro-2-oxo-2H-[1,2']bipyridinyl-5'-ylmethyl)-3H-imidazol-4-yl]hydroxy-methyl}-benzonitrile;

(R,S) 4-{[3-(5-chloro-2-oxo-2H-[1,2']bipyridinyl-5'-ylmethyl)-3H-imidazol-4-yl]-fluoro-methyl}-benzonitrile;

4-[3-(5-Chloro-2-oxo-2H-[1,2']bipyridinyl-5'-ylmethyl)-3H-imidazole-4-carbonyl]-benzonitrile;

4-{[3-(5-chloro-2-oxo-2H-[1,2']bipyridinyl-5'-ylmethyl)-3H-imidazol-4yl]-methoxy-methyl}-benzonitrile;

(R,S)4-[1-(5-Chloro-2-oxo-2H-[1,2']bipyridinyl-5'-ylmethyl)-1H-imidazol-2-ylbutyloxy-methyl]-benzonitrile;

4-[5-(5-chloro-2-oxo-2H-[1,2']bipyridinyl-5'-ylmethyl)-imidazol-1-ylmethyl]-benzonitrile;

5'-(3-Benzyl-3H-imidazol-4-ylmethyl)-5-chloro-[1,2']bipyridinyl-2-one;

112

(R,S) Acetic acid (5-chloro-2-oxo-2H-[1,2']bipyridinyl-5'-yl)-[3-(4-cyano-benzyl)-3H-imidazol-4-yl]-methyl ester;

4-{5-[(5-chloro-2-oxo-2H-[1,2']bipyridinyl-5'-yl)-hydroxy-methyl]-imidazol-1-ylmethyl}-benzonitrile;

(R,S) 4-{5-[(5-chloro-2-oxo-2H-[1,2']bipyridinyl-5'-yl)-methoxy-methyl]-imidazol-1-ylmethyl}-benzonitrile;

(R,S) 4-{5-[butoxy-(5-chloro-2-oxo-2H-[1,2']bipyridinyl-5'-yl)-methyl]-imidazol-1-ylmethhyl}-benzonitrile;

1-{4-[5-(4-Cyanophenyloxy)imidazol-1-ylmethyl]phenyl}-1H-pyridin-2-one;

1-{4-[5-(4-Cyanophenyloxy-3-methoxy)imidazol-1-ylmethyl]phenyl}-1H-pyridin-2-one;

4-{3-[5-(5-Chloro-2-oxo-2H-pyridin-1-yl)-pyrazin-2-ylmethyl]-3H-imidazol-4-ylmethyl}-benzonitrile;

2-(2-Amino-ethoxy)-4-[5-(5-chloro-2-oxo-2H-[1,2']bipyridinyl-5'-ylmethyl)-imidazol-1-ylmethyl]-benzonitrile;

4-[5-(5-Chloro-2-oxo-2H-[1,2']bipyridinyl-5'-ylmethyl)-imidazol-1-ylmethyl]-2-(2-dimethylarmino-ethoxy)-benzonitrile;

N-(2-{5-[5-(5-chloro-2-oxo-2H-[1,2']bipyridinyl-5'-ylmethyl)-imidazol-1-ylmethyl]2-cyano-phenoxy}-ethyl)-acetamide;

3-Chloro-N-(2-{5-[5-(5-chloro-2-oxo-2H-[1,2']bipyridinyl-5'-ylmethyl)-imidazol-1-ylmethyl]-2-cyano-phenoxy}-ethyl)-benzamide;

4-[5-(5-Chloro-2-oxo-2H-[1,2']bipyridinyl-5'-ylmethyl)-imidazol-1-ylmethyl]-2-(2,2,2-trifluoro-ethoxy)-benzonitrile;

2-Benzyloxy-4-[5-(5-chloro-2-oxo-2H-[1,2']bipyridinyl-5'-ylmethyl)-imidazol-1-ylmethyl]-benzonitrile;

4-[5-(5-Chloro-2-oxo-2H-[1,2']bipyridinyl-5'-ylmethyl)-imidazol-1-ylmethyl]-2-phenethyloxy-benzonitrile;

4-[5-(5-Chloro-2-oxo-2H-[1,2']bipyridinyl-5'-ylmethyl)-imidazol-1-ylmethyl]-2-(4-phenyl-butoxy)-benzonitrile;

4-[5-(5-chloro-2-oxo-2H-[1,2']bipyridinyl-5'-ylmethyl)-imidazol-1-ylmethyl]-2-(3-phenyl-propoxy)-benzonitrile;

4-[5-(5-Chloro-2-oxo-2H-[1,2']bipyridinyl-5'-ylmethyl)-imidazol-1-ylmethyl]-2-methoxy-benzonitrile;

5-[5-(5-Chloro-2-oxo-2H-[1,2']bipyridinyl-5'-ylmethyl)-imidazol-1-ylmethyl]-biphenyl-2-carbonitrile;

4-[5-(5-Chloro-2-oxo-2H-[1,2']bipyridinyl-5'-ylmethyl)-imidazol-1-ylmethyl]-phthalonitrile;

5-[5-(5-Chloro-2-oxo-2H-[1,2']bipyridinyl-5'-ylmethyl)-imidazol-1-ylmethyl]-pyridine-2-carbonitrile;

4-[3-(5-chloro-2-oxo-2H-[1,2']bipyridinyl-5'-ylmethyl)-3H-imidazol-4-ylmethyl]-2-methoxy-benzonitrile;

4-[3-(5-chloro-2-oxo-2H-[1,2']bipyridinyl-5'-ylmethyl)-3H-imidazol-4-ylmethyl]-phthalonitrile;

5-[5-(5-Chloro-2-oxo-2H-[1,2']bipyridinyl-5'-ylmethyl)-imidazol-1-ylmethyl]-2-methoxy-benzonitrile;

4-[3-(5-chloro-2-oxo-2H-[1,2']bipyridinyl-5'-ylmethyl)-3H-imidazol-4-ylmethyl]-biphenyl-2-carbonitrile;

5-[3-(5-chloro-2-oxo-2H-[1,2']bipyridinyl-5'-ylmethyl)-3H-imidazol-4-ylmethyl]-biphenyl-2-carbonitrile;

2-Methoxy-4-{3-[4-(2-oxo-2H-pyridin-1-yl)-benzyl]-3H-imidazol-4-ylmethyl}-benzonitrile;

4-[3-(5-chloro-2-oxo-2H-[1,2']bipyridinyl-5'-ylmethyl)-3H-imidazol-4-ylmethyl]-2-(2,2,2-trifluoro-ethoxy)-benzonitrile;

or a pharmaceutically acceptable salt thereof.

6. The compound according to claim 5 which is:

4-[1-(5-Chloro-2-oxo-2H-[1,2']bipyridinyl-5'-ylmethyl)-1H-imidazol-2-ylmethyl]-benzonitrile

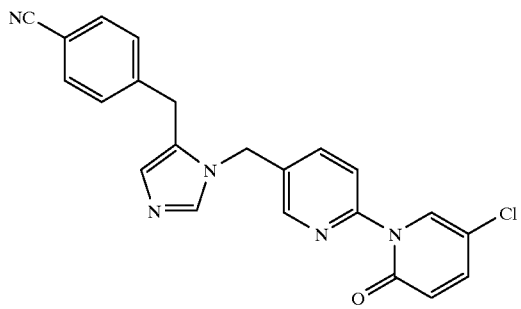

or a pharmaceutically acceptable salt thereof.

7. The compound according to claim 5 which is:

4-[1-(5-Bromo-2-oxo-2H-[1,2']bipyridinyl-5'-ylmethyl)-1H-imidazol-2-ylmethyl]-benzonitrile

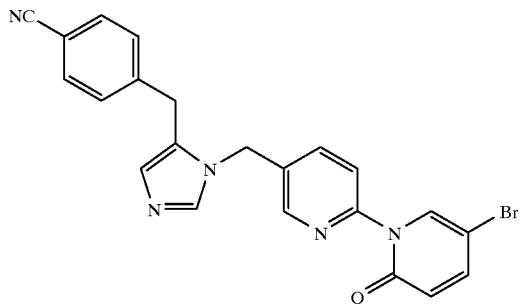

or a pharmaceutically acceptable salt thereof.

8. The compound according to claim 5 which is:

4-[5-(5-chloro-2-oxo-2H-[1,2']bipyridinyl-5'-ylmethyl)-imidazol-1-ylmethyl]-benzonitrile

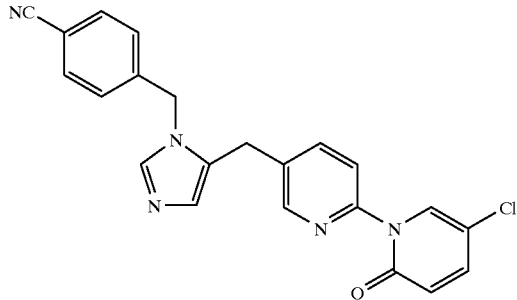

or a pharmaceutically acceptable salt thereof.

9. The compound according to claim 5 which is:

5-[5-(5-Chloro-2-oxo-2H-[1,2']bipyridinyl-5'-ylmethyl)-imidazol-1-ylmethyl]-pyridine-2-carbonitrile

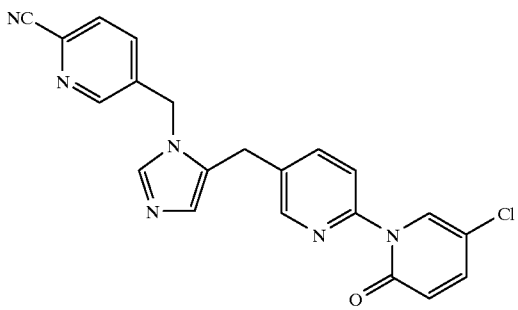

or a pharmaceutically acceptable salt thereof.

10. The compound according to claim 5 which is:

4-{3-[5-(5-Chloro-2-oxo-2H-pyridin-1-yl)-pyrazin-2-ylmethyl]-3H-imidazol-4-ylmethyl}-benzonitrile

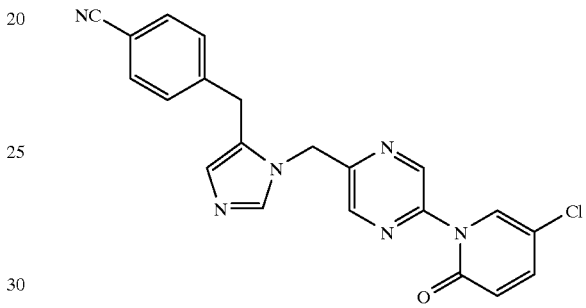

or a pharmaceutically acceptable salt thereof.

11. The compound according to claim 5 which is:

4-[3-(5-chloro-2-oxo-2H-[1,2']bipyridinyl-5'-ylmethyl)-3H-imidazol-4-ylmethyl]-2-methoxy-benzonitrile

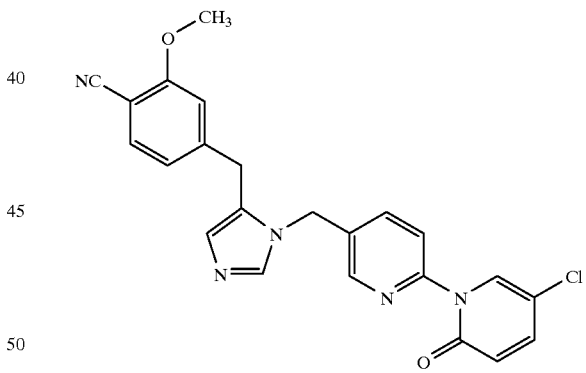

or a pharmaceutically acceptable salt thereof.

12. A pharmaceutical composition comprising a pharmaceutical carrier, and dispersed therein, a therapeutically effective amount of a compound of claim 1.

13. A pharmaceutical composition comprising a pharmaceutical carrier, and dispersed therein, a therapeutically effective amount of a compound of claim 2.

14. A pharmaceutical composition comprising a pharmaceutical carrier, and dispersed therein, a therapeutically effective amount of a compound of claim 5.

15. A pharmaceutical composition made by combining the compound of claim 1 and a pharmaceutically acceptable carrier.

16. A process for making a pharmaceutical composition comprising combining a compound of claim 1 and a pharmaceutically acceptable carrier.

17. A pharmaceutical composition made by combining the compound of claim 2 and a pharmaceutically acceptable carrier.

18. A process for making a pharmaceutical composition comprising combining a compound of claim 2 and a pharmaceutically acceptable carrier.

19. A method for inhibiting farnesyl-protein transferase in treating cancer which comprises administering to a mammal in need thereof a therapeutically effective amount of a composition of claim 12.

20. A method for inhibiting farnesyl-protein transferase in treating cancer which comprises administering to a mammal in need thereof a therapeutically effective amount of a composition of claim 13.

21. A method for inhibiting farnesyl-protein transferase in treating cancer which comprises administering to a mammal in need thereof a therapeutically effective amount of a composition of claim 14.

* * * * *

UNITED STATES PATENT AND TRADEMARK OFFICE
CERTIFICATE OF CORRECTION

Page 1 of 5

PATENT NO. : 5,939,439
DATED : August 17, 1999
INVENTOR(S) : Neville J. Anthony, Ian M. Bell, Robert P. Gomez, Michelle Sparks Kuo, William C. Lumma, Jr., John S. Wai and Steven D. Young It is certified that error appears in the above-identified patent and that said Letters Patent is hereby corrected as shown below:

ON THE TITLE PAGE:

Item [75] Inventors:

-- Neville J. Anthony, Hatfield; Ian M. Bell, Harleysville; Robert P. Gomez, Perkasie; Michelle Sparks Kuo, Gwynedd Valley; William C. Lumma, Jr., Pennsberg; John S. Wai, Harleysville; Steven D. Young, Lansdale, all of Pa. --

Column 103, Claim 1, line 32, should read:

-- $CN, NO_2, R^{10}C(O)-, N_3, -N(R^{10})_2$, or $R^{11}OC(C)$ --

Column 103, Claim 1, line 40, should read:

-- $-N(R^{10})_2$, and $R^{11}OC(O)-NR^{10}-$; --

Column 103, Claim 1, line 54, should read:

-- $R^{11}S(O)_m-, R^{10}C(O)NR^{10}-, (R^{10})_2NC(O)-,$ --

Column 103, Claim 1, line 63, should read:

-- $NR^{10}-, (R^{10})_2NC(O)-, R^{11}S(O)_2NR^{10}-, (R^{10})_2$ --

UNITED STATES PATENT AND TRADEMARK OFFICE
CERTIFICATE OF CORRECTION

PATENT NO. : 5,939,439
DATED : August 17, 1999
INVENTOR(S) : Neville J. Anthony, Ian M. Bell, Robert P. Gomez, Michelle Sparks Kuo, William C. Lumma, Jr., John S. Wai and Steven D. Young It is certified that error appears in the above-identified patent and that said Letters Patent is hereby corrected as shown below:

Column 104, claim 1, line 20, should read:

--     e)     $N(R^{10})_2$ or --

Column 104, claim 1, line 29, should read:

-- or $R^{11}OC(O)NR^{10}$-, and --

Column 104, claim 1, line 35, should read:

-- $(NR^{10})$-, CN, $R^{10}C(O)$-, $N_3$, -$N(R^{10})_2$, or $R^{10}OC$ --

Column 104, claim 1, lines 45-46, should read:

-- $(O)NR^{10}$-, $(R^{10})_2NC(O)$-, $R^{10}{}_2N$-$C(NR^{10})$-,
$CN$, $R^{10}C(O)$-, $N_3$, -$N(R^{10})_2$, or $R^{11}OC(O)$ --

Column 105, claim 2, line 26, should read:

-- $R^{11}C(O)O$-, $(R^{10})_2NC(O)$-, $R^{10}{}_2N$-$C(NR^{10})$-, --

Column 105, claim 2, line 33, should read:

-- $R^{11}S(O)_m$-, $R^{10}C(O)NR^{10}$-, $(R^{10})_2NC(O)$-, --

UNITED STATES PATENT AND TRADEMARK OFFICE
CERTIFICATE OF CORRECTION

PATENT NO. : 5,939,439

Page 3 of 5

DATED : August 17, 1999

INVENTOR(S) : Neville J. Anthony, Ian M. Bell, Robert P. Gomez, Michelle Sparks Kuo, William C. Lumma, Jr., John S. Wai and Steven D. Young It is certified that error appears in the above-identified patent and that said Letters Patent is hereby corrected as shown below:

Column 105, claim 2, line 59, should read:

-- $NS(O)_2-$, $R^{11}C(O)O-$, $R^{10}_2N-C(NR^{10})-$, CN, --

Column 106, claim 2, line 22, should read:

-- $(O)-$, $R^{11}S(O)_2NR^{10}-$, $(R^{10})_2NS(O)_2-$, $(R^{10})_2N-$, --

Column 106, claim 2, line 29, should read:

-- $R^{11}S(O)_2NR^{10}-$, $(R^{10})_2NS(O)_2-$, $R^{10}_2N-$ --

Column 106, claim 2, lines 57-58, should read:

-- $-NR^{10}C(O)-$, O, $-N(R^{10})-$, $-S(O)_2N(R^{10})-$, $-N(R^{10})S(O)_2-$, or $S(O)_m$; --

Column 106, claim 2, line 64, should read:

-- $-C(O)NR^7C(O)-$, $NR^7-$, $-S(O)_2N(R^{10})-$, $-N(R^{10})$ --

Column 107, claim 3, line 66, should read:

-- $(NR^{10})-$, CN, $R^{10}C(O)-$, $N_3$, $-N(R^{10})_2$, and --

UNITED STATES PATENT AND TRADEMARK OFFICE
CERTIFICATE OF CORRECTION

PATENT NO. : 5,939,439
DATED : August 17, 1999
INVENTOR(S) : Neville J. Anthony, Ian M. Bell, Robert P. Gomez, Michelle Sparks Kuo, William C. Lumma, Jr., John S. Wai and Steven D. Young It is certified that error appears in the above-identified patent and that said Letters Patent is hereby corrected as shown below:

Column 108, claim 3, line 63, should read:

-- and 2,2,2-trifluoroethyl; --

Column 109, claim 4, line 41, should read:

-- $-N(R^{10})_2$, and $R^{11}OC(O)-NR^{10}-$; --

Column 109, claim 4, line 51, should read:

-- d) substituted $C_1-C_6$ alkyl wherein the substituent on the --

Column 109, claim 4, line 55, should read:

-- $(O)NR^{10}-$, $(R^{10})_2NC(O)-$, $R^{10}_2N-C(NR^{10})-$, --

Column 109, claim 4, line 64, should read:

-- $NR^{10}-$, $(R^{10})_2NC(O)-$, $R^{11}S(O)_2NR^{10}-$, $(R^{10})_2$ --

Column 110, claim 4, line 64, should read:

-- tuted benzolyl)-amino-$C_1-C_6$ alkyl, $(C_1-C_6$ alkyl$)_2$- --

UNITED STATES PATENT AND TRADEMARK OFFICE
CERTIFICATE OF CORRECTION

PATENT NO. : 5,939,439
DATED : August 17, 1999
INVENTOR(S) : Neville J. Anthony, Ian M. Bell, Robert P. Gomez, Michelle Sparks Kuo, William C. Lumma, Jr., John S. Wai and Steven D. Young It is certified that error appears in the above-identified patent and that said Letters Patent is hereby corrected as shown below:

Column 111, claim 5, line 60, should read:

--      3H-imidazol-4-yl]-methoxy-methyl}-benzonitrile;      --

Column 112, claim 5, line 9, should read:

--      bipyridinyl-5'-yl)-methyl]-imidazol-1-ylmethyl}-      --

Column 112, claim 5, line 22, should read:

--      imidazol-1-ylmethyl]-2-(2-dimethylamino-ethoxy)-      --

Column 112, claim 5, line 25, should read:

--      ylmethyl)-imidazol-1-ylmethyl]-2-cyano-phenoxy}-      --

Signed and Sealed this

Twenty-ninth Day of August, 2000

Attest:

Q. TODD DICKINSON

*Attesting Officer*     *Director of Patents and Trademarks*